(12) United States Patent
Skaar et al.

(10) Patent No.: US 10,045,966 B2
(45) Date of Patent: *Aug. 14, 2018

(54) COMPOSITIONS AND METHODS FOR TREATING MICROBIAL INFECTIONS

(71) Applicant: Vanderbilt Univeristy, Nashville, TN (US)

(72) Inventors: Eric P. Skaar, Brentwood, TN (US); Laura Anzaldi Mike, Nashville, TN (US); Gary Sulikowski, Brentwood, TN (US); Alex Waterson, Murfreesboro, TN (US); Paul Reid, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/494,148

(22) Filed: Apr. 21, 2017

(65) Prior Publication Data

US 2017/0246149 A1 Aug. 31, 2017

Related U.S. Application Data

(63) Continuation of application No. 14/417,277, filed as application No. PCT/US2013/052394 on Jul. 26, 2013, now abandoned.

(60) Provisional application No. 61/676,072, filed on Jul. 26, 2012.

(51) Int. Cl.
| | |
|---|---|
| *A61K 31/415* | (2006.01) |
| *C12Q 1/18* | (2006.01) |
| *A61K 31/4155* | (2006.01) |
| *A61K 45/06* | (2006.01) |
| *A61K 31/7008* | (2006.01) |

(52) U.S. Cl.
CPC ........ *A61K 31/415* (2013.01); *A61K 31/4155* (2013.01); *A61K 31/7008* (2013.01); *A61K 45/06* (2013.01); *C12Q 1/18* (2013.01)

(58) Field of Classification Search
None
See application file for complete search history.

(56) References Cited

U.S. PATENT DOCUMENTS 8,263,642 B2 * 9/2012 Skaar ................... A61K 31/17
424/404
2010/0004324 A1 1/2010 Skaar et al.

OTHER PUBLICATIONS

Murthy et al., Indian Drugs (1985), 22(5), pp. 247-251.*
Yarwood JM, McCormick JK, Schlievert PM. Identification of a novel two-component regulatory system that acts in global regulation of virulence factors of *Staphylococcus aureus*. J Bacteriol. 2001;183(4):1113-23.
Novick RP, Ross HF, Projan SJ, Kornblum J, Kreiswirth B, Moghazeh S. Synthesis of staphylococcal virulence factors is controlled by a regulatory RNA molecule. EMBO J. 1993;12(10):3967-75.
Giraudo AT, Cheung AL, Nagel R. The sae locus of *Staphylococcus aureus* controls exoprotein synthesis at the transcriptional level. Arch Microbiol. 1997;168(1):53-8.
Fournier B, Klier A. Protein A gene expression is regulated by DNA supercoiling which is modified by the ArlS-ArlR two-component system of *Staphylococcus aureus*. Microbiology. 2004;150(Pt 11):3807-19.
Recsei P, Kreiswirth B, O'Reilly M, Schlievert P, Gruss A, Novick RP. Regulation of exoprotein gene expression in *Staphylococcus aureus* by agr. Mol Gen Genet. 1986;202(1):58-61.
Brunskill EW, Bayles KW. Identification and molecular characterization of a putative regulatory locus that affects autolysis in *Staphylococcus aureus*. J Bacteriol. 1996;178(3):611-8.
Martin PK, Li T, Sun D, Biek DP, Schmid MB. Role in cell permeability of an essential two-component system in *Staphylococcus aureus*. J Bacteriol. 1999;181(12):3666-73.
Klevens RM, Morrison MA, Nadle J, Petit S, Gershman K, Ray S, et al. Invasive methicillin-resistant *Staphylococcus aureus* infections in the United States. JAMA. 2007;298(15):1763-71.
Shi L, Sohaskey CD, Kana BD, Dawes S, North RJ, Mizrahi V, et al. Changes in energy metabolism of *Mycobacterium tuberculosis* in mouse lung and under in vitro conditions affecting aerobic respiration. Proc Natl Acad Sci U S A. 2005;102(43):15629-34. PMCID: 1255738.
Endley S, McMurray D, Ficht TA. Interruption of the cydB locus in *Brucella abortus* attenuates intracellular survival and virulence in the mouse model of infection. J Bacteriol. 2001;183(8):2454-62. PMCID: 95161.
Way SS, Sallustio S, Magliozzo RS, Goldberg MB. Impact of either elevated or decreased levels of cytochrome bd expression on *Shigella flexneri* virulence. J Bacteriol. 1999;181(4):1229-37. PMCID: 93501.

(Continued)

*Primary Examiner* — Brian J Davis
(74) *Attorney, Agent, or Firm* — Stites & Harbison PLLC; Mandy Wilson Decker

(57) ABSTRACT

Embodiments of the presently-disclosed subject matter include activators of HssRS that induce endogenous heme biosynthesis by perturbing central metabolism. These molecules are toxic to fermenting *S. aureus*, including clinically relevant small colony variants (SCVs). The utility of targeting fermenting bacteria is exemplified by the fact that this compound prevents the emergence of antibiotic resistance, enhances phagocyte killing, and reduces *S. aureus* pathogenesis. This small molecule is a powerful tool not only for studying bacterial heme biosynthesis and central metabolism, but also establishes targeting of fermentation as a viable antibacterial strategy.

8 Claims, 19 Drawing Sheets

(56) References Cited

OTHER PUBLICATIONS

Somerville GA, Chaussee MS, Morgan CI, Fitzgerald JR, Dorward DW, Reitzer LJ, et al. *Staphylococcus aureus* aconitase inactivation unexpectedly inhibits post-exponential-phase growth and enhances stationary-phase survival. Infect Immun. 2002;70(11):6373-82.
Andries K, Verhasselt P, Guillemont J, Gohlmann HW, Neefs JM, Winkler H, et al. A diarylquinoline drug active on the ATP synthase of *Mycobacterium tuberculosis*. Science. 2005;307(5707):223-7.
Weinstein EA, Yano T, Li LS, Avarbock D, Avarbock A, Helm D, et al. Inhibitors of type II NADH:menaquinone oxidoreductase represent a class of antitubercular drugs. Proc Natl Acad Sci U S A. 2005;102(12):4548-53. PMCID: 555520.
Zoraghi R, See RH, Axerio-Cilies P, Kumar NS, Gong H, Moreau A, et al. Identification of Pyruvate Kinase in Methicillin-Resistant *Staphylococcus aureus* as a Novel Antimicrobial Drug Target. Antimicrob Agents Chemother. 2011;55(5):2042-53.
Akerley BJ, Rubin EJ, Novick VL, Amaya K, Judson N, Mekalanos JJ. A genome-scale analysis for identification of genes required for growth or survival of Haemophilus influenzae. Proc Natl Acad Sci U S A. 2002;99(2):966-71. PMCID: 117414.
Zoraghi R, See RH, Gong H, Lian T, Swayze R, Finlay BB, et al. Functional analysis, overexpression, and kinetic characterization of pyruvate kinase from methicillin-resistant *Staphylococcus aureus*. Biochemistry. 2010;49(35):7733-47.
Cherkasov A, Hsing M, Zoraghi R, Foster LJ, See RH, Stoynov N, et al. Mapping the protein interaction network in methicillin-resistant *Staphylococcus aureus*. J Proteome Res. 2011;10(3):1139-50.
Von Eiff C, Heilmann C, Proctor RA, Woltz C, Peters G, Gotz F. A site-directed *Staphylococcus aureus* hemB mutant is a small-colony variant which persists intracellularly. J Bacteriol. 1997;179(15):4706-12.
Bullen JJ. The significance of iron in infection. Rev Infect Dis. 1981;3(6):1127-38.
Kumar S, Bandyopadhyay U. Free heme toxicity and its detoxification systems in human. Toxicol Lett. 2005;157(3):175-88.
Torres VJ, Stauff DL, Pishchany G, Bezbradica JS, Gordy LE, Iturregui J, et al. A *Staphylococcus aureus* regulatory system that responds to host heme and modulates virulence. Cell Host & Microbe. 2007;1(2):109-19.
Yamamoto Y, Poyart C, Trieu-Cuot P, Lamberet G, Gruss A, Gaudu P. Roles of environmental heme, and menaquinone, in *Streptococcus agalactiae*. Biometals. 2006;19(2):205-10.
Stauff DL, Bagaley D, Torres VJ, Joyce R, Anderson KL, Kuechenmeister L, et al. *Staphylococcus aureus* HrtA is an ATPase required for protection against heme toxicity and prevention of a transcriptional heme stress response. J Bacteriol. 2008;190(10):3588-96.
Schlag S, Fuchs S, Nerz C, Gaupp R, Engelmann S, Liebeke M, et al. Characterization of the oxygen-responsive NreABC regulon of *Staphylococcus aureus*. J Bacteriol. 2008;190(23):7847-58. PMCID: 2583599.
Fernandez A, Lechardeur D, Derre-Bobillot A, Couve E, Gaudu P, Gruss A. Two coregulated efflux transporters modulate intracellular heme and protoporphyrin IX availability in *Streptococcus agalactiae*. PLoS Pathog. 2010;6(4):e1000860.
Stauff DL, Skaar EP. Bacillus anthracis HssRS signalling to HrtAB regulates haem resistance during infection. Molecular Microbiology. 2009;72(3):763-78.
Bibb LA, Schmitt MP. The ABC transporter HrtAB confers resistance to hemin toxicity and is regulated in a hemin-dependent manner by the ChrAS two-component system in Corynebacterium diphtheriae. J Bacteriol. 2010;192(18):4606-17. PMCID: 2937406.
Yamamoto Y, Poyart C, Trieu-Cuot P, Lamberet G, Gruss A, Gaudu P. Respiration metabolism of Group B *Streptococcus* is activated by environmental haem and quinone and contributes to virulence. Mol Microbiol. 2005;56(2):525-34.

Von Eiff C, Peters G, Becker K. The small colony variant (SCV) concept—the role of staphylococcal SCVs in persistent infections. Injury. 2006;37 Suppl 2:S26-33.
Ravichandran M, Ali SA, Rashid NH, Kurunathan S, Yean CY, Ting LC, et al. Construction and evaluation of a O139 Vibrio cholerae vaccine candidate based on a hemA gene mutation. Vaccine. 2006;24(18):3750-61.
Proctor RA, von Eiff C, Kahl BC, Becker K, McNamara P, Herrmann M, et al. Small colony variants: a pathogenic form of bacteria that facilitates persistent and recurrent infections. Nat Rev Microbiol. 2006;4(4):295-305.
Von Eiff C, Bettin D, Proctor RA, Rolauffs B, Lindner N, Winkelmann W, et al. Recovery of small colony variants of *Staphylococcus aureus* following gentamicin bead placement for osteomyelitis. Clin Infect Dis. 1997;25(5):1250-1.
Salgado DR, Bozza FA, Pinto M, al. e, editors. Outbreak with small colony variants of methicillin-resistant *S. aureus* in an ICU. Interscience Conference on Antibmicrobial Agents and Chemotherapy; 2002 Dec. 19, 2001; Chicago, IL.
Seifert H, von Eiff C, Fatkenheuer G. Fatal case due to methicillin-resistant *Staphylococcus aureus* small colony variants in an AIDS patient. Emerg Infect Dis. 1999;5(3):450-3.
Ponce E, Flores N, Martinez A, Valle F, Bolivar F. Cloning of the two pyruvate kinase isoenzyme structural genes from *Escherichia coli*: the relative roles of these enzymes in pyruvate biosynthesis. J Bacteriol. 1995;177(19):5719-22.
Stauff DL, Torres VJ, Skaar EP. Signaling and DNA-binding Activities of the *Staphylococcus aureus* HssR-HssS Two-component System Required for Heme Sensing. J Biol Chem. 2007;282(36):26111-21.
Stauff DL, Skaar EP. Bacillus anthracis HssRS signaling to HrtAB regulates heme resistance during infection. Mol Microbiol. 2009.
Francis KP, Joh D, Bellinger-Kawahara C, Hawkinson MJ, Purchio TF, Contag PR. Monitoring bioluminescent *Staphylococcus aureus* infections in living mice using a novel luxABCDE construct. Infect Immun. 2000;68(6):3594-600.
Mazmanian SK, Liu G, Ton-That H, Schneewind O. *Staphylococcus aureus* sortase, an enzyme that anchors surface proteins to the cell wall. Science. 1999;285(5428):760-3.
Reniere ML, Skaar EP. *Staphylococcus aureus* haem oxygenases are differentially regulated by iron and haem. Mol Microbiol. 2008;69(5):1304-15.
Baell JB, Holloway GA. New Substructure Filters for Removal of Pan Assay Interference Compounds (PAINS) from Screening Libraries and for Their Exclusion in Bioassays. J Med Chem. 2010;53(7):2719-40.
Workman P, Collins I. Probing the Probes: Fitness Factors for Small Molecule Tools. Chem Biol. 2010;17(6):561-77.
Boxer MB, Jiang JK, Vander Heiden MG, Shen M, Skoumbourdis AP, Southall N, et al. Evaluation of substituted N, N'-diarylsulfonamides as activators of the tumor cell specific M2 isoform of pyruvate kinase. J Med Chem. 2010;53(3):1048-55. PMCID: 2818804.
De Been M, Bart MJ, Abee T, Siezen RJ, Francke C. The identification of response regulator-specific binding sites reveals new roles of two-component systems in Bacillus cereus and closely related low-GC Gram-positives. Environ Microbiol. 2008;10(10):2796-809.
Terstappen GC, Schlüpen C, Raggiaschi R, Gaviraghi G. Target deconvolution strategies in drug discovery. Nat Rev Drug Discov. 2007;6(11):891-903.
Pucheault M. Natural products: chemical instruments to apprehend biological symphony. Org Biomol Chem. 2008;6(3):424.
Piggott AM, Karuso P. Rapid Identification of a Protein Binding Partner for the Marine Natural Product Kahalalide F by Using Reverse Chemcial Proteomics. Chem Eur J of Chem Bio. 2008;9(4):524-30.
Dorman G, Prestwich G. Using photolabile ligands in drug discovery and development. Trends Biotechnol. 2000;18(2):64-77.
Fleming S. Chemical Reagents in Photoaffinity-Labeling. Tetrahedron. 1995;51(46):12479-520.

(56) References Cited

OTHER PUBLICATIONS

Yamamoto S, Abe M, Nakanishi S, Murai M, Miyoshi H. Synthesis and characterization of photoaffinity probe of acetogenin, a strong inhibitor of mitochondrial complex I. Tetrahedron Letters. 2011;52(24):3090-3.
Liu Q, Tor Y. Simple conversion of aromatic amines into azides. Org Lett. 2003;5(14)2571-2.
Uddin MJ, Crews BC, Ghebreselasie K, Tantawy MN, Marnett LJ. [I-123]-Celecoxib Analogues as SPECT Tracers of Cyclooxygenase-2 in Inflammation. Acs Med Chem Lett. 2011;2(2):160-4.
Dorman G, Olszewski J, Prestwich G, Hong Y, Ahern D. Synthesis of Highly Tritiated 4-Benzoyl-L-Phenylalanine, A Photoactivatable Amino-Acid. J Org Chem. 1995;60(7):2292-7.
Mesange F, Sebbar M, Capdevielle J, Guillemot J, Ferrara P, Bayard F, et al. Identification of two tamoxifen target proteins by photolabeling with 4-(2-morpholinoethoxy)benzophenone. Bioconjugate Chem. 2002;13(4):766-72.
Elizalde L, de los Santos G, Garcia A, Medellin D, Acosta R. Synthesis of novel photochromic 6-benzyloxo-spirobenzopyran compounds. Synthetic Commun. 2005;35(24):3087-97.
Lamos SM, Krusemark CJ, McGee CJ, Scalf M, Smith LM, Belshaw PJ. Mixed isotope photoaffinity reagents for identification of small-molecule targets by mass spectrometry. Angew Chem Int Edit. 2006;45(26):4329-33.
Bae T, Schneewind O. Allelic replacement in *Staphylococcus aureus* with inducible counter-selection. Plasmid. 2006;55(1):58-63.
Pishchany G, McCoy AL, Torres VJ, Krause JC, Crowe JE, Jr., Fabry ME, et al. Specificity for human hemoglobin enhances *Staphylococcus aureus* infection. Cell Host Microbe. 2010;8(6):544-50.
Crosa J. H. ARM, and S. M. Payne. . Iron Transport in Bacteria. Jorge H. Crosa ARM, Shelley M. Payne, editor. Washington, D.C.: A.S.M. Press; 2004.
Hood MI, Jacobs AC, Sayood K, Dunman PM, Skaar EP. Acinetobacter baumannii Increases Tolerance to Antibiotics in Response to Monovalent Cations. Antimicrob Agents Chemother. 2010;54(3)1029-41. PMCID: 2825970.
Torres VJ, Attia AS, Mason WJ, Hood MI, Corbin BD, Beasley FC, et al. *Staphylococcus aureus* fur regulates the expression of virulence factors that contribute to the pathogenesis of pneumonia. Infect Immun. 2010;78(4):1618-28. PMCID: 2849423.
Kim JS, Lim HK, Lee MH, Park JH, Hwang EC, Moon BJ, et al. Production of porphyrin intermediates in *Escherichia coli* carrying soil metagenomic genes. FEMS Microbiol Lett. 2009;295(1):42-9.
Friedman DB, Stauff DL, Pishchany G, Whitwell CW, Torres VJ, Skaar EP. *Staphylococcus aureus* Redirects Central Metabolism to Increase Iron Availability. PLoS Pathog. 2006;2(8).
Skaar EP, Gaspar AH, Schneewind O. IsdG and IsdI, heme-degrading enzymes in the cytoplasm of *Staphylococcus aureus*. J Biol Chem. 2004;279(1):436-43.
Corbin BD, Seeley EH, Raab A, Feldmann J, Miller MR, Torres VJ, et al. Metal chelation and inhibition of bacterial growth in tissue abscesses. Science. 2008;319(5865):962-5.
Attia AS, Benson MA, Stauff DL, Torres VJ, Skaar EP. Membrane damage elicits an immunomodulatory program in *Staphylococcus aureus*. PLoS Pathog. 2010;6(3):e1000802. PMCID: 2837406.
Skaar E, Humayun M, Bae T, DeBord K, Schneewind O. Iron-source preference of *Staphylococcus aureus* infections. Science. 2004;305:1626-8.
Torres V, Pishchany G, Humayun M, Schneewind O, Skaar E. *Staphylococcus aureus* IsdB is a hemoglobin receptor required for heme iron utilization. J Bacteriol. 2006;188:8421-9.
Jenkins A, Cote C, Twenhafel N, Merkel T, Bozue J, Welkos S. Role of purine biosynthesis in Bacillus anthracis pathogenesis and virulence. Infect Immun. 2011;79(1):153-66. PMCID: 3019915.
Samant S, Hsu FF, Neyfakh AA, Lee H. The Bacillus anthracis protein MprF is required for synthesis of lysylphosphatidylglycerols and for resistance to cationic antimicrobial peptides. J Bacteriol. 2009;191(4):1311-9. PMCID: 2631992.
Fry B, Zhu T, Domach MM, Koepsel RR, Phalakornkule C, Ataai MM. Characterization of growth and acid formation in a Bacillus subtilis pyruvate kinase mutant. Appl Environ Microbiol. 2000;66(9):4045-9. PMCID: 92257.
Zhu T, Phalakomkule C, Koepsel RR, Domach MM, Ataai MM. Cell growth and by-product formation in a pyruvate kinase mutant of *E. coli*. Biotechnol Prog. 2001;17(4):624-8.
Skaar EP, Gaspar AH, Schneewind O. Bacillus anthracis IsdG, a heme-degrading monooxygenase. J Bacteriol. 2006;188(3):1071-80. PMCID: 1347327.
Mazmanian, S., E. Skaar, A. Gaspar, M. Humayun, P. Gomicki, J. Jelenska, A. Joachmiak, D. Missiakas, O. Schneewind. 2003. Passage of heme-iron across the envelope of *Staphylococcus aureus*. Science 299: 906-909.
Proctor, R., B. Kahl, C. von Eiff, P. Vaudaux, D. Lew, G. Peters. 1998. Staphylococcal small colony variants have novel mechanisms for antibiotic resistance. Clin. Infect. Dis. S68-74.
Pantosti A & Venditti M (2009) What is MRSA? Eur Respir J 34(5):1190-1196.
Somerville GA & Proctor RA (2009) At the crossroads of bacterial metabolism and virulence factor synthesis in staphylococci. Microbiol Mol Biol Rev 73(2):233-248.
Mazmanian S, et al. (2003) Passage of heme-iron across the envelope of *Staphylococcus aureus*. Science 299:906-909.
Johansson P & Hederstedt L (1999) Organization of genes for tetrapyrrole biosynthesis in Gram-positive bacteria. Microbiology 145(3):529-538.
Bryan LE & Kwan S (1981) Aminoglycoside-resistant mutants of Pseudomonas aeruginosa deficient in cytochrome d, nitrite reductase, and aerobic transport. Antimicrob Agents Chemother 19(6):958-964.
Schmitt MP (1999) Identification of a two-component signal transduction system from Corynebacterium diphtheriae that activates gene expression in response to the presence of heme and hemoglobin. J Bacteriol 181(17):5330-5340.
Youngman PJ, Perkins JB, & Losick R (1983) Genetic transposition and insertional mutagenesis in Bacillus subtilis with *Streptococcus faecalis* transposon Tn917. Proc Natl Acad Sci U S A 80(8):2305-2309.
McIllmurray MB & Lascelles J (1970) Anaerobiosis and the activity of enzymes of pyrimidine biosynthesis of *Staphylococcus aureus*. J Gen Microbiol 64(3).
Fitzpatrick TB, et al. (2007) Two independent routes of de novo vitamin B6 biosynthesis: not that different after all. Biochem J 407(1):1-13.
Wick AN, et al. (1957) Localization of the primary metabolic block produced by 2-deoxyglucose. Journal of Biological Chemistry 224(2):963-969.
Deleo FR, Diep BA, & Otto M (2009) Host defense and pathogenesis in *Staphylococcus aureus* infections. Infectious Disease Clinics of North America 23(1):17-34.
Richardson AR, Libby SJ, & Fang FC (2008) A nitric oxide-inducible lactate dehydrogenase enables *Staphylococcus aureus* to resist innate immunity. Science 319(5870):1672-1676.
Cheng AG, DeDent AC, Schneewind O, & Missiakas D (2011) A play in four acts: *Staphylococcus aureus* abscess formation. Trends Microbiol 19(5):225-232.
Park MK, Myers Ram, & Marzella L (1992) Oxygen tensions and infections: Modulation of microbial growth, activity of antimicrobial agents, and immunologic responses. Clinical Infectious Diseases 14(3):720-740.
Burka LT, Washburn KD, & Irwin RD (1991) Disposition of [14C]furan in the male F344 rat. J Toxicol Environ Health 34(2):245-257.
Manier ML, et al. (2011) Reagent precoated targets for rapid in-tissue derivatization of the anti-tuberculosis drug isoniazid followed by MALDI imaging mass spectrometry. J Am Soc Mass Spectrom 22(8):1409-1419.
Barker KD, Barkovits K, & Wilks A (2012) Metabolic flux of extracellular heme uptake in Pseudomonas aeruginosa is driven by

(56) References Cited

OTHER PUBLICATIONS the iron-regulated heme oxygenase (HemO). Journal of Biological Chemistry 287(22):18342-18350.

Doss M & Philipp-Dormston WK (1973) Regulatory link between lactate dehydrogenase and biosynthesis of porphyrin and heme in microorganisms. Enzyme 16(1).

Frunzke J, Gatgens C, Brocker M, & Bott M (2011) Control of heme homeostasis in Corynebacterium glutamicum by the two-component system HrrSA. (Translated from eng) J Bacteriol 193(5):1212-1221 (in eng).

Jurtshuk PJ (1996) Bacterial Metabolism. Medical Microbiology, ed Baron S (University of Texas Medical Branch at Galveston, Galveston ), 4th Ed.

Bullen JJ, and Griffiths, E.; Iron and Infection: Molecular, Physiological and Clinical Aspects, 2nd Edition; Shock; Nov. 1999; vol. 12. No. 5; p. 410.

Stauff DL, Skaar EP; The Heme Sensor System of *Staphylococcus aureus*; Contrib Microbiol. Basel, Karger, 2009, vol. 16, pp. 120-135.

Cheng K-W, Wong C-C, Wang M, He Q-Y, Chen F. Identification and characterization of molecular targets of natural products by mass spectrometry; Mass Spectrometry Reviews, 2010, 29, pp. 126-155.

Stary E, Gaupp R, Lechner S, Leibig M, Tichy E, Kolb M, et al. New Architectures for Tet-On and Tet-Off Regulation in *Staphylococcus aureus*; Appl Environ Microbiol.; Feb. 2010; vol. 76(3); pp. 680-687.

\* cited by examiner

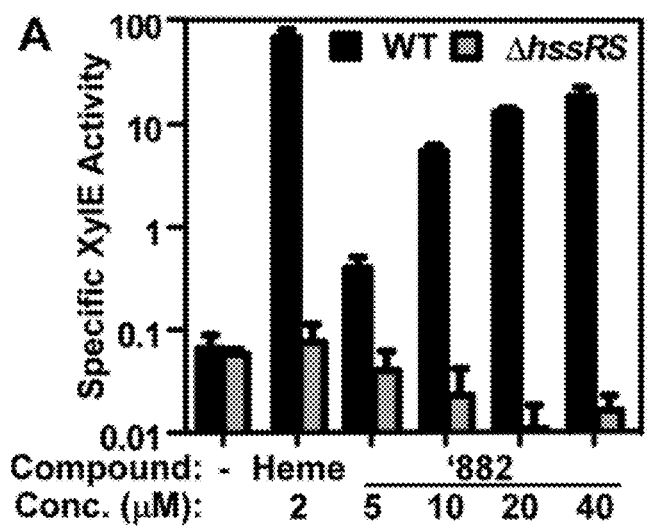
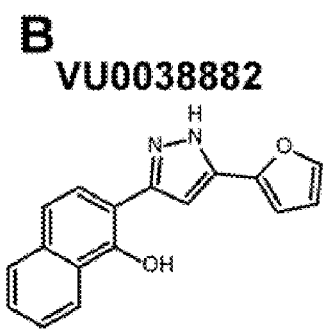
Figure 9A
Figure 9B
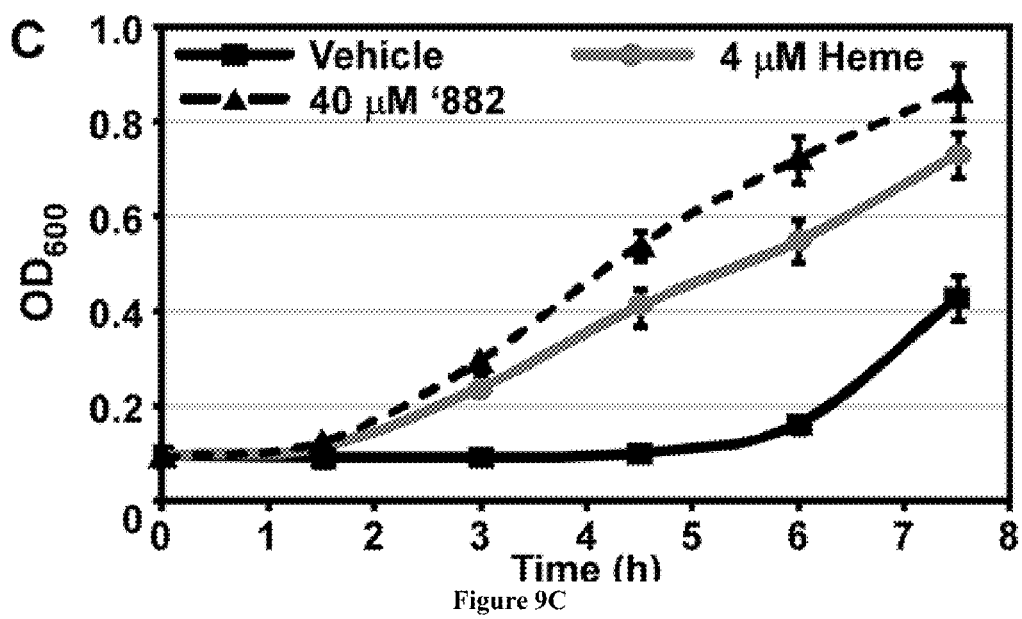
Figure 9C

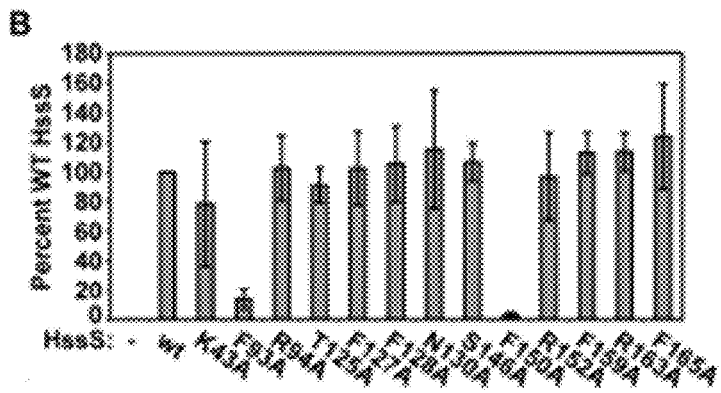
Figure 10A
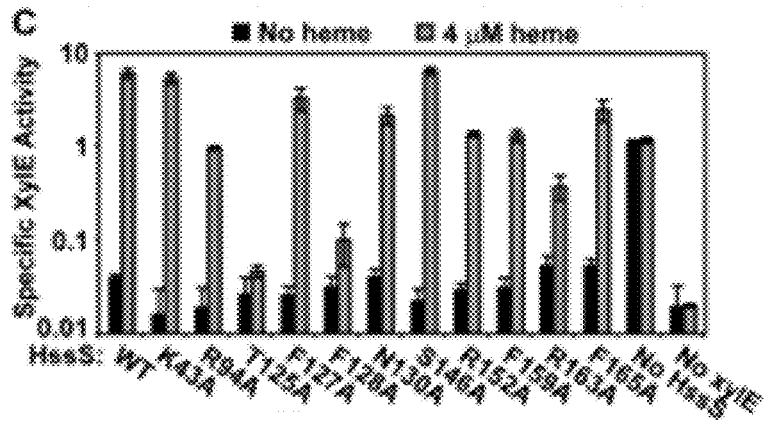
Figure 10B
Figure 10C

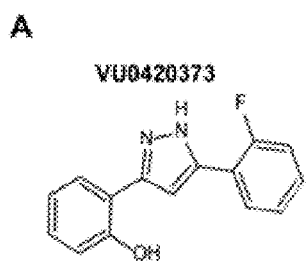
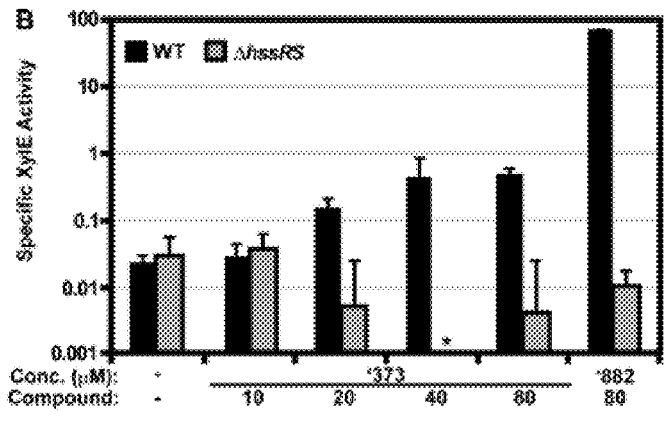
Figure 15A
Figure 15B
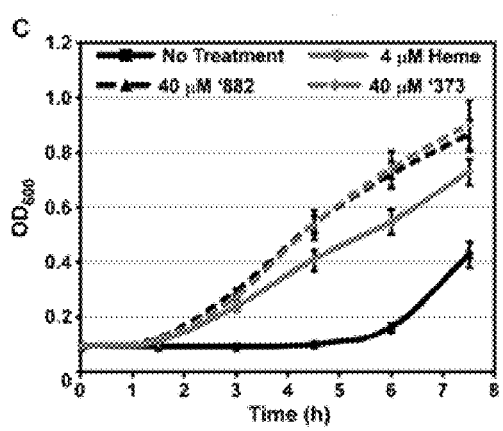
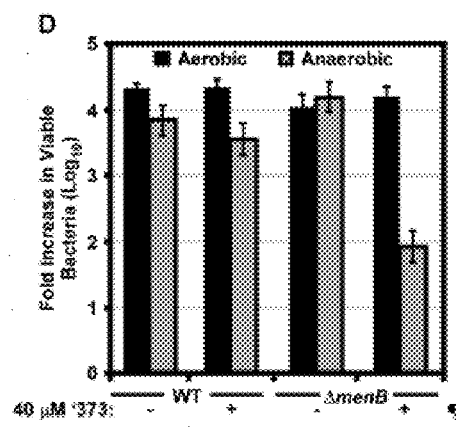
Figure 15C
Figure 15D

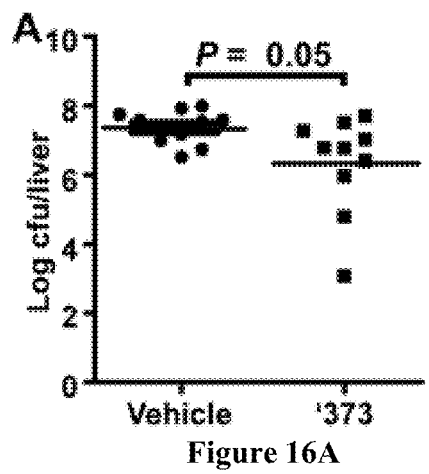
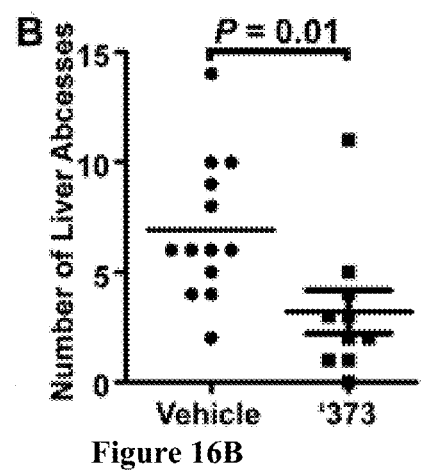
Figure 16A             Figure 16B
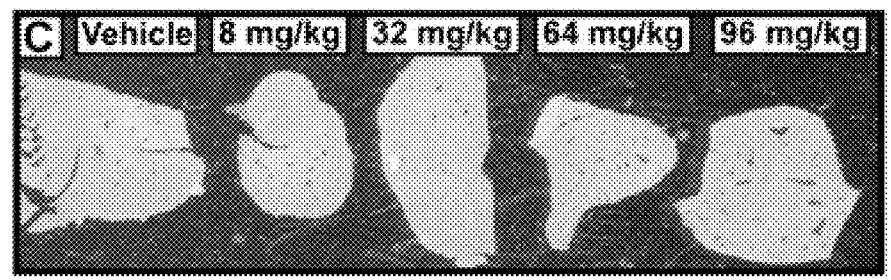
Figure 16C
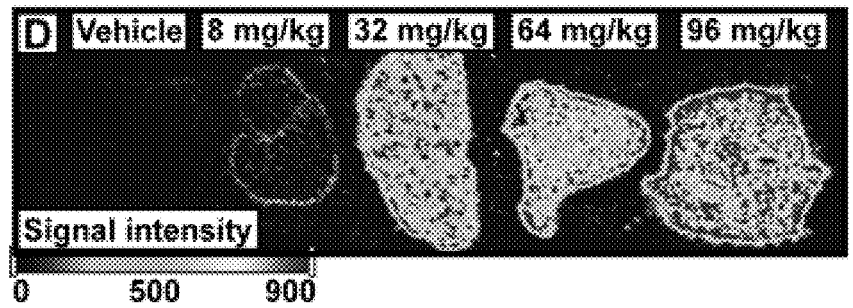
Figure 16D

COMPOSITIONS AND METHODS FOR TREATING MICROBIAL INFECTIONS

RELATED APPLICATIONS

This application claims priority from U.S. application Ser. No. 14/417,277, which is a national stage entry of International Patent Application No. PCT/US13/52394 filed Jul. 26, 2013, which claims the benefit of U.S. Provisional Application Ser. No. 61/676,072 filed Jul. 26, 2012.

GOVERNMENT INTEREST

This invention was made with government support under U54 AI057157-06, AI073843, T32 HL069765, and AI069233, each awarded by National Institutes of Health. The government has certain rights in the invention.

TECHNICAL FIELD

The presently-disclosed subject matter relates to treatment of microbial infections. In particular, the presently-disclosed subject matter relates to fermentation inhibitors and the treatment of microbial infections.

INTRODUCTION

The rapidly increasing resistance of pathogenic bacteria to all relevant antimicrobials is a tremendous threat to global public health and has galvanized efforts focused on uncovering new targets for therapeutic intervention. In the past, the most successful antibiotic development strategies have exploited bacterial systems that are absolutely required for growth in culture. However, these screening strategies have prevented the identification of small molecules that target pathways conditionally required during infection. Most bacterial pathogens have multiple ways of generating energy through central metabolic pathways that permit these organisms to adapt to alterations in available oxygen and the presence of diverse electron acceptors. Therefore, flexibility in the regulation of central metabolism is critical to infectivity, based on the diverse environments that pathogens encounter when colonizing the vertebrate host.

However, despite the tremendous therapeutic potential, small molecule screening strategies based on growth inhibition have not identified candidate therapeutics that target central metabolism.

BRIEF DESCRIPTION OF THE DRAWINGS

FIGS. 9A-9C describe a high throughput screen that identifies small molecule activators of HssRS. (A) A secondary screen consisting of a XylE reporter assay verified the activity of the top 110 hits from the primary screen, including '882. Triplicate cultures of S. aureus WT and ΔhssR transformed with the hrtAB promoter-xylE fusion-containing plasmid (phrt.xylE) were grown in the presence of the indicated additive and XylE activity was measured. (B) The structure of lead compound VU0038882 ('882). (C) '882 was confirmed as a hit in a tertiary screen that measured the ability of the compound to pre-adapt S. aureus for growth in 20 μM heme. Triplicate cultures of WT S. aureus were grown overnight in medium containing the indicated additive and sub-cultured into medium containing 20 μM heme. Growth was monitored by measuring the optical density at 600 nm ($OD_{600}$) over time. (A and C) Error bars represent one standard deviation from the mean.

FIGS. 10A-10F show that HssS extracytoplasmic domain residues are required for heme and '882 sensing. (A) HssS extracytoplasmic domain residues are conserved across Firmicutes (1). Shown is the conservation of residues (colored bars), HssS consensus sequence (capitalized letters), and the S. aureus COL HssS sequence (lower case letters). Red bars represent conserved residues; asterisks denote residues selected for mutagenesis studies. (B) Expression levels of each HssS-Myc mutant was assessed by immunoblot. Membrane-containing fractions were prepared from ΔhssS expressing no HssS (−), c-Myc-tagged wildtype HssS (WT), and c-Myc-tagged HssS variants containing the indicated mutations. The level of each point mutant is expressed as the percent abundance of WT HssS-Myc. (C) Effect of HssS extracytoplasmic domain mutations on heme sensing activity. Plasmids were constructed that contain an hrtAB promoter-xylE fusion and express the indicated HssS-Myc variant. These strains were grown in the absence of heme or in 4 µM heme and XylE activity was determined. Included in this analysis was a strain containing the hrtAB promoter reporter without HssS-Myc (no HssS) and a strain containing a promoterless xylE (no xylE). (D) Dose-dependent activity of HssS-Myc point mutants. HssS-Myc mutants were grouped according to the magnitude to which the mutation affects heme-dependent induction of XylE activity according to the data shown in C (low effect: no reduction; medium effect: between WT and 1 unit of XylE activity; high effect: between 1 unit of XylE activity and background). Included in this analysis was a strain containing the hrtAB promoter reporter and no copy of HssS-Myc (no HssS) and a strain containing a promoterless xylE (no xylE). The strains were grown in the presence of the indicated heme concentration and XylE reporter activity was determined. (E) Rescue of $S.$ $aureus$ ΔhssS heme sensitivity by HssS-Myc point mutants. $S.$ $aureus$ ΔhssS (−) or ΔhssS expressing the indicated HssS-Myc variants were grown for 24 h in the presence of 30 µM heme and culture density was determined. (F) $S.$ $aureus$ ΔhssS was transformed with plasmids containing an hrtAB promoter-xylE fusion and encoding Myc-tagged, WT HssS (HssS-Myc), or HssS-Myc mutated at the indicated extracytoplasmic domain residue (R94A, T125A, or F165A). The resulting strains were grown in the presence of the indicated concentration of heme (left) or '882 (right) and XylE activity was quantified. In all cases, triplicate experiments were performed and averaged; error bars represent one standard deviation from the mean.

FIGS. 15A-15D shows additional embodiments of the present invention. (A) Shown is the structure of derivative VU0420373 ('373). (B) Triplicate cultures of *S. aureus* wildtype (WT) and ΔhssR transformed with either a promoterless xylE-containing plasmid (pxylE) or an hrtAB promoter-xylE fusion-containing plasmid (phrt.xylE) were grown in medium containing the indicated additive. Following growth to stationary phase, XylE activity was measured and normalized to lysate protein concentrations. An asterisk denotes the value was below the limit of detection. (C) Triplicate cultures of *S. aureus* were grown overnight in medium containing the indicated additive. Cultures were back-diluted into medium containing 20 μM heme. The absorbance at 600 nm ($OD_{600}$) was taken at the indicated times after inoculation. (D) *S. aureus* WT and the menaquinone auxotroph (ΔmenB) were grown in triplicate under aerobic and anaerobic conditions in the presence of vehicle (DMSO) or 40 μM '373. CFUs were enumerated at the beginning and end of the time course. Based on these values, the fold increase over the input of bacteria was determined. (B-D) Error bars represent one standard deviation from the mean.

FIGS. 16A-16D show embodiments of the preset invention reduce *S. aureus* pathogenesis in vivo. Mice infected retroorbitally with *S. aureus* were treated intraperitoneally with vehicle (10% Tween 80) or '373. After 96 h mice were sacrificed and (A) CFUs and (B) surface abscesses were enumerated from the livers. Each marker represents an individual mouse. Data were collected from three independent experiments resulting in n=13 for vehicle and n=12 for '373-treated mice once the highest and lowest values were removed from each group. The horizontal line indicates the mean and the error bars represent the standard error of the mean. Statistical significance was determined by a two-tailed Student's t-test. Livers from mice treated with the indicated dose of '373 were harvested 24 h post-infection (1 h after the $2^{nd}$ treatment), sectioned, and mounted on MALDI target plates (C). (D) Tissue sections were imaged by MALDI-MS/MS for accumulation of a fragment of '373 by MALDI-MS/MS (m/z 255.2→134). Spectra were acquired at 10 microscans per step. 5 laser shots were acquired per pixel and pixels were obtained every 100 μm.

DESCRIPTION OF EXEMPLARY EMBODIMENTS

Figure 1:
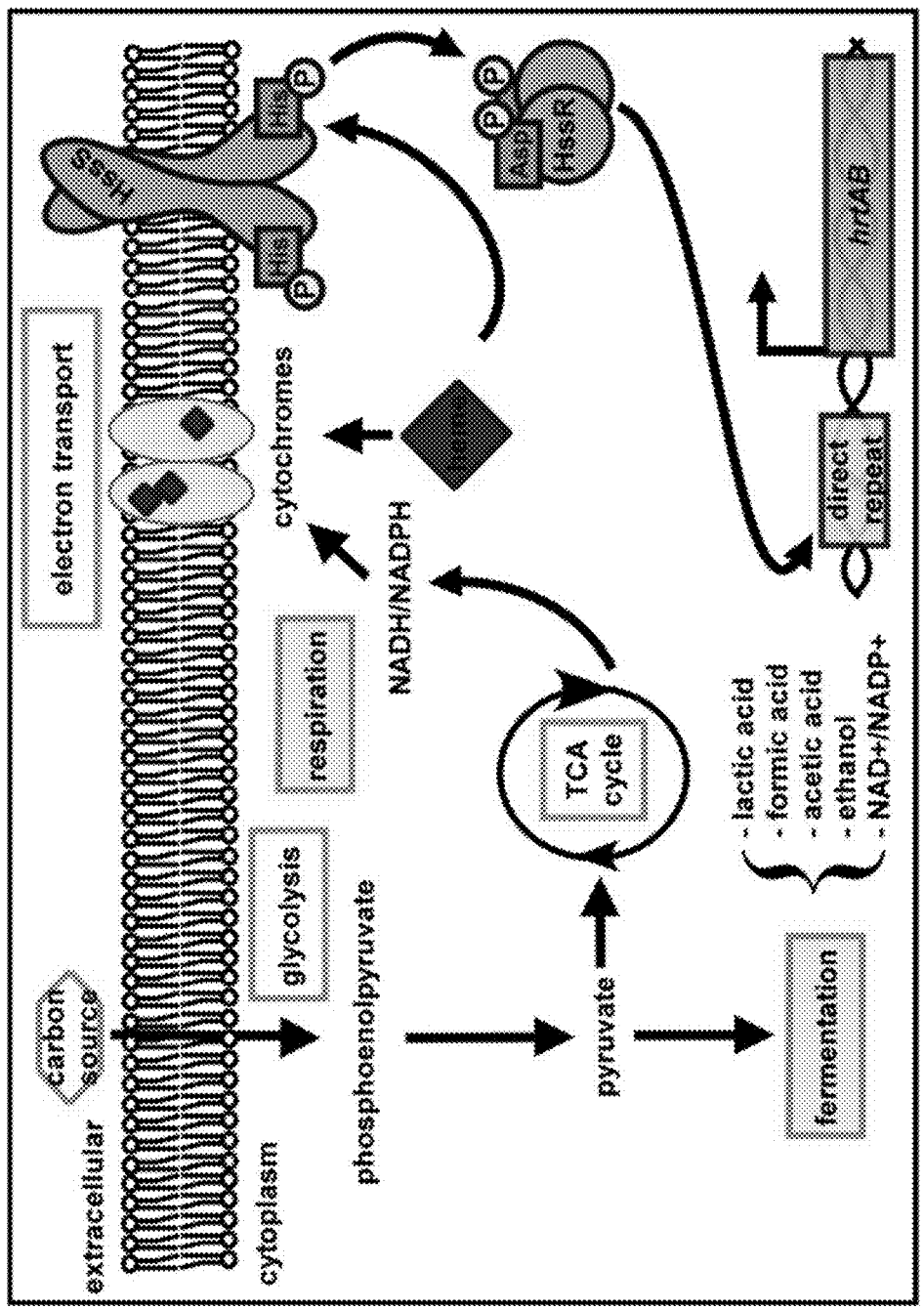
FIG. 1 is a simplified model of the central metabolic pathways in gram positive pathogens that are targeted by compositions and methods of the presently-disclosed subject matter. Briefly, glucose enters the cell as the initial substrate for glycolysis. The final step in glycolysis is the conversion of phosphoenolpyruvate to pyruvate by pyruvate kinase. Pyruvate is either fermented to lactate, or enters the TCA cycle which leads to the reduction of NAD+ to NADH which is reoxidized through the electron transport chain. Cytochromes within the electron transport chain require heme to carry electrons to terminal electron acceptors. Compounds, compositions, and methods of the presently-disclosed subject matter increase the intracellular heme levels (e.g., heme biosynthesis), which profoundly impacts respiration of the pathogens.

The presently-disclosed subject matter includes compounds, compositions, kits, systems, and methods useful for treating microbial infections. The presently-disclosed subject matter further includes methods useful for screening for fermentation inhibitors, and compounds useful as probes.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

Certain pathogens, for example, the Gram positive pathogen *Staphylococcus aureus*, are a significant threat to public health. There is an increasing incidence of both community acquired- and hospital associated-multidrug resistant staphylococci. Upon infection, the human immune system assaults *S. aureus* with a myriad of reactive oxygen species, which disrupt staphylococcal respiration. The present inventors have identified a family of small molecules that manipulate the respiratory state of bacteria. The present inventors have data that support that these molecules inhibit bacterial fermentation. Such molecules may potentiate the susceptibility of the bacteria to the host immune system and other antibiotics. Due to the fact that many bacterial pathogens generate energy through fermentation, the present inventors contemplate that these molecules have therapeutically efficacy against a variety of infectious diseases.

Antibiotic treatment of, for example, *S. aureus* infections may lead to the selection of a sub-population of small colony variants (SCVs). SCVs are regularly isolated from the lungs of cystic fibrosis patients and medical implants. SCVs are highly resistant to antibiotics and difficult to eliminate. This ability is conferred on the bacteria as they do not utilize respiration and wholly rely on fermentation to generate energy. The co-administration of these molecules may prevent the emergence of SCVs during persistent infections or may treat current SCV infections. It is useful to point out that other bacteria form SCVs and that the small molecules described herein are contemplated to have therapeutic utility against a range of human pathogens. Studies by the present inventors suggest that the small molecules are also active in, for example, *Bacillus anthracis, Streptococcus pyogenes, Enterococcus faecalis,* and *Lactococcus lactis.*

The small molecules identified herein are contemplated to have further utility in the laboratory setting. There is currently no molecule known that inhibits bacterial fermentation. Therefore these molecules can serve as viable probes to study bacterial physiology.

In one aspect of the present invention, the inventors probed the mechanism of HssS stimulation by identifying small molecule activators of HssS. The most potent compound, VU0038882 ('882), activates HssRS by inducing endogenous heme biosynthesis in *S. aureus*, leading to increased intracellular heme levels. The metabolic alterations induced by '882 are toxic to fermenting *S. aureus*. Therapeutic development of '882 has revealed that this compound is synergistic with known respiration inhibitors, is highly antimicrobial against fermenting bacteria including SCVs, and virtually eliminates the development of resistance to aminoglycoside antibiotics. Notably, a derivative of '882 reduces bacterial burdens in a systemic model of staphylococcal infection, underscoring the therapeutic value of targeting bacterial fermentation.

In identifying fermentation inhibitors as described herein, the present inventors surprisingly and unexpectedly discovered that certain compounds that can act as fermentation inhibitors also modulate heme production. Although not previously suggested heretofor, it now appears that inhibition of fermentation could result in an increase in heme production.

The presently-disclosed subject matter includes compounds useful for inhibiting fermentation and/or affecting antimicrobial activity. In some embodiments, the compounds of the presently-disclosed subject matter are compounds of the formula:

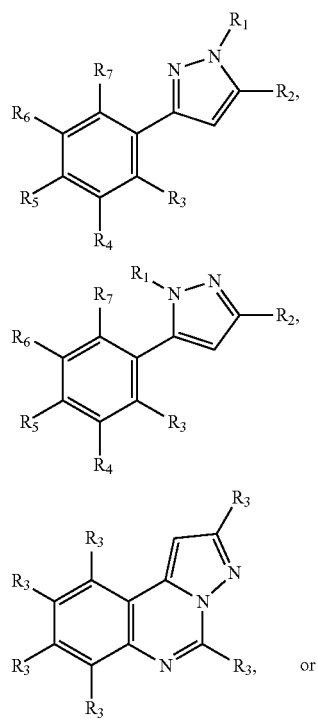

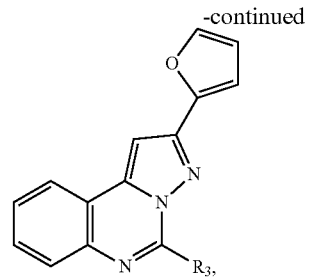

wherein,
$R_1$ is H, alkyl, aryl, heteroaryl;
$R_2$ is H, halogen, alkyl, aryl, heteroaryl;
$R_3$ is H, halogen, hydroxyl, alkoxy, alkyl, aryl, heteroaryl, amino, amino sulfonyl, acetamide;
$R_4$ is H, halogen, hydroxyl, alkoxy, alkyl, aryl, heteroaryl, amino, amino sulfonyl, acetamide;
$R_5$ is H, halogen, hydroxyl, alkoxy, alkyl, aryl, heteroaryl, amino, amino sulfonyl, acetamide;
$R_6$ is H, halogen, hydroxyl, alkoxy, alkyl, aryl, heteroaryl, amino, amino sulfonyl, acetamide;
$R_7$ is H, halogen, hydroxyl, alkoxy, alkyl, aryl, heteroaryl, amino, amino sulfonyl, acetamide;
$R_8$ is —$CR_3$, O, S;
wherein $R_5$ and $R_6$, $R_7$ and $R_6$, $R_5$ and $R_4$, $R_4$ and $R_3$ can cyclize forming a 3-10 member ring comprising C, O, S, and/or N optionally substituted with one or more $R_3$.

In other embodiments, $R_1$ is H, alkyl, aryl; $R_2$ is H, halogen, alkyl, aryl, heteroaryl; $R_3$ is H, alkyl, hydroxyl, alkoxy, amino, amino sulfonyl, acetamide, aryl, heteroaryl; $R_4$ is H, alkyl, hydroxyl, alkoxy, amino, amino sulfonyl, acetamide; $R_5$ is H, alkyl, hydroxyl, alkoxy, amino, amino sulfonyl, acetamide; and $R_6$ is H, alkyl, aryl.

In other embodiments,
$R_1$ is H or

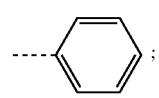

$R_2$ is

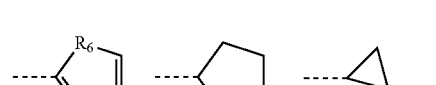

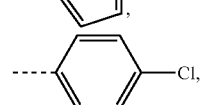

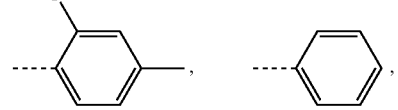

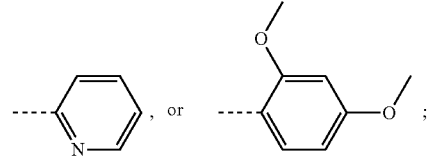

$R_3$ is H,

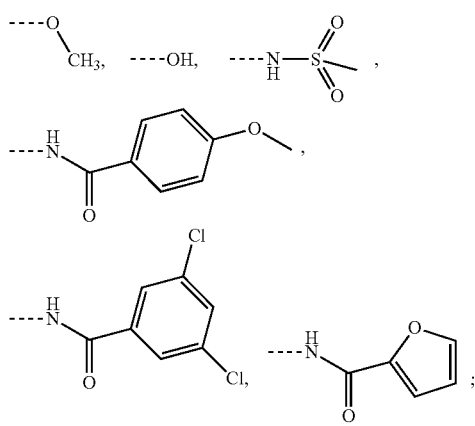

$R_4$ is H, OH,

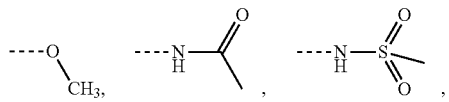

or $R_4$ and $R_5$, taken together with the carbon atoms to which they are bonded, can form an aromatic ring containing 6 carbon atoms;
$R_5$ is H, OH,

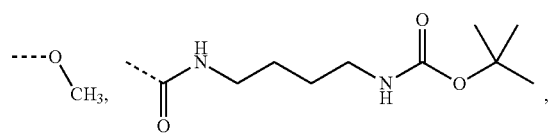

or $R_4$ and $R_5$, taken together with the carbon atoms to which they are bonded, can form an aromatic ring containing 6 carbon atoms, or $R_5$ and $R_6$, taken together with the carbon atoms to which they are bonded, can form an aromatic ring containing 6 carbon atoms;
$R_6$ is H, or $R_5$ and $R_6$, taken together with the carbon atoms to which they are bonded, can form an aromatic ring containing 6 carbon atoms;
$R_7$ is H or OH.

Also included in the presently-disclosed subject matter are the compounds as set forth in Table 1.

TABLE 1

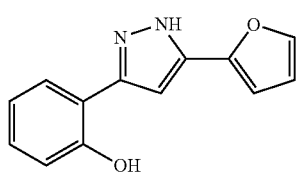 [SMILES: Oc1ccccc1-c1cc(-c2ccco2)[nH]n1]

TABLE 1-continued

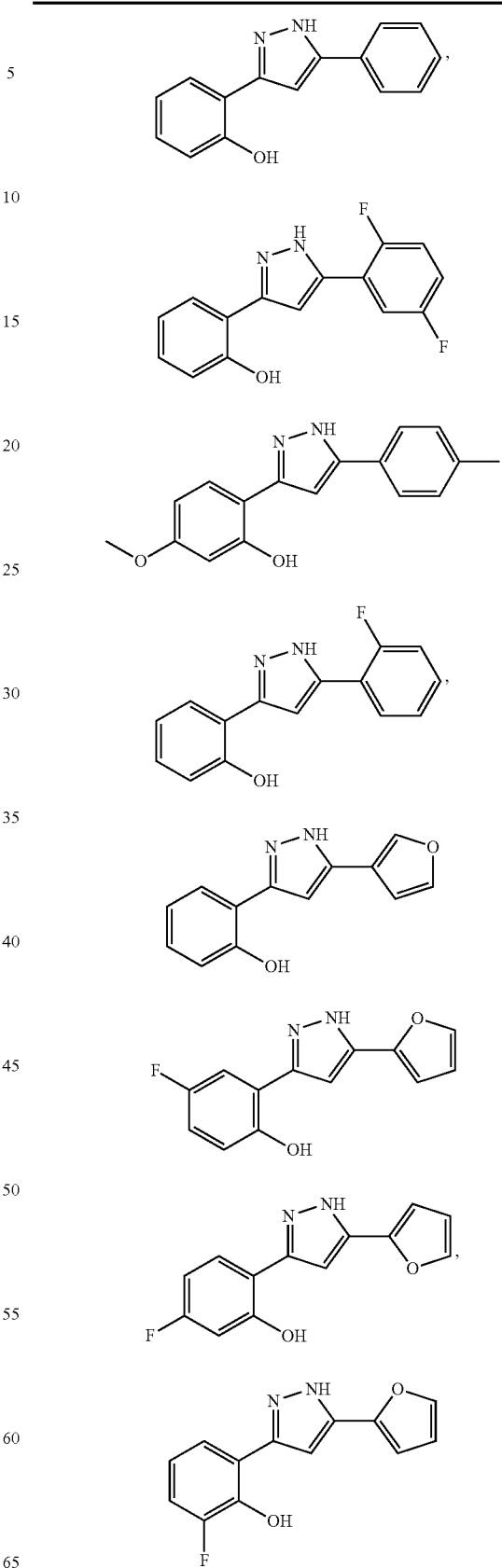

TABLE 1-continued
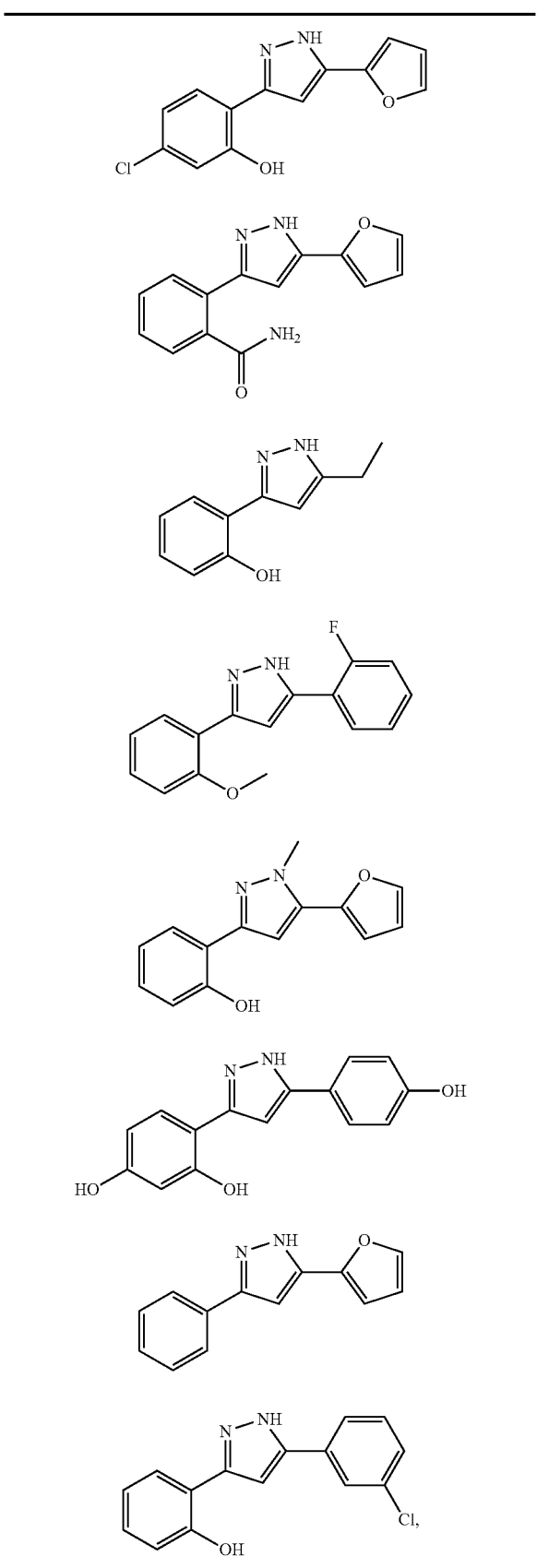
TABLE 1-continued
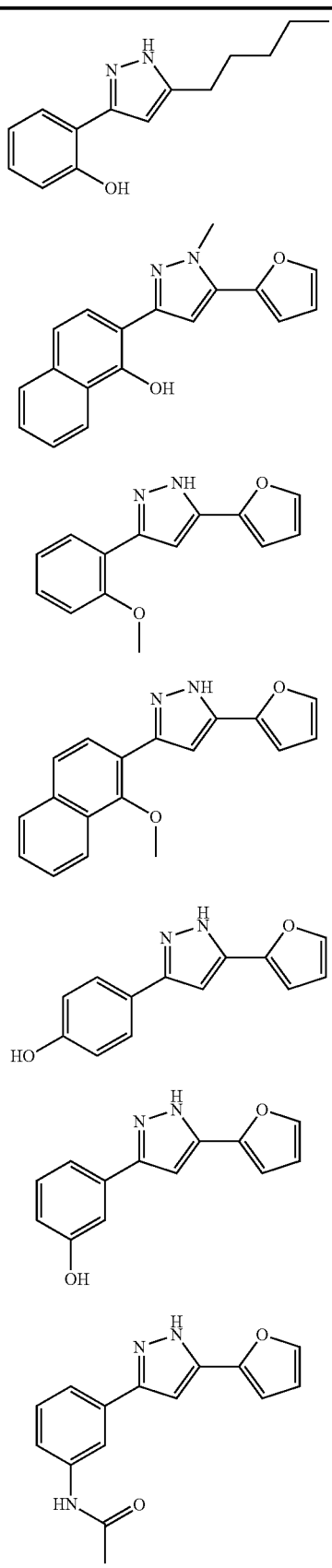

TABLE 1-continued
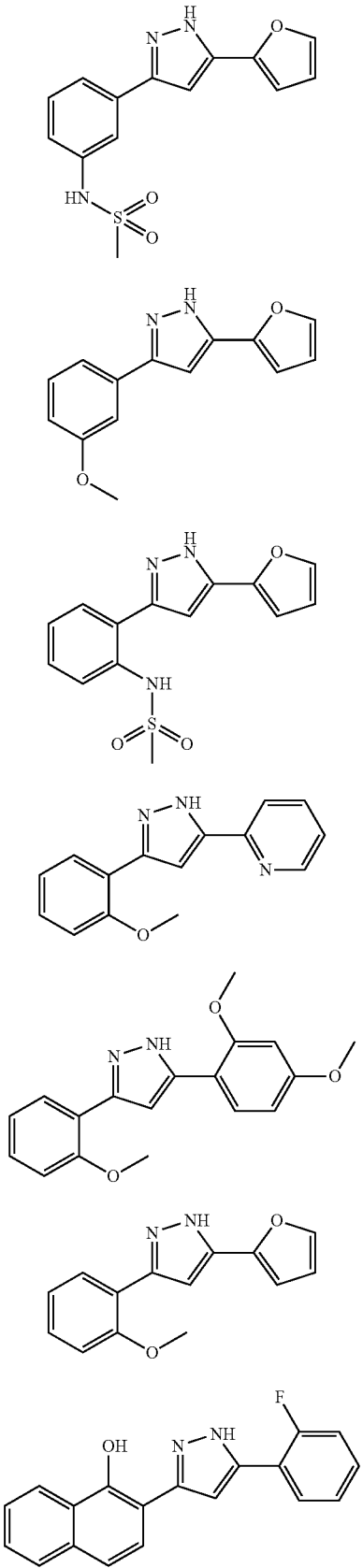
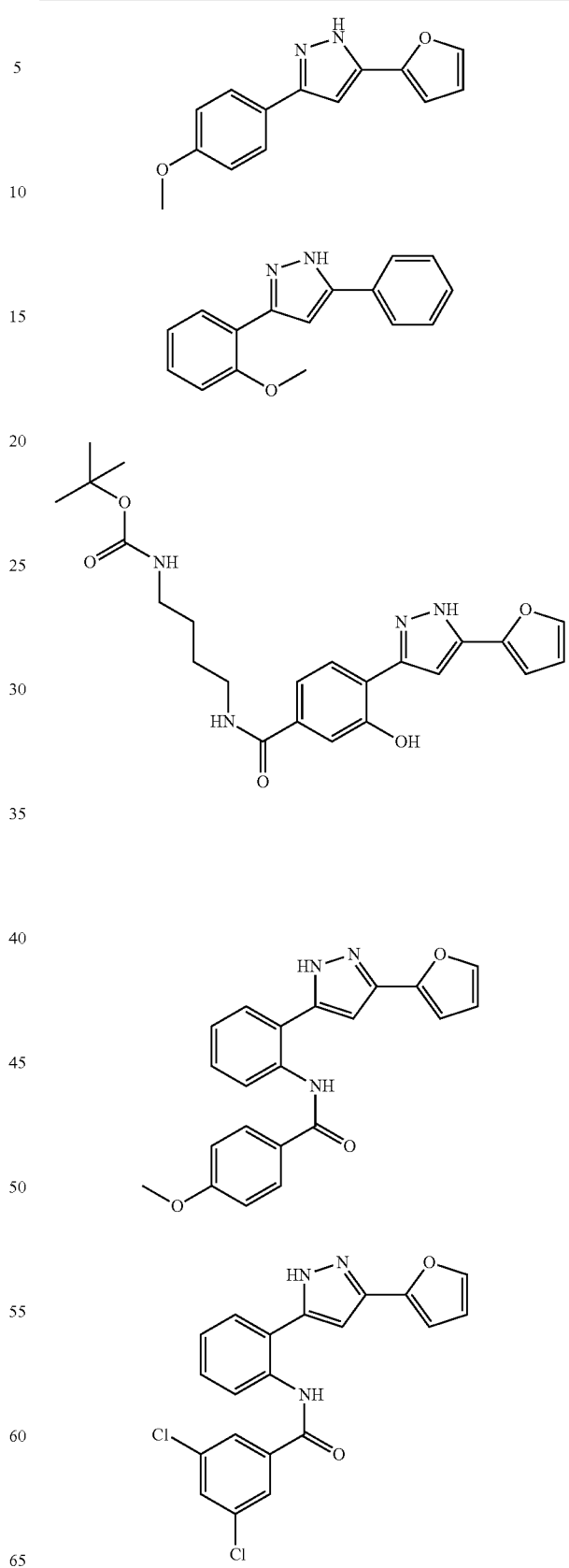

TABLE 1-continued
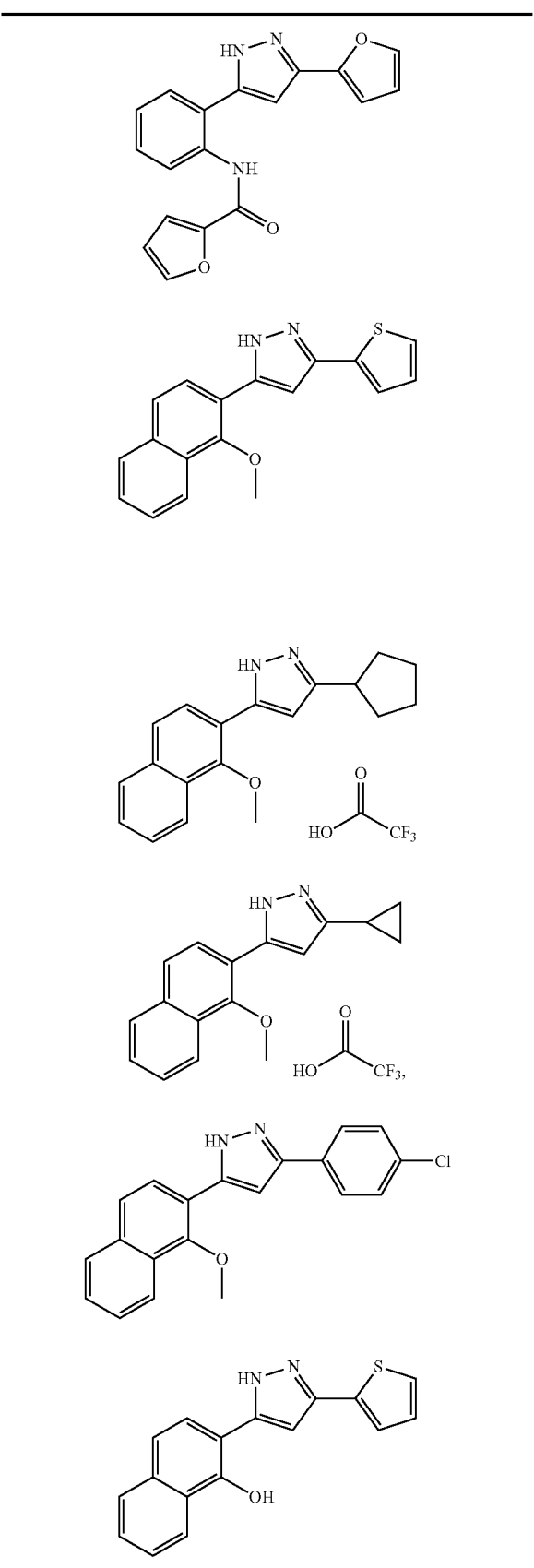
TABLE 1-continued
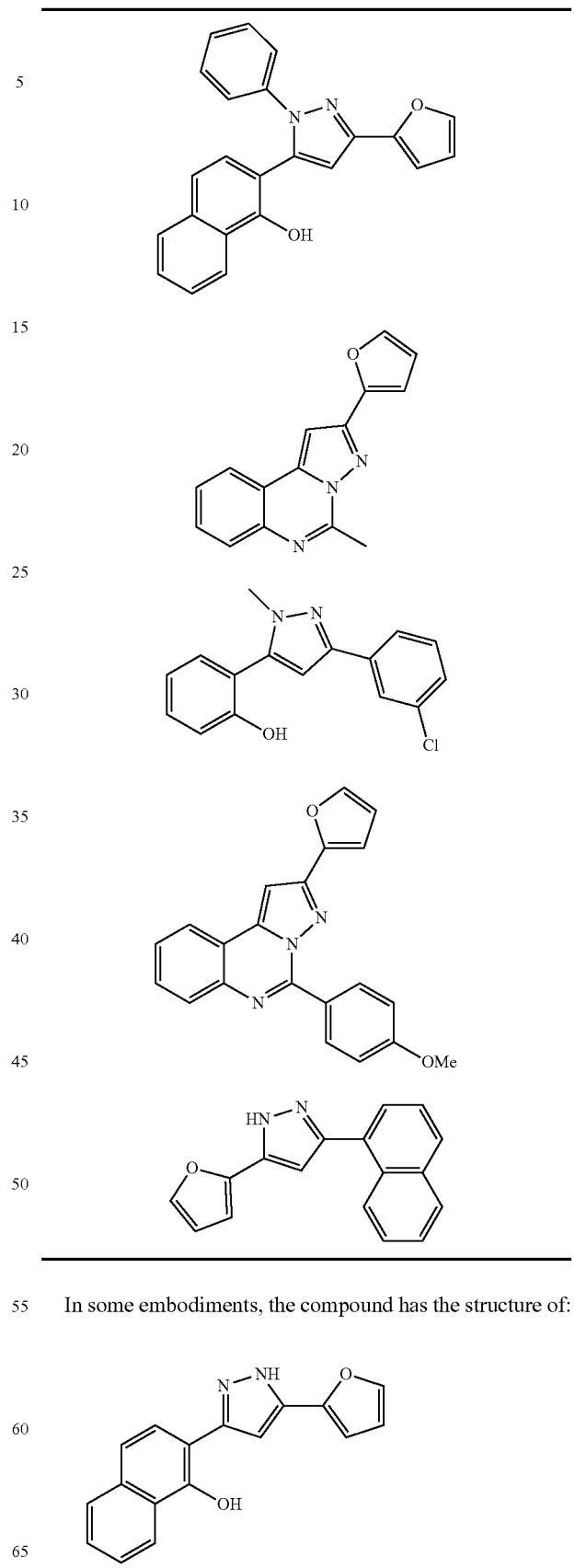
In some embodiments, the compound has the structure of:

In some embodiments, the compound has a structure of

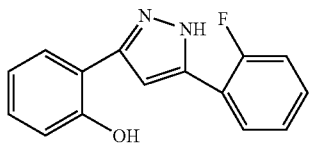 [SMILES: Oc1ccccc1-c1cc(-c2ccccc2F)[nH]n1]

In some embodiments, the compound has the structure of:

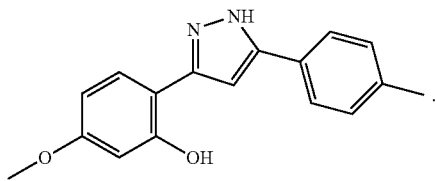

In some embodiments, the compound has the structure of:

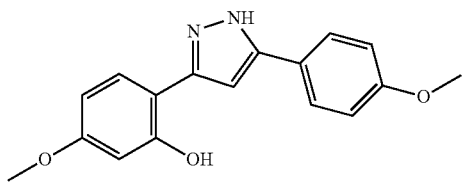

The presently-disclosed subject matter further includes pharmaceutical compositions including a fermentation inhibitor (e.g., compound as described above) and a pharmaceutically-acceptable carrier.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The presently-disclosed subject matter further includes methods for treating a microbial infection in a subject, including administering an effective amount of a fermentation inhibitor to the subject. Compounds and compositions disclosed herein have antimicrobial activity.

As used herein, the term "antimicrobial activity" refers to activity of a compound or composition that inhibits growth of a microbe. The term "microbe" refers to a non-viral pathogen, including all bacterial pathogens.

As used herein, the term "bacterial pathogen" refers to a bacteria capable of causing infection in a subject. In some embodiments, a bacterial pathogen is capable of causing an abscessed tissue. Examples of bacterial pathogens include, but are not limited to, gram positive bacterial pathogens including, *Bacillus anthracis, Enterococcus faecalis, Staphylococcus aureus,* and *Streptococcus pneumonia*; gram negative bacterial pathogens including, *Pseudomonas aeruginosa, Escherichia coli, Salmonella typhimurium,* and *Acinetobacter baumannii.*

The term bacteria or bacterial pathogen further refers to antibiotic-resistant strains of bacterial pathogens, including SCVs. As used herein when referring to a bacterial pathogen, the term "antibiotic-resistant strain" refers to a bacterial pathogen that is capable of withstanding an effect of an antibiotic used in the art to treat the bacterial pathogen (i.e., a non-resistant strain of the bacterial pathogen). For example, *Staphylococcus aureus* can be treated using methicillin; however, an antibiotic-resistant strain of *Staphylococcus aureus* is methicillin-resistant *Staphylococcus aureus* (MRSA).

As used herein, the terms "treatment" or "treating" relate to any treatment of a microbial infection including therapeutic, (i.e., post-infection), and prophylactic treatment, (i.e., pre-infection). As such, the terms treatment or treating include, but are not limited to: preventing a microbial infection or the development of a microbial infection; inhibiting the progression of a microbial infection; arresting or preventing the development of a microbial infection; reducing the severity of a microbial infection; ameliorating or relieving symptoms associated with a microbial infection; causing a regression of a microbial infection or an abscess or one or more of the symptoms associated with a microbial infection; and/or reducing the viability, infectivity and/or virulence of the bacteria. In some cases, in addition to making use of the methods described herein, it can be desirable to make use of traditional and other known treatment protocols. Although such traditional and other known treatment protocols will not be described in any detail herein, they will be known and understood by those skilled in the art, and it is contemplated that such traditional and other known treatment protocols can be used in combination with the methods and compositions described herein, if desired.

As used herein, the term "subject" refers to humans, and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "ring" includes ring systems. For example, "ring" includes phenyl and napthyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "acetamide" as used herein is represented by a formula $A^1$-NH—CO-$A^1$, or $A^1$-NH—CO-$A^1$-NH—CO-$A^1$, where $A^1$ is hydrogen or optionally substituted alkyl, cycloalkyl, alkenyl, cycloalkenyl, alkynyl, cycloalkynyl, aryl, or heteroaryl group as described herein.

The term "amino sulfonyl" as used herein is represented by a formula $A^1$-NH—$SO_2$-$A^1$, where $A^1$ is hydrogen or optionally substituted alkyl, cycloalkyl, alkenyl, cycloalkenyl, alkynyl, cycloalkynyl, aryl, or heteroaryl group as described herein.

In accordance with the methods of the presently-disclosed subject matter, a fermentation inhibitor can be administered to treat the microbal infection of a subject. In some embodiments, the fermentation inhibitor is a compound as disclosed hereinabove, including a compound as set forth in Table 1. In some embodiments, the fermentation inhibitor is a compound having the structure of Formula (I):

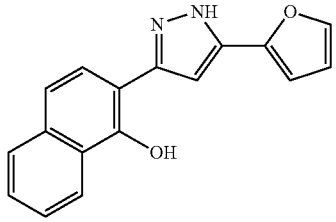

Formula (I)

which is also referred to herein as VU0038882, '8882, or '882.

In some embodiments, methods of the presently-disclosed subject matter include administration of a fermentation inhibitor, as described herein, and administration of an antimicrobial. Without wishing to be bound by theory or mechanism, it is contemplated that the compounds and pharmaceutical compositions described herein have activity against bacteria relying on fermentation. For example, bacteria may rely on fermentation if it is growing in fermentative conditions, e.g., in a part of a subject having little or no available oxygen, or if it wholly relies on fermentation, e.g., in the case of a SCV unable to use respiration. Such SCVs may be resistant to certain traditional antibiotics. Indeed, the use of such traditional antibiotics can lead to the selection of such sub-populations of SCVs that wholly rely on fermentation. In this regard, it is proposed herein that, in some embodiments, a fermentation inhibitor (as disclosed herein) is administered together with an antimicrobial. In some embodiments, the antimicrobial activity of the fermentation inhibitor will be directed towards fermenting bacteria of a bacterial infection, while the antimicrobial activity of the antibiotic will be directed towards respiring bacteria of a bacterial infection. Without wishing to be bound by theory or mechanism, co-administration of a fermentation inhibitor directed towards fermenting bacteria and an antibiotic directed towards respirating bacteria could prevent the selection of a sub-population of SCVs that are highly resistant to antibiotics.

In some embodiments, the co-administered antimicrobial is an antibiotic. In some embodiments, the antibiotic has an intracellular target. In some embodiments, the antibiotic targets aerobically-growing bacteria. In some embodiments, the antibiotic is an aminoglycoside. In some embodiments, the antibiotic is selected from the following:

Ample Spectrum Penicillins
Amoxicillin
Ampicillin
Bacampicillin
Carbenicillin Indanyl
Mezlocillin
Piperacillin*
Ticarcillin
Penicillins and Beta Lactamase Inhibitors
Amoxicillin-Clavulanic Acid
Ampicillin-Sulbactam*
Benzylpenicillin
Cloxacillin
Dicloxacillin
Methicillin
Oxacillin
Penicillin G (Benzathine, Potassium, Procaine)
Penicillin V
Piperacillin+Tazobactam*
Ticarcillin+Clavulanic Acid
Nafcillin
Cephalosporins
Cefadroxil
Cefazolin
Cephalexin
Cephalothin
Caphapirin
Cephradine
Cefaclor
Cefamandol
Cefonicid
Cefotetan
Cefoxitin
Cefprozil
Ceftmetazole
Cefuroxime
Cefuroxime axetil
Loracarbef
Cefdinir
Ceftibuten
Cefoperazone
Cefixime*
Cefotaxime*
Cefpodoxime proxetil
Ceftazidime*
Ceftizoxime*
Ceftriaxone*
Cefepime
Macrolides and Lincosamines
Azithromycin*
Clarithromycin*
Clindamycin
Dirithromycin
Erythromycin
Lincomycin
Troleandomycin Quinolones and Fluoroquinolones
Cinoxacin
Ciprofloxacin*
Enoxacin
Gatifloxacin
Grepafloxacin
Levofloxacin
Lomefloxacin
Moxifloxacin
Nalidixic acid
Norfloxacin*
Ofloxacin
Sparfloxacin
Trovafloxacin
Oxolinic acid
Gemifloxacin
Perfloxacin
Carbepenems
Imipenem-Cilastatin*
Meropenem
Monobactams
Aztreonam*
Aminoglycosides
Amikacin*
Gentamicin
Kanamycin
Neomycin
Netilmicin
Streptomycin
Tobramycin*
Paromomycin
Glycopeptides
Teicoplanin
Vancomycin*
Tetracyclines
Demeclocycline
Doxycycline
Methacycline
Minocycline
Oxytetracycline
Tetracycline
Chlortetracycline
Sulfonamides
Mafenide
Silver Sulfadiazine
Sulfacetamide
Sulfadiazine
Sulfamethoxazole
Sulfasalazine
Sulfisoxazole
Trimethoprim-Sulfamethoxazole
Sulfamethizole
Rifampin
Rifabutin
Rifampin
Rifapentine
Oxazolidonones
Linezolid*
Streptogramins
Quinopristin+Dalfopristin*
Others
Bacitracin
Chloramphenicol*
Colistemetate
Fosfomycin
Isoniazid
Methenamine
Metronidazol
Mupirocin
Nitrofurantoin
Nitrofurazone
Novobiocin
Polymyxin B
Spectinomycin
Trimethoprim
Colistin
Cycloserine
Capreomycin
Ethionamide
Pyrazinamide
Para-aminosalicyclic acid
Erythromycin ethylsuccinate+sulfisoxazole The presently-disclosed subject matter further includes compositions comprising a fermentation inhibitor as described herein, and an antimicrobial, as described herein.

The compounds and compositions as disclosed herein can be locally administered at or near the site of infection (or site associated with a risk of infection). For example, when the microbial infection is associated with the skin of the subject, the fermentation inhibitor can be administered topically (and in combination with a system as disclosed herein, in some embodiments). In some cases, the fermentation inhibitor can be injected into the cite of a microbial infection. Various methods of administrating the fermentation inhibitor can be used, as will be understood by one of ordinary skill in the art.

As used herein, an "effective amount" of the fermentation inhibitor refers to a dosage sufficient to provide treatment for the condition being treated, e.g., an amount sufficient to inhibit growth of the microbe of interest. This can vary depending on the patient, the disease and the treatment being effected. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

Injectable formulations of the metal ion chelator can include various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). Physiologically-acceptable excipients can include, for example, 5% dextrose, 0.9% saline, Ringer's solution or other suitable excipients. A suitable insoluble form of the compound can be prepared and administered as a suspension in an aqueous base or a pharmaceutically-acceptable oil base, such as an ester of a long chain fatty acid, (e.g., ethyl oleate).

The fermentation inhibitor can also be provided in a cream or ointment, or in a transdermal patch for topical administration. A topical ointment formulation can contain the fermentation inhibitor in a carrier such as a pharmaceutical cream base. Various formulations for topical use include drops, tinctures, lotions, creams, solutions, and ointments containing the active ingredient and various supports and vehicles. The optimal percentage of the fermentation inhibitor in each formulation varies according to the formulation itself and the therapeutic effect desired in the specific situation.

The presently-disclosed subject matter further includes a kit for use in treating a microbial infection. In some embodiments, the kit includes a fermentation inhibitor contained in a first vial, and an antimicrobial contained in a second vial.

The kit can further include instructions for administering the fermentation inhibitor and antimicrobial.

In some embodiments, the kit includes a fermentation inhibitor and/or antimicrobial prepared for administration by injection. In this regard, the fermentation inhibitor and/or antimicrobial can be provided in a vial or vials, ready to be combined with an appropriate carrier for use in administering the fermentation inhibitor and/or antimicrobial to the subject. In some embodiments, the fermentation inhibitor and/or antimicrobial is provided in a single-dose vial or vials, containing an amount of the fermentation inhibitor and/or antimicrobial that is an effective amount for use in certain instances, e.g., effective amount for treatment in common instances.

In some embodiments, the kit includes a fermentation inhibitor and/or antimicrobial prepared for topical administration. In this regard, the fermentation inhibitor and/or antimicrobial can be provided in a cream or ointment, or in a transdermal patch.

The presently-disclosed subject matter further includes a system including a device for creating an anaerobic environment adjacent a microbial infection; and a fermentation inhibitor as described herein. For example, the device could comprise a transdermal patch that is substantially impermeable to oxygen. In this regard, for example, bacteria contained within the anaerobic environment created by the patch must rely wholly on fermentation, and would therefore be susceptible to the antimicrobial activity of the fermentation inhibitor. To the extent that the device allows some degree of oxygen to enter the environment, efficacy of the system could be improved by including an antibiotic as described herein.

The presently-disclosed subject matter further includes screening methods, such as those described in the Examples set forth herein. The presently-disclosed subject matter also includes a screening method including: providing a first culture of bacteria and a second culture of bacteria; depriving said cultures of oxygen; contacting the first culture with a known fermentation inhibitor (e.g., as described herein); contacting the second culture with a test compound; and identifying the test compound as a compound useful for inhibiting fermentation if there is a reduction in colonies in the second culture that is the same or less than a reducing in colonies in the first culture.

The presently-disclosed subject matter further includes probes, including a label-modified compound, wherein a compound as described herein is modified with a label. For example, the '8882 compound can be modified with a label.

As used herein, the terms "label" and "labeled" refer to the attachment of a moiety, capable of detection by spectroscopic, radiologic, or other methods, to a molecule. Thus, the terms "label" or "labeled" refer to incorporation or attachment, optionally covalently or non-covalently, of a detectable marker into a molecule, such as a small molecule. Various methods of labeling compounds are known in the art and can be used. Examples of labels include, but are not limited to, the following: radioisotopes, fluorescent labels, heavy atoms, polypeptide labels, chemiluminescent groups, biotinyl groups, and others known to those skilled in the art.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, the following definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Like most bacteria, *S. aureus* requires iron to successfully infect its host. Iron is a cofactor for essential enzymes involved in host defense, DNA replication, and energy production. In humans most iron is found in the form of heme. *S. aureus* preferentially uses host heme as an iron source during infection (72). It does this using the iron-regulated surface determinant (Isd) system to import heme into the cell (79). In the cytoplasm heme can either be used intact as a cofactor or degraded to release free iron. In addition to stealing host heme, *S. aureus* can synthesize heme de novo.

Despite being an essential part of staphylococcal biology, heme is toxic. With reference to FIG. 1, bacterial gene regulation is controlled by a number of signal transduction systems known as two-component regulatory systems (TCS) (1-7). The present inventors identified a novel TCS in many Gram positive pathogens that responds to alterations in available heme, a critical cofactor of bacterial respiratory pathways. This TCS, which was named the heme sensor system (HssS=sensor kinase, HssR=response regulator), activates the expression of a novel transport system upon heme exposure. This TCS is responsible for protecting the bacterial from heme toxicity (38, 22).). HssRS is activated in the presence of heme and up-regulates the heme-regulated transporter (hrtAB) to alleviate heme toxicity. HssRS-mediated activation of HrtAB is required for proper bacterial heme metabolism and respiration (22, 24, 27). The mechanism of heme sensing by HssRS remains to be elucidated.

*S. aureus* is a facultative anaerobe. It can generate energy using a combination of three pathways: 1-aerobic respiration, 2-anaerobic respiration and 3-fermentation. Fermentation is the only respiratory pathway that does not require heme in order to generate energy.

Clinical isolates called small colony variants (SCVs) are often isolated from patients with persistent *S. aureus* infections. These isolates only ferment as they have lesions in pathways critical for respiration, including menaquinone synthesis (ΔmenB) and heme synthesis (ΔhemB). These SCVs are able to evade antibiotic treatment and host defense by eliminating respiration (80).

As described herein, in probing the mechanism of HssRS heme sensing using small molecules, fundamental insights into the integration of the respiratory state of *S. aureus* and heme regulation have been uncovered.

Figure 2A:
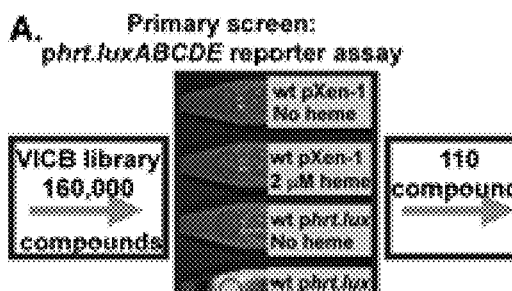
FIGS. 2A-2D include a diagram illustrating an assay used to identify certain compounds as described herein, together with results. Briefly, phrt.lux was used to screen a small molecule library for activators of HssRS in S. aureus. The top hits from the primary screen (FIG. 2A) were confirmed in a secondary screen (FIG. 2B) employing the phrt.xylE reporter construct. The top lead compounds were tested for their ability to pre-adapt S. aureus for heme toxicity (FIG. 2C), and for HssRs activation in B. anthracis, with a top hit ('8882) being identified (FIG. 2D).
Figure 2B:
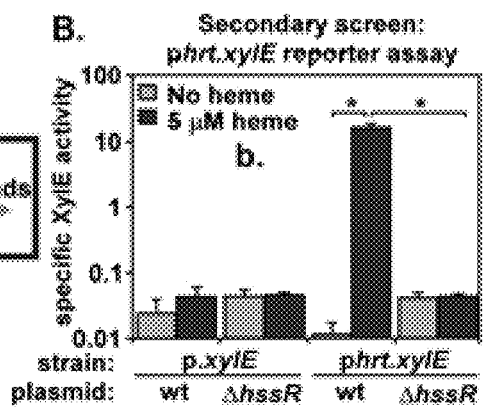
Figure 2C:
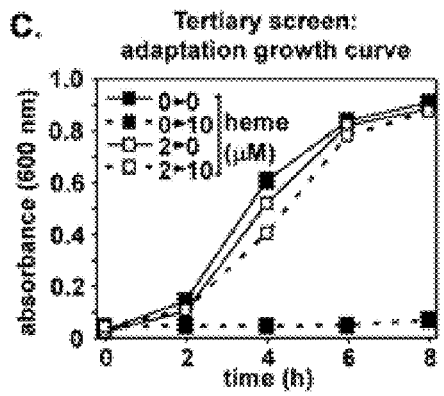
Figure 2D:
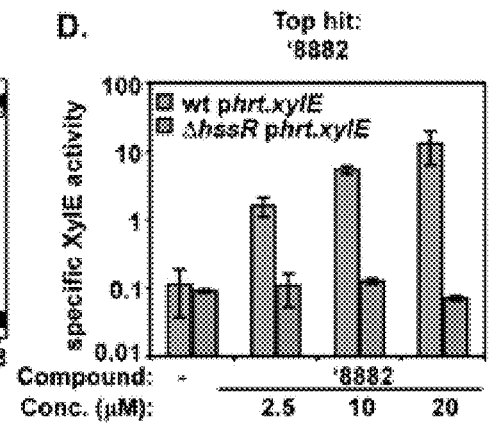

The present inventors designed and conducted a screening assay to identify activators of HssRS. With reference to FIG. 2A, a reporter plasmid containing the luxABCDE operon from *Photorhabdus luminescens* driven by the hrtAB promoter (phrt.lux) was used to screen 160,000 compounds from the VICB small molecule library with luminescence. With reference to FIG. 2B, 110 of the top hits from the primary screen were confirmed in a secondary screen using a xylE reporter gene driven by the hrtAB promoter (phrt.xylE). With reference to FIG. 2C, compounds that activated the hrtAB promoter were further characterized for their ability to pre-adapt *S. aureus* for heme toxicity. Activation of HssRS by a sub-toxic concentration of heme protects *S. aureus* from a subsequent toxic concentration of heme by upregulating HrtAB. The inhibition of growth due to heme toxicity is determined by measuring the optical density of bacterial cultures at 600 nm. In each screen the present inventors identified hits by comparing their activity to that of heme. As an example, each assay performed with heme is shown in FIGS. 2A-C. With reference to FIG. 2D, the compound identified herein as '8882 was found to be the most potent activator of HssRS. Cultures of wildtype and ΔhssR carrying phrt.xylE were assayed for XylE activity upon '8882 treatment. The screening method designed by the present inventors as able to successfully identify small molecule activators of the *S. aureus* heme stress response.

Heme and '882 both trigger HssS signaling through similar amino acid residues despite being structurally distinct (data not shown). This suggests that '882 may activate HssS by inducing endogenous heme synthesis. The combined effect of heme and '882 on HssRS signaling was studied using an hrtAB reporter assay. Heme and '882 were added to *S. aureus* at increasing concentrations and hrtAB driven XylE reporter activity was measured as described (27). These data revealed that '882 and heme act non-competitively (synergistically) to trigger HssRS in a process dependent on endogenous heme biosynthesis.

Figure 3:
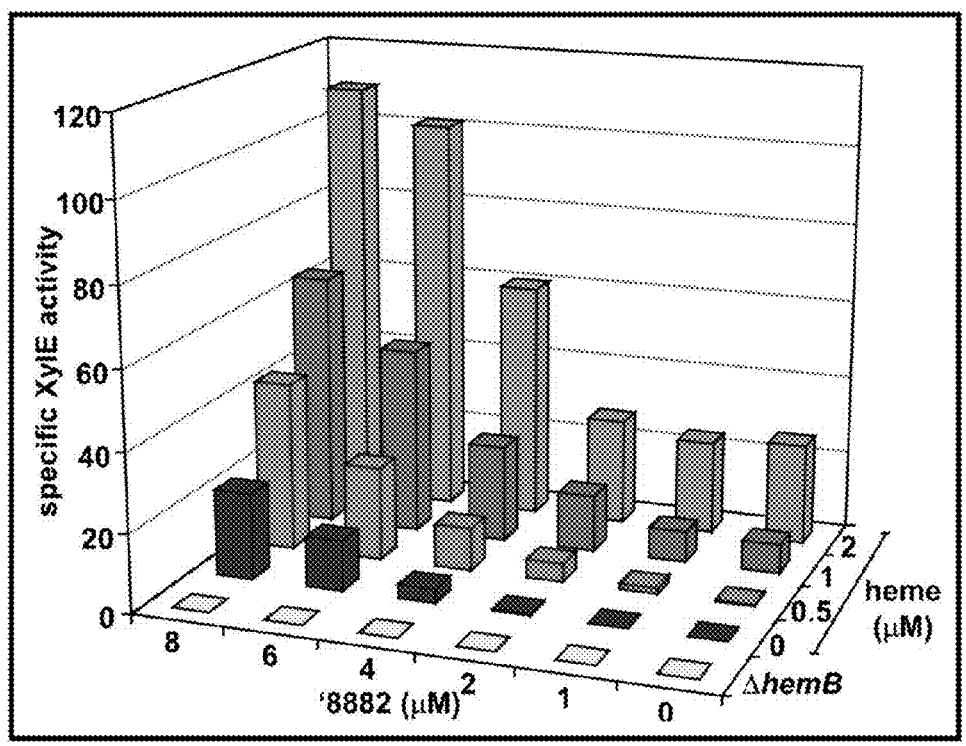
FIG. 3 is a depicts endogenous heme production and XylE activity as a function of '882 concentration. '882 non-competitively activates HssRs through endogenous heme biosynthesis. S. aureus transformed with the phrt.xylE construct was treated with increasing concentrations of heme and '882. S. aureus hemB::ermC (ΔhemB) carrying the phrt.xylE reporter construct was treated with increasing concentrations of '882. XylE activity was measured in cell lysates and normalized to lysate protein concentration.

To test whether or not heme synthesis is required for '882-dependent HssS signaling, the impact of '882 on *S. aureus* ΔhemB mutants that are unable to synthesize heme was evaluated. With reference to FIG. 3, *S. aureus* wildtype and the heme auxotroph hemB::ermC (ΔhemB) carrying phrt.xylE were grown to stationary phase in media containing the indicated concentrations of '8882 (y-axis) and heme (x-axis). Cell lysates were assayed for XylE activity and normalized to lysate protein concentration. '8882 was found to activate HssRS in a manner that requires endogenous heme biosynthesis and does not compete with exogenous heme.

To directly test if '882 exposure increases heme levels within staphylococci, intracellular heme abundance was measured using two distinct approaches. First, intracellular heme levels were quantified using a commercially available heme quantification kit (BioAssay systems). These results revealed that *S. aureus* strains grown in the presence of '882 contain approximately 10% more intracellular heme than non-exposed bacteria (data not shown).

Figure 4A:
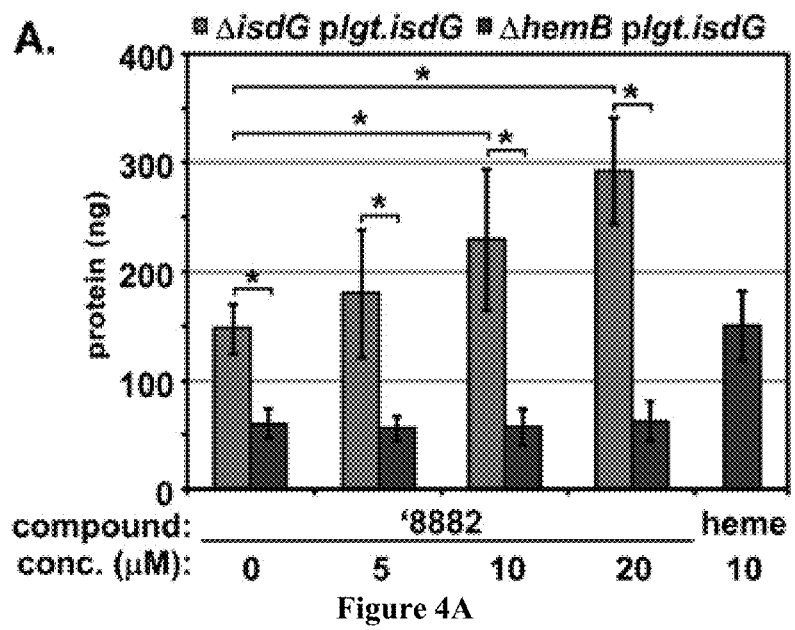
FIGS. 4A and 4B include the results of further studies showing the relationship between compounds, compositions, and methods of the presently-disclosed subject matter and heme production. Wild type and ΔhemV S. aureus transformed with isdG driven under the constitutive lgt promoter (plgt.isdG) were grown in the presence of increasing concentrations of '8882. Whole cell lysates, along with a protein standard, were blotted with anti IsdG polyclonal antisera and IsdG levels were quantified by densitometry.
Figure 4B:
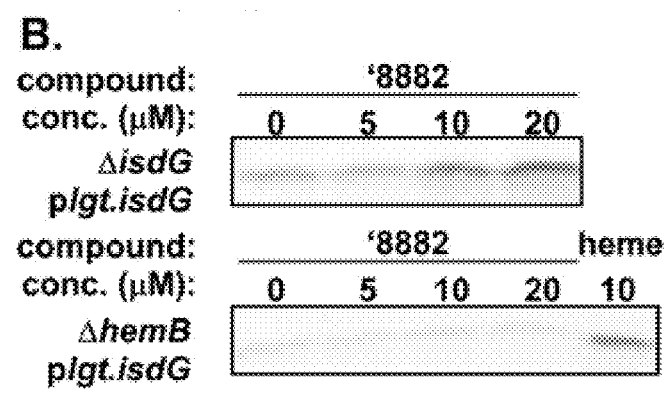
Figure 5:
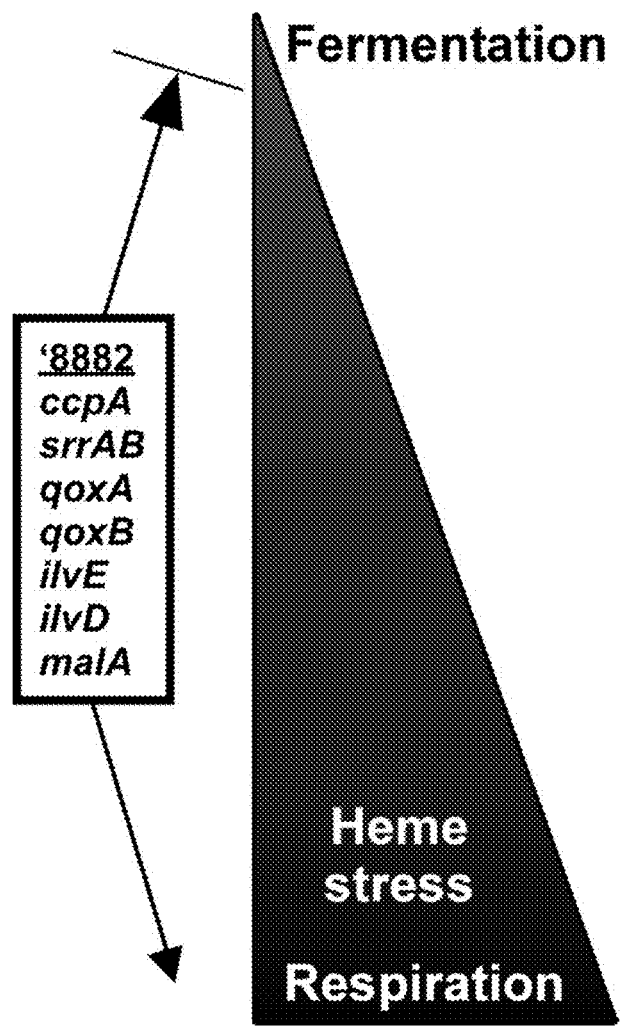
FIG. 5 depicts the modulatory relationship between an exemplary compound of the presently-disclosed subject matter, '8882, and bacterial respiration.

Second, the intracellular abundance of the heme stabilized protein IsdG was used as a barometer of functional cytoplasmic heme levels (43), i.e., IsdG is a heme stabilized protein that can be used as a reporter for intracellular heme levels. With reference to FIG. 4A, *S. aureus* ΔisdG and ΔhemB were transformed with a plasmid that constitutively expresses IsdG (plgt.isdG). These strains were grown to stationary phase in the presence of the indicated concentration of '8882 or heme. Whole cell lysates were immunoblotted with anti-IsdG polyclonal antisera and bands were quantified using densitometry. FIG. 4B includes representative blots of the ΔisdG (top) and ΔhemB (bottom) data shown in FIG. 4A. * indicates a p-value of <0.05. The results demonstrated that '882 increases the abundance of IsdG in a concentration-dependent fashion, exceeding the stabilizing effect observed upon addition of heme or heme precursors. In addition, the stabilization of IsdG by '882 requires endogenous heme biosynthesis. That is to say, '8882 increases intracellular levels of heme in a process dependent on endogenous heme biosynthesis.

'882 triggers HssS by activating the heme biosynthetic machinery (FIGS. 2 and 4). Heme synthesis must be a tightly regulated process since overproduction of heme is predicted to increase respiration and cause cellular toxicity. Consistent with this, '882 exposure delays the shift of stationary phase cultures of *S. aureus* into fermentative growth as measured by reduced glucose consumption and delayed production of the fermentative end product lactate (data not shown). The present inventors contemplate that '882-mediated activation of respiratory pathways should be toxic to *S. aureus* grown in conditions that require fermentative growth. *S. aureus* was grown in the absence of oxygen or other suitable electron donors, a growth condition that necessitates fermentation. In these conditions, '882 halts *S. aureus* growth at concentrations less than 5 μM. These results (i) underscore the value of '882 as a modulator of heme synthesis, (ii) reinforce the supposition that small molecule manipulation of central metabolism can profoundly impact bacterial physiology, (iii) establish heme synthesis and respiration as pathways that can be targeted for antibacterial development, and (iv) set the stage for determining the impact of altered heme synthesis on bacterial respiration.

A transposon library of *S. aureus* was screened to identify mutants that no longer sense '8882 by growth curve analyses as shown in FIG. 2C. Transposon insertion sites were identified by inverse PCR. Several mutants were found to have insertions in genes involved in *S. aureus* respiration. Transposon mutagenesis suggests that '8882 modulates the respiratory state of the cell to affect HssRS signaling.

Figure 6A:
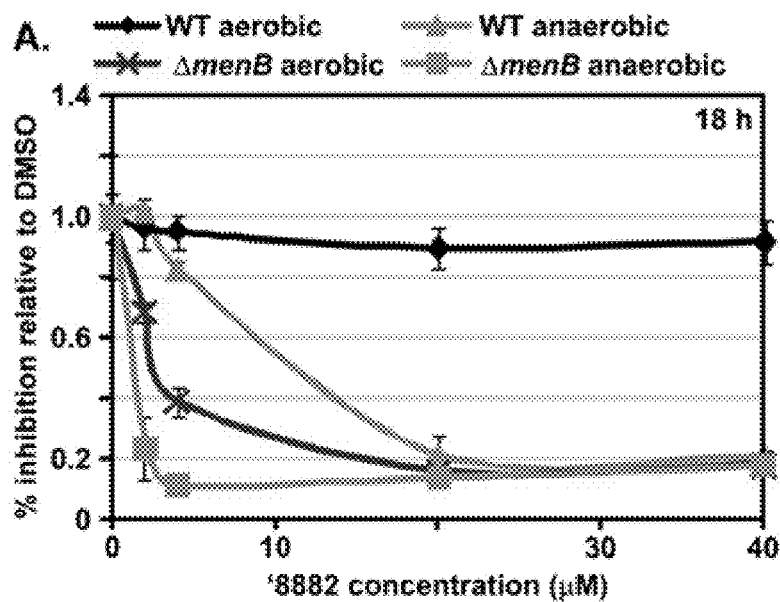
FIGS. 6A and 6B include data illustrating the effect of an exemplary compound of the presently-disclosed subject matter, '8882, on bacteria in aerobic and anaerobic environments.
Figure 6B:
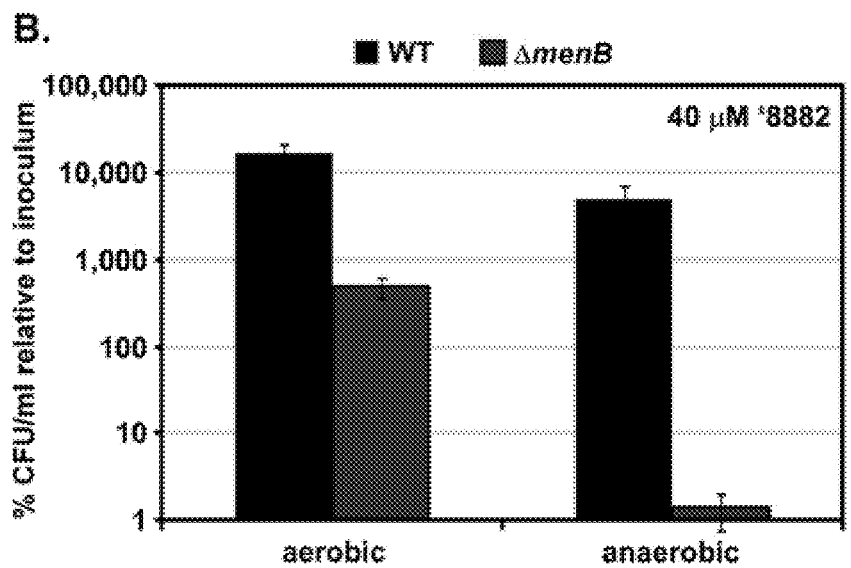

With reference to FIGS. 6A and 6B, '8882 was found to inhibit *S. aureus* fermentative growth. *S. aureus* Newman and respiration defective ΔmenB were grown to stationary phase in increasing concentrations of '8882. Cultures were either incubated under aerobic or anaerobic conditions for 18 h. Growth was normalized to vehicle treated bacteria. As shown in FIG. 6B, colony forming units (CFU) were enumerated for both the input and output of bacteria treated with 40 uM '8882 in FIG. 6A to determine if '8882 is bacteriostatic or bacteriocidal. It was found that '8882 is bacteriostatic to fermentatively growing staphylococci.

Figure 7A:
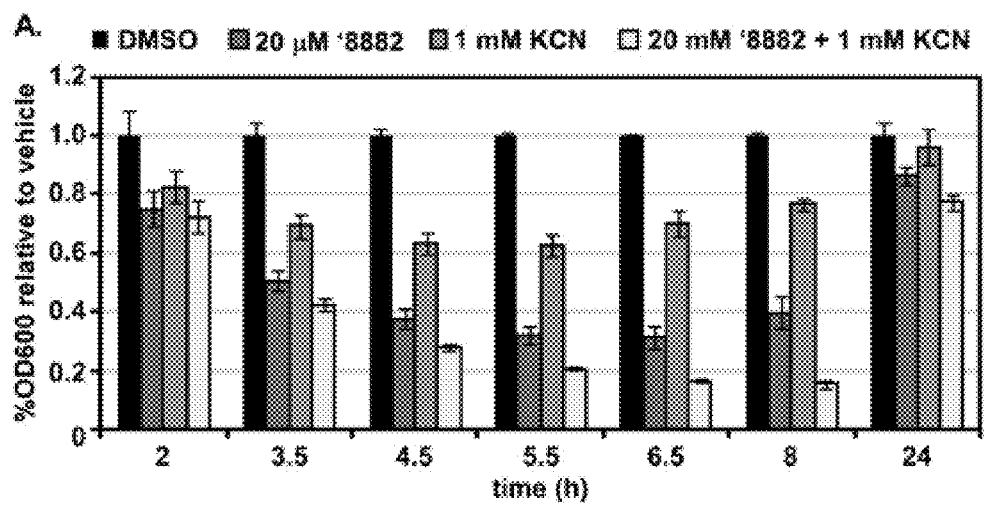
FIGS. 7A-7D include further data showing the fermentation inhibition activity of an exemplary compound of the presently-disclosed subject matter, '8882.
Figure 7B:
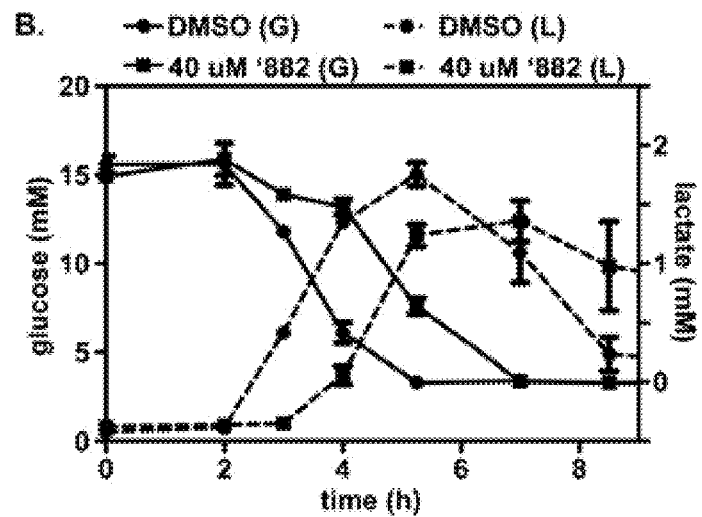
Figure 7C:
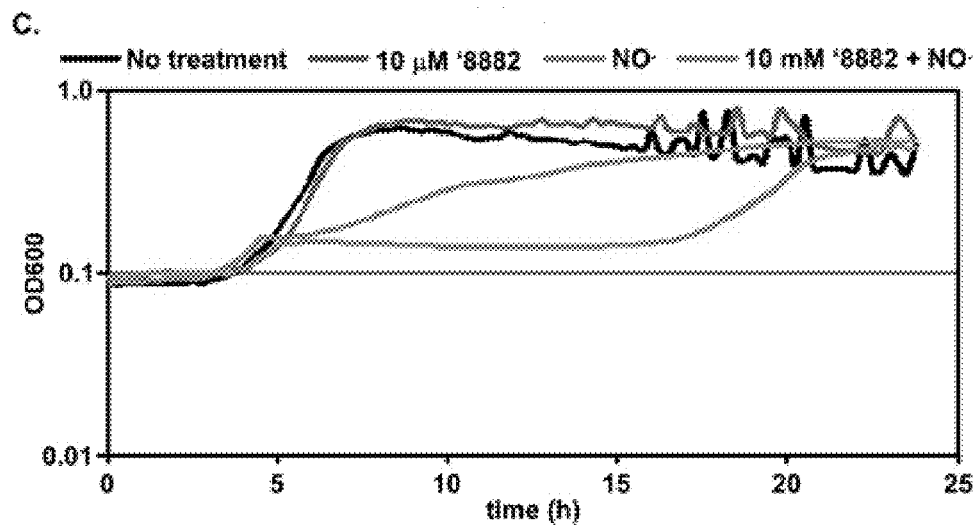
Figure 7D:

The effects of '8882 on fermentation was studied. With reference to FIG. 7A, *S. aureus* was grown in the presence of the indicated concentration of '8882 or cyanide. Growth was monitored over time by measuring the optical density at 600 nm and normalized to vehicle treated *S. aureus*. With reference to FIG. 7B, the concentration of glucose and lactate was measured in supernatants collected from *S. aureus* cultures containing vehicle or '8882. With reference to FIG. 7C, *S. aureus* grown in the presence or absence of '8882 was subjected to nitric oxide stress after 5 hours of growth. With reference to FIG. 7D, *S. aureus* was incubated with murine neutrophils in media containing either vehicle or '8882. Bacterial viability was determined by enumerating colony forming units on solid media. These data indicate that '8882 reduces the ability of *S. aureus* to ferment which increases its susceptibility to NO stress and neutrophil killing.

Figure 8A:
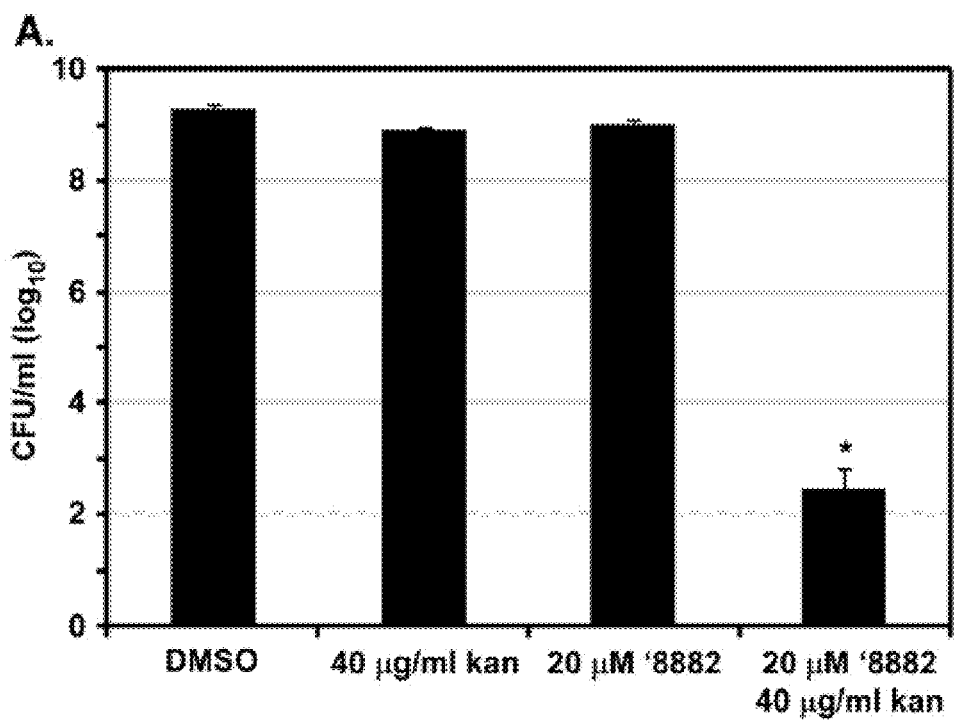
FIGS. 8A and 8B include data showing antibiotic efficacy of an exemplary compound of the presently-disclosed subject matter, '8882, and the antibiotic, kanamycin, alone and in combination.
Figure 8B:
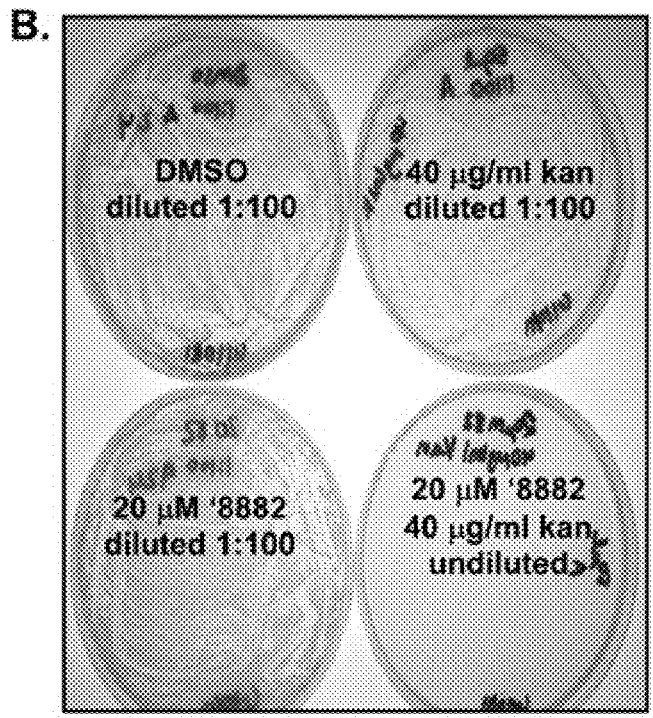

With reference to FIG. 8A, *S. aureus* Newman was cultured in TSB containing the indicated amount of kanamycin or '8882. After 24 h colony forming units (CFUs) were enumerated on solid medium. The dashed line indicates the limit of detection (LOD) and the asterisk denotes that two of the three replicates were below the LOD. Turning to FIG. 8B, 50 ul of each experimental groups was plated on TSA at a dilution of 1:100 except for the co-treatment group, which was plated undiluted. Two of the three co-treated replicates had no viable colonies. These data indicate that co-treatment of *S. aureus* with '8882 and kanamycin improves antibiotic efficacy in vitro.

The studies described herein support the utility of the compounds, compositions, and methods disclosed herein. '8882 was found to be a potent small molecule activator of the heme sensor system HssRS. '8882 mediated activation of HssRS requires endogenous heme biosynthesis. '8882 increases intracellular levels of endogenous heme. HssRS can sense both exogenous and endogenous heme stress. Genes involved in cellular respiration contribute to the ability of '8882 to activate HssRS suggesting that the respiratory state of bacterial cells affects HssRS activity. Fermentatively-grown wild type *S. aureus* and a mutant unable to aerobically respire have heightened sensitivity to '8882 toxicity. '8882 inhibits *S. aureus* fermentation. '8882 treatment potentiates the bacteriocidal effects of neutrophils and kanamycin. *S. aureus* relies on fermentation to evade neutrophil and antibiotic mediated killing. '8882 has therapeutic potential to improve bacterial clearance by both the host immune system and antibiotic treatment. The respiratory state of *S. aureus* and its intracellular heme status are intricately linked.

Example 2

The structure, purity, and heme-activating properties of '882 were verified following its resynthesis by way of a five-step reaction sequence starting from commercially available 1-hydroxy-2-naphthaldehyde (44).

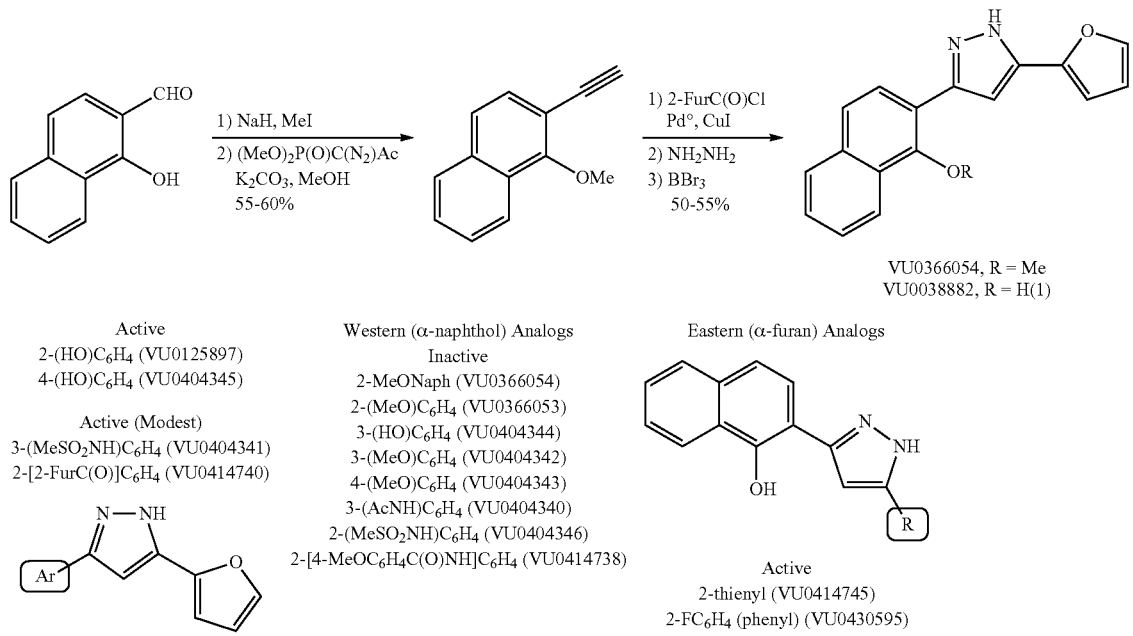

-continued
Novel Analogs

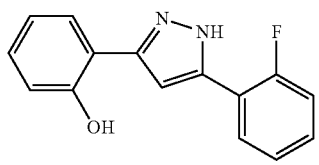

VU0163139 (Active)

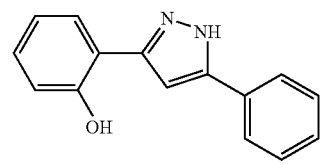

VU0020191 (Active)

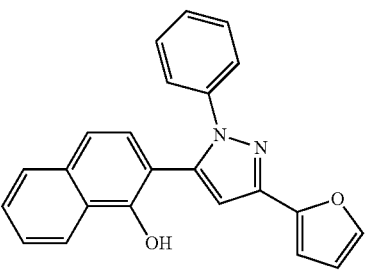

VU04409029 (Active)

Synthesis and Relative HssRS Activation of Analogues '8882(1)

Both purchased and resynthesized '882 equally maintain HssRS activation. Moreover, the free base of '882 and its corresponding trifluoroacetate salt demonstrate good chemical stability, have no rule of five violations, and exhibit good solubility in DMSO and aqueous solution (45). Using an iterative medicinal chemistry approach, preliminary structure activity relationship (SAR) data has been collected (summarized above). The identification of positions around the '882 scaffold that tolerate structural modification is useful in the development of an affinity-probe derived from '882.

Analogs of '882 were divided into two classes, and chemical modifications of both the Western-naphthol ring and the Eastern-furan ring were conducted. Each set was screened against the XylE assay with heme and '882 as standards for comparison. Analogs were classified qualitatively as inactive, active (comparable to '882) and modestly active in order to assist with probe design. Examples of synthesized compounds and their activity classifications are shown above.

From initial chemistry around the Western half, it was determined that a hydroxyl group (or equivalent) in the 2- or 4-position is required to maintain heme sensing activation and that the fused naphthalene ring system can be reduced to a phenyl ring without significant loss of activity. Chemical modification of the Eastern half of '882 revealed that replacement of the metabolically labile furan ring with a 2-thienyl (VU0430595) or, more significantly, a 2-fluorophenyl (VU0430595) did not lead to loss of heme activation. Our cumulative SAR studies led us to prepare combined Western and Eastern modified analogs of '882 in the form of VU0163139 and VU0020191. Both novel analogues exhibited HssRS activation comparable to '882 (data not shown). Recently, the N-phenyl analog, VU0449029, was prepared and determined to maintain heme sensing activity. This result suggests a free —NH in the central core is not required, and replacement of the pyrazole ring with other heterocycles such as oxazole, oxadiazole or imidazole may be tolerated. These SAR data provide a foundation necessary for creating small molecule affinity probes of '882.

Example 3 (Prophetic, in Part)—Sensor Probe Based on an '882 Scaffold

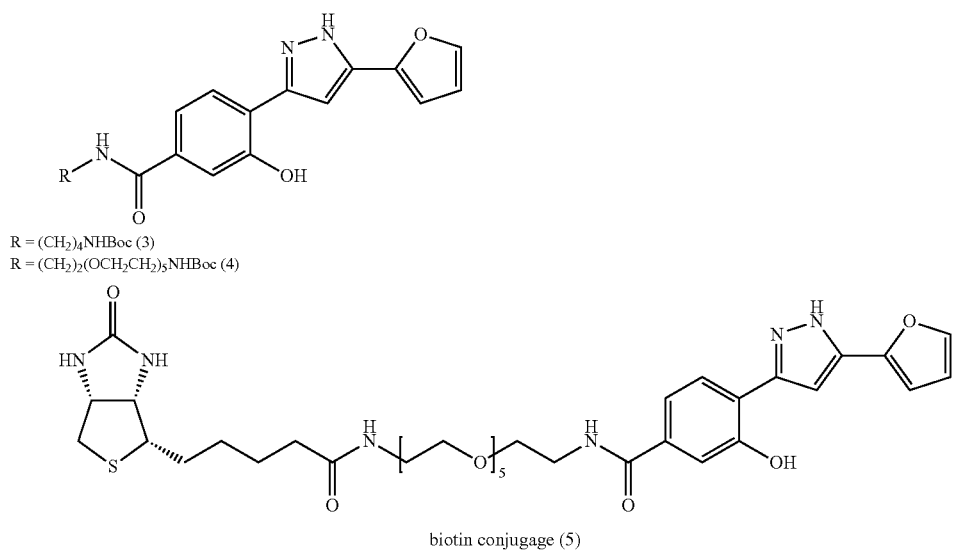

Based on the SAR data of '882, the present inventors propose the design of chemical probes for the purpose of target identification. Probes are prepared and examined in the context of affinity chromatography and photoaffinty labeling strategies (48-50). The former approach will rely on streptavidin chromatography in conjunction with immobilization of the biotin conjugate 5. Boc-protected pyrazole 3 have been prepared and it has been determined that 3 activates HssRS as measured by XylE assay. The present inventors are now working toward PEG-linked Boc-protected amine 4. Treatment of 4 with trifluoroacetic acid, followed by condensation with biotin will afford conjugate 5 ready for affinity chromatography experiments.

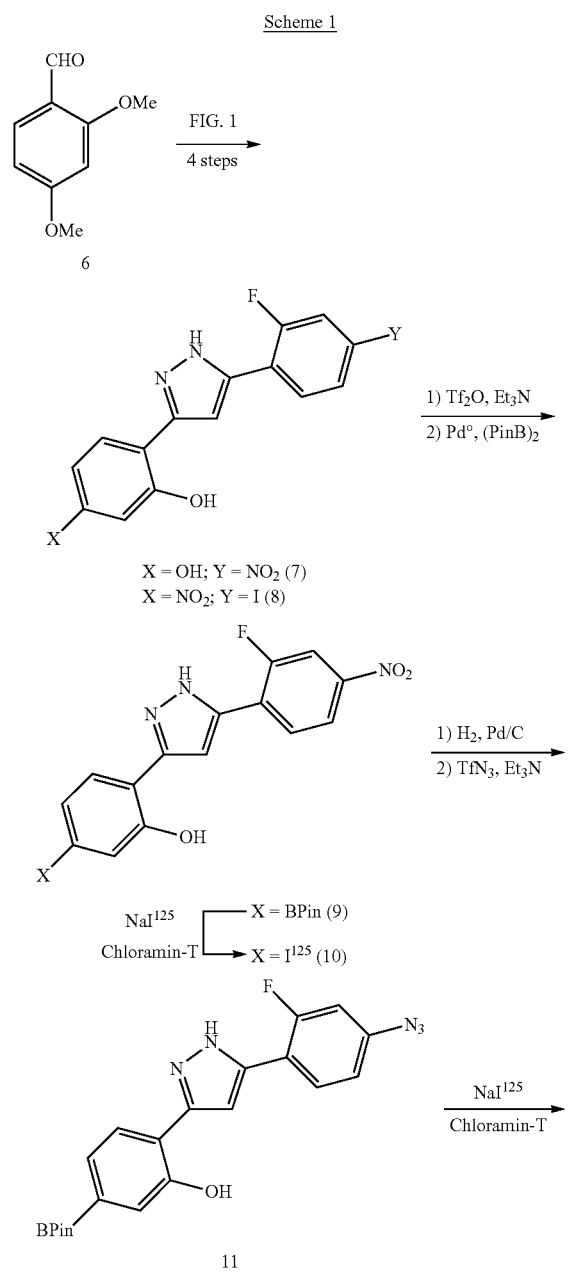

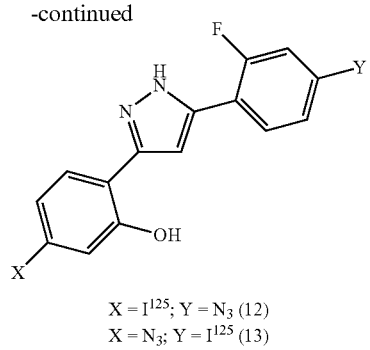

X = I¹²⁵; Y = N₃ (12)
X = N₃; Y = I¹²⁵ (13)

In addition to affinity chromatography a series of photoaffinity probes will be designed, prepared, and evaluated (51). Key elements of photoaffinity ligand (PAL) design are selection of a photoreactive group (e.g., aryl azide, benzophenone or diazirine) (52) and label (e.g. radio, biotin, or fluorescent label) (48) to assist in the isolation and identification of the small molecule target. Relevant to the success of PAL experiments will be preservation of heme activation of the '882-derived PAL probe. Minimal perturbation of structure and preservation of heme activation can be achieved by using an aryl azide group as the photoreactive moiety and radiolabeling as the tagging component. To this end, in Scheme 1 the chemical synthesis of aryl azide 12 starting from resorcinol 6 is proposed. Pyrazole 7 will be prepared following the developed four-step reaction sequence described above (Synthesis and relative HssRS activation of analogues '8882). Selective triflation of the more reactive p-phenol will provide the corresponding triflate and upon cross-coupling with PinBBPin (53), will yield boronate 9. Hydrogenation of the nitro group to the corresponding amine and diazo transfer (54) will yield aryl azide 10. Finally, the boronate group will be substituted for ¹²⁵I by oxidation of NaI¹²⁵ (53, 55). The final radiochemical reaction will be conducted in the Department of Radiology and Radiological Sciences at Vanderbilt University.

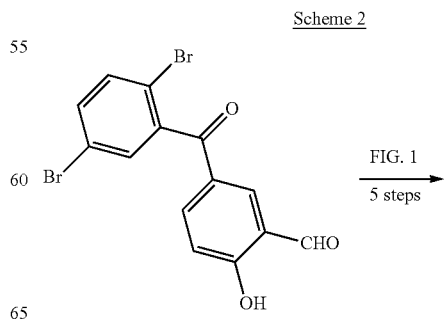

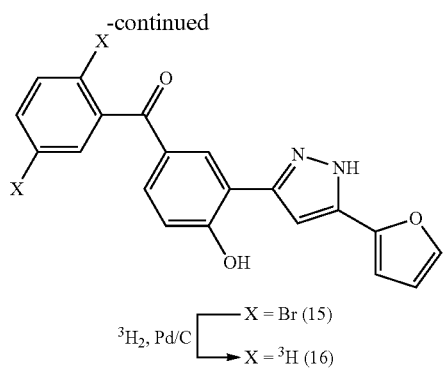

Minor modification of the chemical synthesis shown in Scheme 1 will provide access to two additional PAL probe candidates, m-fluoronitrobenzene 10 and aryl azide 13. Once again, radiolabeled 10 will be derived by oxidation-mediated electrophilic substitution of boronate 9. Meta substituted nitrobenzenes such as m-fluoronitrobenzene 10 have been long used as PAL probes (52) based on their propensity to undergo photosubstitution by nucleophilic amines. The second PAL probe candidate, aryl azide 13 will be prepared by way of pyrazole 8 (X=NO$_2$ and Y=I) obtained by appropriate modification of the four-step reaction sequence shown in FIG. 3.

In concert with the preparation and study of PAL probes 10, 12, and 13, the present inventors will conduct a synthesis of tritium-labeled pyrazole 16 as a fourth PAL probe (Scheme 2). In contrast to aryl azides 12 and 13, pyrazole 16 preserves the furan heterocycle of '882 with the naphthalene ring of '882 replaced with a photoreactive tritium-labeled benzophenone (56-57). The proposed synthesis of benzophenone 13 starts from aldehyde 14 available from anisole following a Friedel-Craft acylation and Riemer-Teimann reaction (58). Incorporation of tritium will be accomplished by hydrogenolysis of the dibromobenzophenone 15 employing tritium gas under predetermined reaction conditions (56). In this case, the radiochemical hydrogenation will be conducted by American Radiolabeled Chemicals. The tritium-labeled product (16) will be delivered for subsequent photoaffinity experiments. If photoaffinity experiments using radiolabeled 16 prove encouraging, a per-deuteriated analogue of benzophenone 16 will be prepared starting from [D$_5$]-anisole and [D$_5$]-benzoyl chloride leading to [D$_8$]-16. Employing a 1:1 mixture of [D$_8$]-16 and unlabeled [D$_0$]-16 in the photoaffinity experiment will assist in protein identification by mass spectrometry in the Mass Spectrometry Research Center (MSRC) at Vanderbilt, as a unique isotopic signature of labeled protein will be observed (59-60).

Example 4 (Prophetic, in Part)—Identification of Subcellular Target of '882 Through the Use of Sensor Probes It is contemplated that '882 activates HssRS signaling by inducing endogenous heme synthesis within *S. aureus*. Sensor probes based on the '882 scaffold will be employed to identify the target of the small molecule. '882 probes developed in Example 3 will be added to cultures of *S. aureus* harboring vectors containing luciferase under the control of the hrtAB promoter as described herein. Bacterial cultures will be incubated overnight using growth conditions similar to those described in Example 1. The following day, luminescence will be measured to ensure hrtAB activation, and bacteria will be lysed using standard procedures. Bacterial lysates will then be added to a streptavidin column to capture molecules bound by biotin-conjugated '882. After a series of wash steps, bound proteins will be eluted and identified using tandem mass spectrometry in conjunction with the MSRC. In a parallel series of experiments, bacterial lysates will be subjected to SDS-PAGE to identify bands bound to the radioactive PAL derivatives of '882. Treatment with the '882 probe in the presence of excess '882 or an inactive analog will be used to verify binding specificity in these experiments. To confirm that proteins identified in this analysis are required for '882-dependent HssS activation, the genes encoding these proteins will be inactivated using standard allelic replacement strategies (61). Next, reporter constructs containing phrtAB.xylE will be transformed into mutant strains, and the ability of '882 to trigger hrtAB activation will be monitored.

In parallel with this chemical approach, a genetic approach to identify the targets of '882 will also be taken. For these experiments, an *S. aureus* transposon mutant library will be exploited. This library will be screened using a heme adaptation assay (22) to identify mutants that can no longer sense '882 and adapt to heme stress. The phenotype of the hits in the primary screen will be confirmed by XylE assay. In this way, genes required for '882-dependent HssRS activation will be identified and focus attention on potential '882 targets. Concurrent with these experiments, candidate proteins of interest will be purified for binding studies using Octet bio-layer interferometry (ForteBio) to calculate association and dissociation rates and confirm a direct interaction with '882 (62).

The completion of these studies will result in the identification of the protein targets of '882 within *S. aureus*. Based on the significant antimicrobial activity of '882 against *S. aureus*, these proteins may represent targets for inhibition in subsequent screening strategies. Moreover, in keeping with the proposed role of '882 as an activator of endogenous heme synthesis, the protein targets of '882 have the potential to elucidate the regulatory pathways governing heme synthesis in bacterial pathogens.

Example 5 (Prophetic, in Part)—Impact of '882 on the Heme Biosynthetic Machinery It is contemplated that '882 induces endogenous heme production by increasing the transcription, translation and/or abundance of the heme biosynthetic machinery. Genomic and proteomic experiments are contemplated. The staphylococcal heme biosynthetic machinery is comprised of eleven proteins encoded within four separate transcriptional units named hemAXCDBL, hemEHY, hemN and hemZ (64). To test if '882 exposure induces transcription of any of these genes, real-time polymerase chain reaction (RT-PCR) experiments will be conducted focusing on each of these four cistrons. *S. aureus* will be grown in the presence and absence of optimized '882 analogs and the impact of these compounds on hemAXCDBL hemEHY, hemN and hemZ transcription will be measured. Inactive analogs will serve as a negative control. This experiment will determine if '882 increases heme abundance by activating transcription of the genes required for heme synthesis. If the molecules are found to activate the transcription of any of the genes involved in heme synthesis, this result would suggest that '882 mediates its activity by impacting an as-yet-unidentified transcription factor. It is contemplated that such a transcription factor would be identified by the pull-down experiments or genetic screen described above.

It is conceivable that the effect of '882 on heme levels is mediated through post-transcriptional changes in protein abundance. To determine the levels of HemA, HemX, HemC, HemD, HemB, HemL, HemE, HemH, HemY, HemN and HemZ, quantitative proteomic analysis using spectral counting will be applied. This technique has been used successfully by the present inventors to determine the impact of environmental changes on protein abundance within bacterial cells (65-66). Briefly, staphylococcal cultures will be grown in the presence and absence of '882 or an inactive analog. Following incubation, cytoplasmic fractions will be isolated and subjected to LC-MS/MS-based protein identification in conjunction with the MSRC. The abundance of each protein involved in heme synthesis will be compared in the presence and absence of '882. The results of these experiments will reveal if '882 exposure alters the abundance of individual components of the heme biosynthetic machinery.

Finally, to identify the specific step within heme synthesis that is affected by '882, the amounts of the individual precursors of heme that accumulate upon '882 exposure will be determined. If '882 is acting at a distinct step in the heme synthesis pathway, it is contemplated that exposure to the compound will result in the accumulation of an intermediate within this pathway. As a direct test, the amounts of all of the heme biosynthetic intermediates will be measure, including glutamate, glutamyl-tRNA, glutamate 1-semialdehyde, δ-aminolevulenic acid, porphobilinogen, hydroxymethyl bilane, uroporphyrinogen III, coproporphyrinogen III, protoporphyrinogen III, and protoporphyrin IX. Heme metabolites will be extracted from $S.$ $aureus$ exposed to '882 or an inactive analog control using established protocols (67). The amount of each metabolite will be compared in the presence and absence of exposure to the compound based on HPLC elution profiling and subsequent mass spectrometry at the MSRC. Completion of these studies will define the specific steps within the heme biosynthetic pathway that are affected by '882. Moreover, when taken together with results obtained from the above-describe studies, these data will provide a mechanistic explanation for how '882 increases endogenous heme levels. This work will provide a molecular blueprint to guide future efforts aimed at pharmacologically manipulating heme synthesis pathways in bacterial pathogens.

Example 6 (Prophetic, in Part)—Define how Alterations in Heme Synthesis Affect Bacterial Physiology and Virulence Compound '882 perpetuates staphylococcal respiration and inhibits the shift to fermentative growth. This pharmacological redirection of central metabolism is toxic to $S.$ $aureus$ when grown in conditions that require fermentation. $S.$ $aureus$ is capable of infecting virtually all vertebrate tissues, including sites that are devoid of oxygen required for aerobic respiration. Therefore, it is contemplated that $S.$ $aureus$ must generate energy through fermentation when colonizing these sites. The present inventors contemplate that pharmacologic manipulation of heme synthesis will perpetuate respiration and protect against staphylococcal infections that require fermentative growth. The present inventors will (i) define the impact of altered heme synthesis on central metabolism and (ii) determine how manipulation of heme synthesis impacts virulence in a murine model of staphylococcal abscess formation, an infection site that likely requires fermentative growth.

To assess the contribution of heme synthesis to central metabolism, the impact of heme overproduction as well as underproduction will be evaluated. Staphylococcal strains inactivated for heme synthesis (ΔhemB) are available. The large number of genes required for heme synthesis presents a significant challenge for genetic engineering of a heme overproducing strain. Fortunately, '882 increases endogenous heme production, so '882-treated $S.$ $aureus$ can be used to measure the impact of increased heme abundance on staphylococcal physiology. To monitor the impact of heme synthesis on bacterial metabolism, glucose consumption and lactate production will be measured in wildtype $S.$ $aureus$, ΔhemB, and '882-exposed $S.$ $aureus$ as described above. Oxygen consumption will be measured using a Clark-type electrode. In addition, the fermentative end products malate, acetate, and formate will each be quantified spectrophotometrically by following the production of NADH due to the enzymatic degradation of each acidic end product. To obtain a more global perspective of the impact of heme synthesis on bacterial metabolism, DNA microarray analysis on wildtype $S.$ $aureus$, ΔhemB, and '882-exposed $S.$ $aureus$ will be performed. Samples will be taken from bacteria grown in conditions that support both respiratory and fermentative growth, and microarray analysis will be performed in the Functional Genomics Shared Resource (FGSR) at Vanderbilt.

To determine the contribution of regulated heme synthesis to infection, wildtype $S.$ $aureus$, and ΔhemB will be grown overnight and diluted into fresh medium on the following day. After incubation at 37° C. for three hours (approximate ($OD_{600}$ 0.5), staphylococci will be washed and diluted. Six to eight week old BALB/c mice will be inoculated intravenously with 1×10$^6$ CFU staphylococcal suspensions. In the hands of the present inventors, this model leads to significant visceral abscess formation at 96 hours following infection. To evaluate overproduction of heme, a subset of mice infected with wildtype $S.$ $aureus$ will be exposed to '882 (16, 64, and 256 mg/kg) or PBS control through intraperitoneal injection at 12 hour intervals initiated at the time of infection. Four days following the infection, mice will be weighed prior to euthanasia with compressed $CO_2$. Kidneys, livers, hearts, lungs, and spleens will be removed, weighed, and homogenized in 0.5% Triton X-100. Staphylococci will be counted by dilution and colony formation on solid growth medium. These experiments will determine the impact of genetic and pharmacological manipulation of heme synthesis on staphylococcal metabolism and pathogenicity. Moreover, they will reveal how heme synthesis impacts gene expression in multiple growth conditions, setting the stage for the functional annotation of new genes involved in the metabolic pathways of $S.$ $aureus$.

Example 7 (Prophetic in Part)—a High-Throughput Screen Identifies Activators of HssRS In order to perform a high-throughput screen (HTS) for small molecule activators of $S.$ $aureus$ HssRS, we created an hrtAB-driven expression system in the pXen-1 vector, which contains a luxABCDE operon that produces blue-green light when expressed. This construct was used to screen a library of approximately 160,000 small molecules and resulted in the identification of 250 positive hits. Based on luminescence values, the top 110 hits were subjected to a secondary screen using a xylE reporter assay to eliminate compounds that generated non-specific luminescence. Hits that passed this secondary screen were further tested in a tertiary screen for their ability to adapt $S.$ $aureus$ to heme toxicity by growth curve analyses. One embodiment of the present invention, '882 was a potent activator of hrtAB expression. '882 activates the hrtAB promoter in a dose-responsive manner requiring HssRS and pre-adapts S. aureus for heme toxicity (FIG. 9). These properties were observed for both commercially purchased and independently synthesized preparations of '882. These results establish embodiments of the present invention, including '882 as a small molecule activator of the HssRS-dependent heme stress response.

Figure 10D:
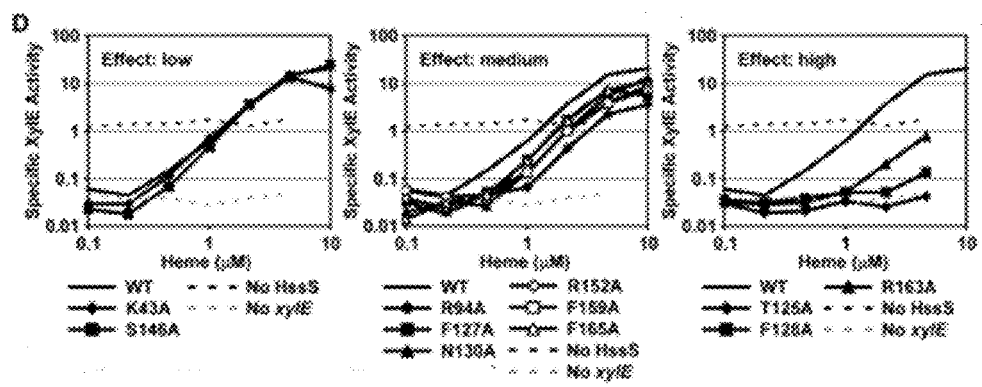
Figure 10E:
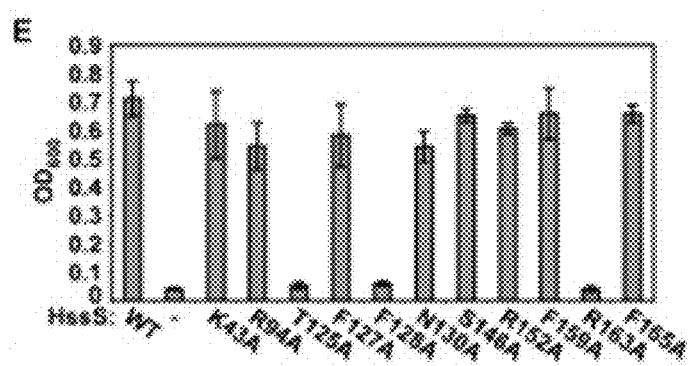
Figure 10F:
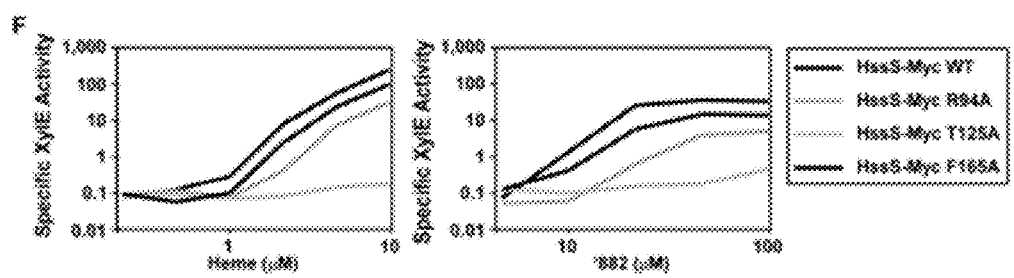

Example 8 (Prophetic in Part)—Compounds of the Present Invention Stimulate Heme Biosynthesis to Activate HssRS To determine the mechanism by which '882 activates HssRS, the residues required for HssS heme sensing were identified. An alignment of the HssS extracytoplasmic domain from members of the Firmicutes encoding putative hss/hrt systems was used to predict residues required for heme sensing in S. aureus. Alanine substitution mutants were generated at ten highly conserved residues and one non-conserved residue (FIG. 10A). These HssS variants were expressed in S. aureus ΔhssS and their expression levels were compared to wildtype by immunoblot (FIG. 10B). Next, their responsiveness to heme was quantified by XylE activity and growth curve analyses (FIGS. 10C-E). Analogous to Bacillus anthracis HssS, residues T125, F128, and R163 are required for heme sensing and HssS function in S. aureus. To gain insight into the mechanism by which '882 activates HssS, the ability of '882 to activate HssS substitution mutants with heme sensing defects was probed. R94A, T125A, and F165A were chosen for this analysis as they represent three mutations that reduce HssS heme sensing to different degrees. The impact of these mutations on HssS activation by '882 mirrored that observed upon heme exposure (FIG. 10F). This result indicates that heme and '882 trigger HssS signaling through similar residues despite being structurally distinct.

Figure 11A:
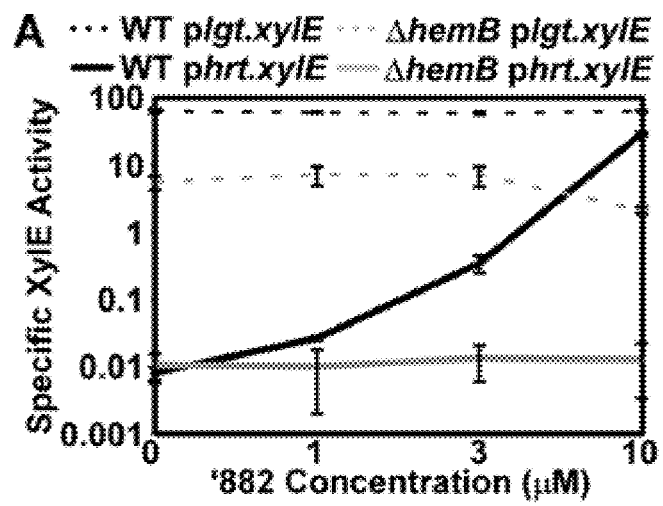
FIGS. 11A-11E describes embodiments of the present invention acting through endogenous heme biosynthesis to activate HssRS and stimulate heme production. (A) $S.$ $aureus$ wildtype (WT, black lines) and the heme auxotroph hemB::ermC (ΔhemB, gray lines) were transformed with plasmids constitutively expressing XylE (plgt.xylE, dashed lines) or with xylE under the control of the hrtAB promoter (phrt.xylE, solid lines). Triplicate cultures of these strains were grown in the presence of '882 and XylE activity was measured. (B) Heme levels in triplicate cultures of $S.$ $aureus$ treated with the indicated additive were quantified using the pyridine hemochromogen assay and normalized to the concentration of protein in the whole cell lysates. Inset: Pellets from a culture grown with 40 µM '882 are darker when compared to vehicle treated $S.$ $aureus$. (A and B) Error bars represent one standard deviation from the mean. (C) Exact-mass mass spectrometric analysis was used in conjunction with UPLC to detect and quantify heme in protoplasts from cells treated with 40 µM '882 or vehicle grown in triplicate. Measured heme molecules were referenced to estimated CFUs per pellet, factoring in dilutions. Dead or lysed cells would also contribute to the measurement. Hence the measured numbers are considered upper estimates. Samples measured in duplicate or triplicate injections had typical errors of <5% between analytical replicates. Error bars represent the standard deviation and significance was calculated using a two-tailed Student's t-test. (D) Adaptation by heme and '882 in $Corynebacterium$ $diphtheriae$ was tested by growth analyses. Triplicate cultures were grown overnight in medium containing vehicle, 5 µM heme or 50 µM '882 and subcultured into medium containing 15 µM heme. The CFUs were enumerated 2.5 h after inoculation and normalized to cultures unexposed to heme. Shown is the average of five replicates; error bars represent standard error of the mean and significance was determined by a two-tailed Student's t-test. (E) Adaptation by heme and '882 in $Staphylococcus$ $haemolyticus$ was tested by growth analyses. Triplicate cultures were grown overnight in medium containing the indicated additive and subcultured into medium containing 30 µM heme. Growth was monitored by measuring the optical density at 600 nm ($OD_{600}$) over time. Error bars represent one standard deviation from the mean.
Figure 11B:
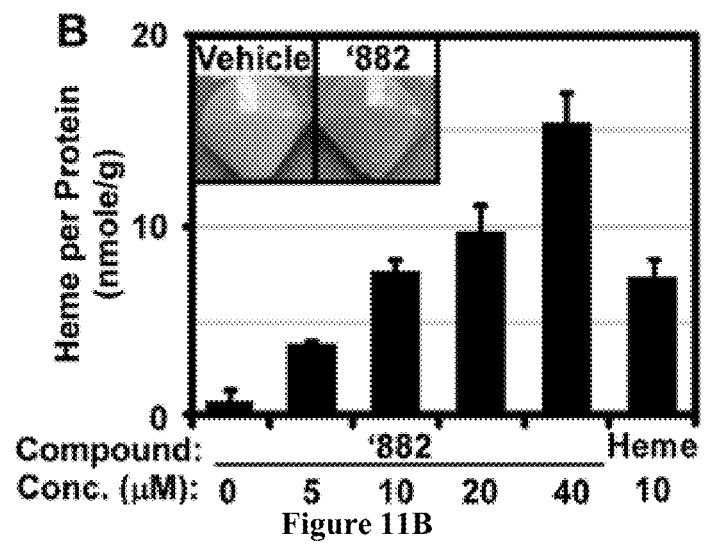
Figure 11C:
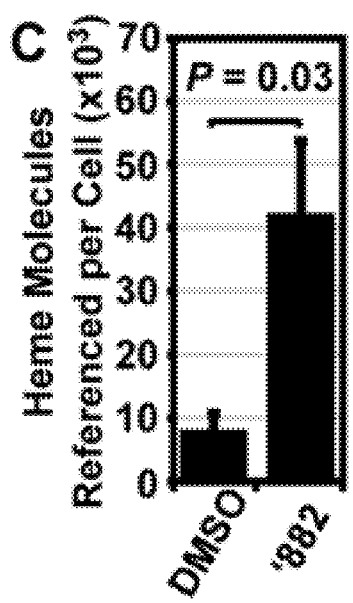

This observation suggests that '882 triggers HssRS through a mechanism similar to that of heme. A potential explanation is that '882 is a small molecule activator of endogenous heme synthesis. To test this model, the phrt.xylE reporter plasmid was transformed into the heme auxotroph hemB::ermC (ΔhemB) and HssRS activation was evaluated upon '882 exposure (10). In contrast to wildtype S. aureus, '882 does not activate HssRS in ΔhemB (FIG. 11A). The loss of '882-mediated activation of HssRS in ΔhemB is not due to the slower growth rate of this strain as XylE activity from a constitutively expressed xylE (plgt.xylE) is only modestly decreased (FIG. 11A). Furthermore, exogenous heme activates HssRS in ΔhemB, indicating that ΔhemB HssRS is still able to sense heme. These observations are consistent with a model whereby '882 exposure leads to an increase in intracellular heme and subsequent HssS activation. In support of this model, intracellular heme levels increase in a dose-responsive manner in bacteria treated with '882 (FIGS. 11B and C). Moreover, '882 exposure leads to a darkening of S. aureus pellets indicative of massive heme accumulation in these cells (FIG. 11B, inset). The activation of HssS by '882 is not due to enzymatic degradation of heme as '882 still activates HssS in a strain of S. aureus lacking all heme oxygenases.

To determine if the endogenous heme produced as a result of '882 exposure is available for use in cellular processes, cytoplasmic heme availability was measured by quantifying intracellular levels of the cytoplasmic heme oxygenase IsdG. In the absence of exogenous heme, IsdG is rapidly degraded; however, heme binding stabilizes IsdG and reduces its proteolytic degradation. Therefore, the abundance of IsdG reflects the cytoplasmic levels of heme. Following '882 treatment, the intracellular abundance of IsdG increased in a dose-dependent manner. IsdG is not stabilized when S. aureus ΔhemB is grown in the presence of '882, demonstrating that stabilization of IsdG requires endogenous heme. Moreover, IsdG abundance increases in ΔhemB exposed to exogenous heme, indicating that heme-dependent stabilization of IsdG is not generally disrupted in this strain. Taken together, these experiments reveal that '882 exposure increases cytoplasmic heme availability.

Figure 11D:
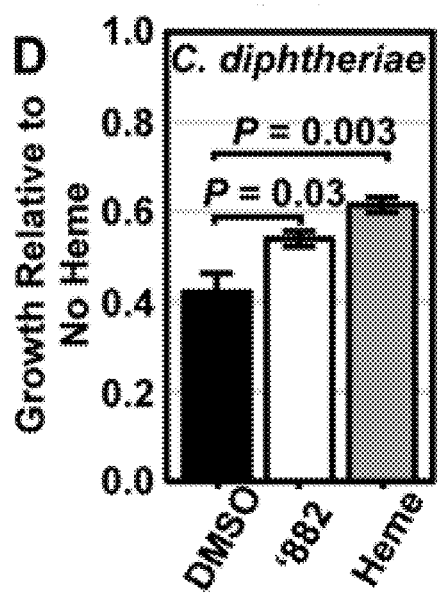
Figure 11E:
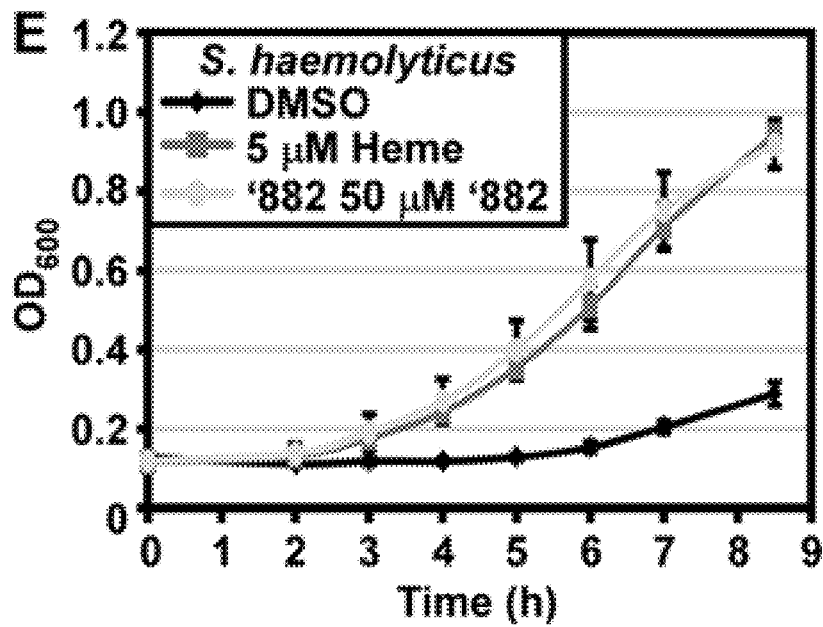

To test whether other bacterial heme sensing proteins monitor endogenous heme, the ability of the Corynebacterium diphtheriae ChrAS and Staphylococcus haemolyticus HssRS TCSs to sense '882 by adaptation growth curve was examined. Due to the slow growth and low optical density achieved by C. diphtheriae, enumerating CFUs, a more sensitive measure of growth, was used to assess the adaptation of this pathogen. Pre-treatment of both species with either heme or '882 improved survival in heme as compared to non-adapted cultures (FIGS. 11D and E). These data suggest that '882 may stimulate heme biosynthesis in multiple Gram-positive bacteria and support the hypothesis that the ability to respond to both endogenous and exogenous heme is a conserved function of bacterial heme sensor systems.

Example 9 (Prophetic in Part)—Compounds of the Present Invention Diminished Fermentative Activity of S. aureus To define the mechanism by which '882 manipulates heme biosynthesis, a S. aureus transposon library was screened for mutants unable to sense '882 or heme by growth curve adaptation. Of the approximately 7,000 mutants screened, only one strain was completely unable to be pre-adapted for heme toxicity by '882; this strain contained a transposon in the hemL gene involved in heme biosynthesis. Forty-four additional mutants were found to have a defect in '882 sensing and of those, 17 were also deficient in heme sensing. See Table 1, below:

| Tranposon ID | Integration site | Newman | Gene name | Gene description |
|---|---|---|---|---|
| | | Co-factors | | |
| 11e11*,1 | 555437-8 | NWMN_0482 | pdxT | pyridoxal 5'-phosphate biosynthesis |
| 21D1 | 1728844-5 | NWMN_1561 | hemL | glutamate-1-semialdehyde aminotransferase |
| | | Carbohydrates | | |
| 6E11 | 755114-5 | NWMN_0672 | | aldo/keto reductase family protein |
| 33F2, (66E5, 68B5, 68E8)[2], 67E11 | 1583073-4, 1584195-6, 1584189-90 | NWMN_1414 | malA | α-D-1,4-glucosidase |

-continued

| Tranposon ID | Integration site | Newman | Gene name | Gene description |
|---|---|---|---|---|
| Cell wall | | | | |
| 52A8 | 1443696-7 | NWMN_1310 | alr2 | alanine racemase 2 |
| 51C3 | 1444887-8 | NWMN_1311 | lysA | diaminopimelate decarboxylase |
| 50 G5 | 1513348-9 | NWMN_1349 | ald | alanine dehydrogenase |
| Amino acids & proteins | | | | |
| (24B2, 27D3, 24H6)* | 595672-3 | NWMN_0516 | ilvE | branched-chain-amino-acid aminotransferase |
| 75D6 | 1610144-5 | NWMN_1439 | gcvPB | glycine cleavage system P protein, subunit 2 |
| 6F8 | 1678876-7 | NWMN_1513 | | peptidase U32 family protein |
| DNA & RNA | | | | |
| 8D8 | 1614867-8 | NWMN_1446 | | competence protein ComGC-like protein |
| 6H6 | 1659859-60 | NWMN_1490 | | DNA internalization-related competence protein ComEC/Rec2 |
| 4E5, 5B10, 14D7, 18G5, 51G4* | 1628735-36, 1629189-90, 1629015-6, 1629152-3, 1628880-1 | NWMN_1461 | | ATP dependent RNA helicase DEAD/DEAH box family protein |
| 76C11 | 1660941-2 | NWMN_1491 | | competence protein ComEB required for DNA binding and uptake |
| 17B7* | 1681514-5 | NWMN_1517 | | conserved hypothetical protein |
| 2F2* | 2296289-90 | NWMN_rRNA15 | | 23S rRNA |
| Transporters | | | | |
| 11B6, 12F8* | 982508-9, 982803-4 | NWMN_0886 | | Hypothetical protein; transporter; next to murGE |
| (66C5, 69D11) | 1670973-4 | NWMN_1505 | | hypothetical protein contains NRAMP domain |
| Regulators | | | | |
| 63C6 | 736803-4 | NWMN_0655 | | MarR family protein |
| 48F5* | 756768-9 | NWMN_0674 | saeS | S. aureus accessory element histidine kinase |
| 44C2* | 1213708-9 | NWMN_1109 | pryR | pyrimidine operon regulatory protein, |
| 10D6* | 1569662-3 | NWMN_1399 | srrB | staph respiratory response histidine kinase |
| 32G6* | 1461723-4 | NWMN_1328 | | response regulator |
| 31H6* | 1813162-3 | NWMN_1629 | ccpA | catabolite control protein A |
| Phage | | | | |
| 33G8 | 1124401-2 | NWMN_1026 | | conserved hypothetical protein; identical to ORF040 of Bacteriophage 53 |
| 66F2 | 1990835-6 | NWMN_1776 | | conserved hypothetical protein |
| Hypothetical and intergenic | | | | |
| 69E5 | 780077-8 | NWMN_0695/0696 | intergenic | Hypothetical protein (similar to MDR transporter) and di-/tripeptide ABC transporter |
| 9F8* | 846026-7 | NWMN_0751 | promoter | hypothetical protein |
| 49G8 | 1060937-8 | NWMN_0955/0956 | intergenic | conserved hypothetical proteins |
| 50F8 | 1624756-7 | NWMN_1457/sodA | intergenic | Zn specific metalloregulatory protein and superoxide dismutase Mn/Fe family protein |
| 8G6 | 1668046-7 | NWMN_1502/1503 | intergenic | hypothetical protein and enterotoxin family protein |
| 77D12 | 1670682-3 | NWMN_1504 | promoter | hypothetical protein |
| 46B9 | 1690951-2 | NWMN_1524 | | aminotransferase, class V |
| 52F2 | 1755385-6 | NWMN_1584 | promoter | hypothetical protein |
| 2F9 | 1931846-7 | NWMN_1732 | | hypothetical protein |
| 52B8 | 2137622-3 | NWMN_1930 | | hypothetical protein |
| 52G4 | 2270169-70 | NWMN_2051/52 | intergenic | lytic regulatory protein and truncated resolvase |
| 32C7* | 2384526-7 | NWMN_2161 | | conserved hypothetical protein |

[1] An asterisk denotes mutants that are less sensitive to both heme and '8882.
[2] Mutants grouped in parentheses reflect identical integration sites.

Figure 12A:
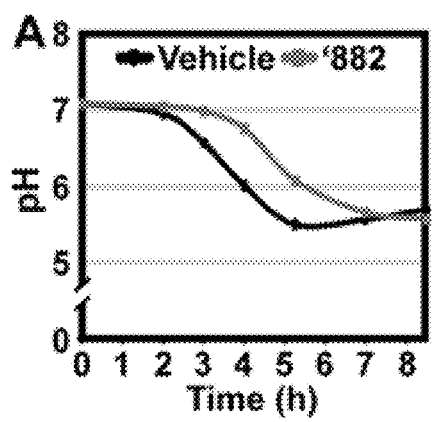
FIGS. 12A-12C show examples of the present invention diminish fermentative activity. $S.$ $aureus$ was grown in triplicate under aerobic conditions in the presence of vehicle (black lines) or 40 µM '882 (gray lines). At the indicated time intervals, culture supernatants were sampled and the (A) pH, (B) D-glucose, and (C) D- and L-lactate were quantified. Error bars represent one standard deviation from the mean.
Figure 12B:
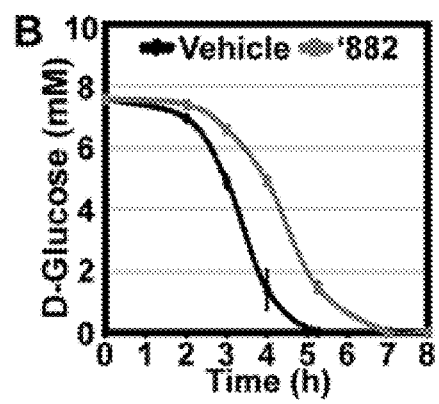
Figure 12C:
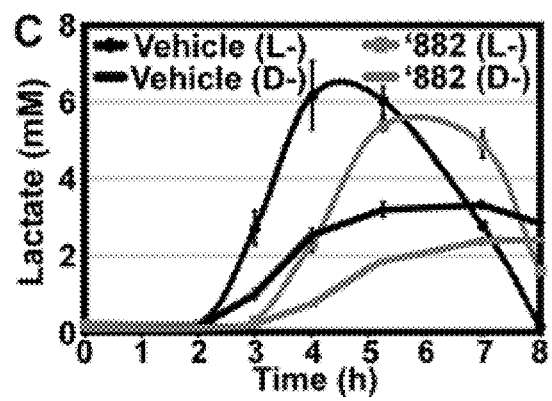

A number of genes required for sensing heme and/or '882 are involved in central metabolic pathways including a predicted α-D-1,4-glucosidase (malA), the catabolite control protein (ccpA), respiratory response two-component system (srrAB), branched-chain amino acid amino transferase (ilvE), bifunctional pyrimidine regulator/uracil phosphoribosyltransferase (pryR), and pyridoxal 5'-phosphate synthase glutamine amidotransferase subunit (pdxT). Consistent with these observations, bacteria treated with '882 had reduced glycolytic activity as indicated by slower acidification of the medium that correlated with delayed consumption of D-glucose and reduced production of L- and D-lactate (FIG. 12). These observations suggest that as '882 induces endogenous heme biosynthesis, it also reduces the glycolytic or fermentative capacity of S. aureus. These results support a model whereby the metabolic state of S. aureus and heme homeostasis are functionally interconnected.

Figure 13A:
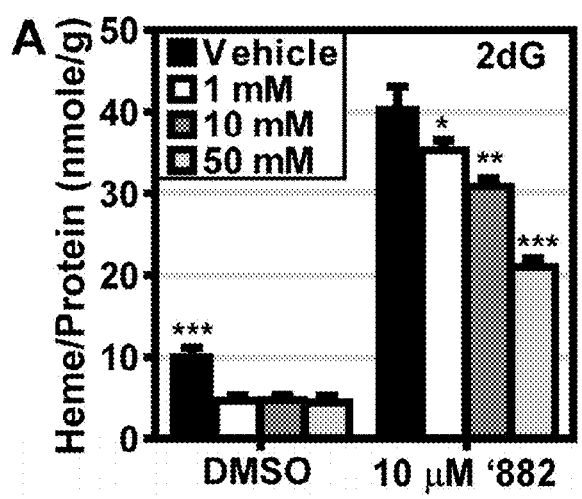
FIGS. 13A-13B explain glycolytic activity regulates heme biosynthesis. $S.$ $aureus$ was grown in triplicate in the presence of vehicle or 10 µM '882. Heme levels were quantified using the pyridine hemochromogen assay and normalized to the concentration of protein in the whole cell lysates. (A) Cultures were treated with the indicated dose of 2-deoxyglucose (2dG). *=$p \leq 0.05$, =$p \leq 0.001$, *=$p \leq 0.0001$ (B) Wildtype (WT) and ΔpfkA Newman were cultured in TSB+1% pyruvate. # indicates the signal was below the limit of detection. (A and B) Error bars represent the standard error of the mean from three independent experiments. Statistical significance was determined using an unpaired Student's t-test.
Figure 13B:
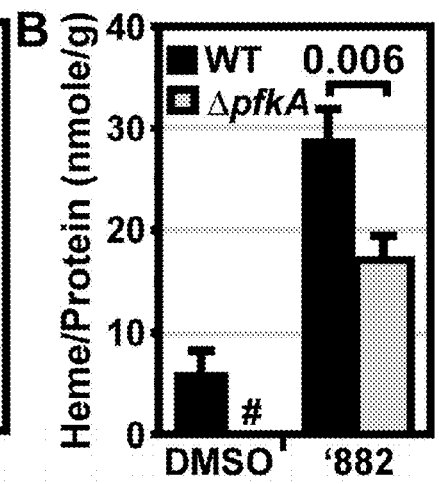

To test whether heme biosynthesis interfaces with central metabolism, we first assessed the effect of 2-deoxyglucose (2dG) on heme biosynthesis. The glucose analogue 2dG primarily inhibits the phosphoglucoisomerase reaction, the second step in glycolysis. Treatment of S. aureus with 2dG reduces endogenous heme levels and antagonizes '882 activity (FIG. 13A). Deletion of 6-phosphofructokinase (pfkA), the third enzyme in glycolysis, results in a loss of glucose uptake and decreased acid end product secretion in S. aureus. In agreement with the effect of 2dG on heme biosynthesis, both basal and '882-induced heme biosynthesis are suppressed in ΔpfkA (FIG. 13B). These data implicate a product of glycolysis in stimulating heme biosynthesis, strengthening the observed link between the regulation of heme biosynthesis and central metabolism.

Figure 14A:
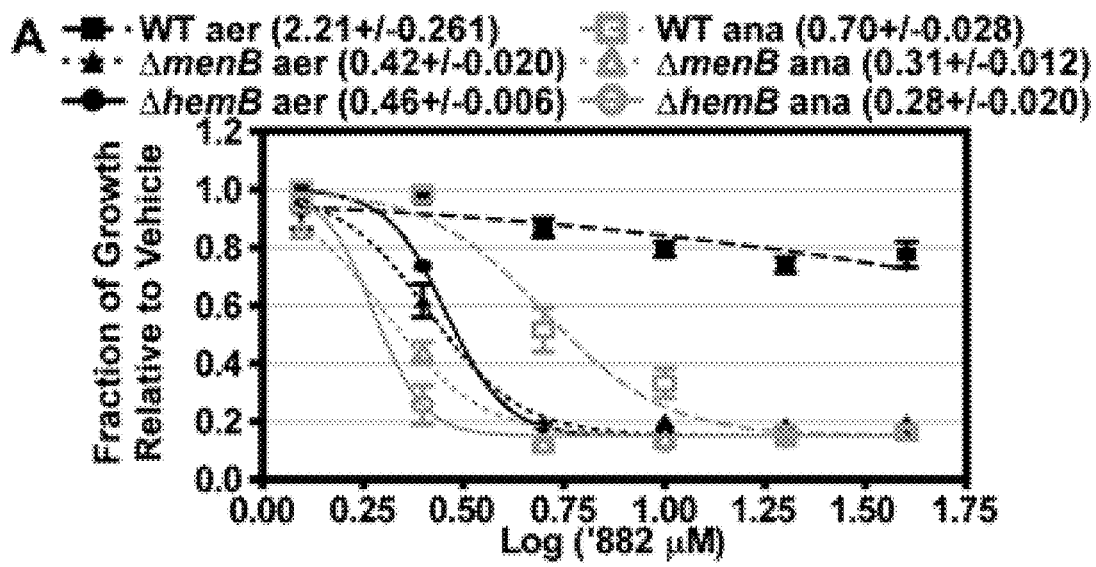
FIGS. 14A-14C show embodiments of the present invention inhibit fermenting $S.$ $aureus$. (A) $S.$ $aureus$ wildtype (WT, dashed lines), the menaquinone auxotroph (ΔmenB, dotted lines), and the heme auxotroph hemB::ermC (ΔhemB, solid lines) were grown in triplicate under aerobic (aer, black lines) and anaerobic (ana, gray lines) conditions in the presence of the indicated log of the concentration of '882 (µM). After 18 h the absorbance at 600 nm ($OD_{600}$) was measured and normalized to vehicle (DMSO) treated bacteria. Curves were fit by nonlinear regression analysis and absolute log IC50 values were calculated in Prism with the top set at 1.0 and the bottom set at 0.15. Log IC50 values are indicated in parentheses in the figure key +/− standard error of the mean. All log IC50 values were statistically different from WT aerobic log IC50 when analyzed by one-way ANOVA with a Dunnett post test (p<0.001). Error bars represent the standard error of the mean. (B) Triplicate cultures of $S.$ $aureus$ were grown in the presence of the indicated additive. After 24 h, CFUs were enumerated on TSA containing 5 µg/ml gentamicin and plain TSA with a limit of detection of 100 CFUs/ml (minimum y-value); # indicates colonies were not identified above the limit of detection. Shown is the average of three independent experiments. Error bars represent one standard deviation from the mean. (C) $S.$ $aureus$ was grown in the presence of vehicle (DMSO) or 40 µM '882 and coated in serum. Murine PMNs were elicited with casein and harvested from the peritoneum. The ability of neutrophils to kill $S.$ $aureus$ in the presence of '882 was assessed by comparing CFUs recovered from neutrophil-exposed $S.$ $aureus$ to those recovered from identical conditions lacking neutrophils. The mean of at least six independent experiments performed in triplicate are represented by the data; error bars represent standard error of the mean and significance was determined by a two-tailed Student's t-test.

Example 10 (Prophetic in Part)—Embodiments of the Present Invention are Bacteriostatic to Fermenting S. Aureus The '882-dependent suppression of substrate level phosphorylation in aerobic cultures suggests that the compound may inhibit fermentative growth. Indeed, when S. aureus was grown anaerobically in the presence of '882, growth was dramatically reduced (FIG. 14A). In addition, a strain bearing a lesion in the MK biosynthesis gene menB (ΔmenB), which cannot respire and solely ferments to produce energy, is more susceptible to '882 toxicity than wildtype (FIG. 14A). '882 is bacteriostatic to ΔmenB both aerobically and anaerobically. Moreover, when '882 is combined with the respiratory poison potassium cyanide (KCN), S. aureus growth is inhibited, even under aerobic conditions. Taken together, these data indicate that '882 inhibits S. aureus fermentative growth and that respiration is protective against '882 toxicity. Notably, '882 inhibits the growth of C. diphtheriae, supporting the conserved activity of '882 in heme sensing organisms. Furthermore, ΔhemB, an SCV deficient in heme biosynthesis, is also sensitive to '882, indicating that heme accumulation is not the source of toxicity, but rather a result of '882 perturbing S. aureus metabolism (FIG. 14A).

Figure 14B:
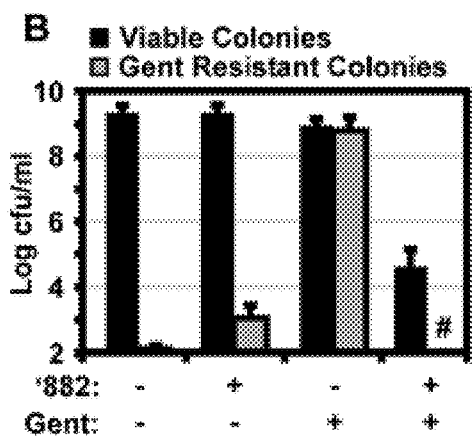

Example 11 (Prophetic in Part)—Embodiments of the Present Invention Prevent the Evolution of Antibiotic Resistance S. aureus SCVs are obligate fermenters that emerge in response to aminoglycoside treatment. Since '882 is toxic to fermenting staphylococci, we hypothesized that '882 would prevent the outgrowth of antibiotic resistant SCVs in the presence of aminoglycosides. To test this, S. aureus was grown in the presence of vehicle, gentamicin, '882, or a combination of gentamicin and '882, and the evolution of gentamicin resistance was monitored. Bacteria treated with gentamicin alone became resistant to gentamicin, whereas '882 treatment alone did not affect the number of viable or gentamicin-resistant bacteria (FIG. 14B). Combining '882 with gentamicin resulted in a 5-log reduction in bacterial viability and eliminated all detectable gentamicin-resistant colonies (FIG. 14B). This suggests that targeting fermentation can be used as an adjunctive therapy with antibiotics that are active against respiring S. aureus to improve antibacterial action and reduce the emergence of antibiotic resistance.

Figure 14C:
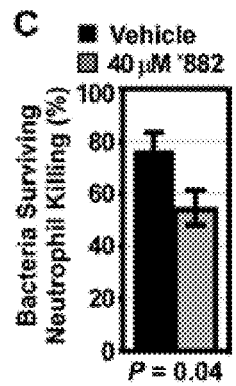

Example 12 (Prophetic in Part)—Embodiments of the Present Invention Enhance Innate Immune Function Neutrophils are the first immune cells to respond to the site of a S. aureus infection (18). As part of the innate defense program, they secrete noxious chemicals to kill invading pathogens. One component of this toxic milieu is nitric oxide (NO.), which inactivates iron-containing proteins critical for respiration. In agreement with the observation that '882 is particularly toxic to fermenting S. aureus, simultaneous exposure of S. aureus to '882 and NO. is more antibacterial than treatment with either molecule alone. Additionally, '882 improves neutrophil-dependent killing of S. aureus but does not overtly affect neutrophil viability (FIG. 14C). These results support the notion that '882 may have therapeutic efficacy against bacterial invaders by augmenting the killing activity of neutrophils.

Example 13 (Prophetic in Part)—Embodiments of the Present Invention Reduce S. aureus Pathogenesis In Vivo Abscesses, which are purulent lesions containing bacteria and neutrophils surrounded by a pseudocapsule, are a hallmark of S. aureus infections. It is likely that fermentation is critical to staphylococcal pathogenesis since abscesses are thought to be anaerobic environments. Testing this hypothesis is challenging as S. aureus fermentation is branched, so genetic inactivation of fermentation is difficult. The toxic effect of '882 toward fermenting S. aureus provides an opportunity to gain initial insights into the role of fermentation in pathogenesis. However, '882 has a metabolically labile furan group which may form protein adducts and deplete glutathione in vivo. Thus, the furan was replaced with a 2-fluorophenyl group to create a more biologically stable derivative, VU0420373 ('373) (FIG. 15A). '373 activates HssRS as evidenced by its ability to increase the expression of the xylE reporter gene and pre-adapt S. aureus for heme toxicity (FIGS. 15B and C). In addition, '373 inhibits the growth of S. aureus ΔmenB, although to a lesser extent than '882 (FIG. 15D).

Intraperitoneal administration of '373 to mice intravenously infected with S. aureus resulted in a significant 1-log decrease in CFUs recovered from the livers of '373-treated animals as compared to vehicle (FIG. 16A). Notably, '373-treatment reduced tissue pathology associated with infection as demonstrated by a significant reduction in the number of liver abscesses (FIG. 16B). This liver-specific reduction in bacterial burden and inflammation correlates with an accumulation of '373 in the livers of treated animals as shown by Imaging Mass Spectrometry (IMS) (FIG. 16C, D). To quantify the tissue level of '373, portions of the livers were excised and '373 concentrations were determined by HPLC-MS. A linear relationship between tissue level and dose of '373 administered was observed. Average spectral intensity extrapolated from IMS data of '373 reflected a dose-response relationship similar to that observed by HPLC-MS, confirming the suitability of IMS for monitoring tissue levels of '373. Both the HPLC-MS and IMS data support the notion that the therapeutic effect of '373 is due to the interaction of the compound with S. aureus as it is found at the site where bacterial growth is restricted. Although the therapeutic benefits of '373 could be due to alternative activities of this molecule, these results provide evidence that targeting fermentation in a facultative anaerobe may be a viable therapeutic strategy. The therapeutic value of this strategy is supported by the observation that S. aureus generates resistance to '882 in anaerobic conditions with a frequency of approximately 1 in $10^{-7}$ CFUs.

Example 14 (Prophetic in Part)—Discussion of HTS-Identified Activators of HssRs

Here, the present inventors describe an HTS that identified small molecule activators of the S. aureus heme sensor system HssRS. Embodiments of the present invention increase endogenous heme levels and activates HssRS through the heme biosynthesis pathway. This effect appears to be due to a perturbation of the metabolic state of S. aureus as transposon insertions targeting genes involved in metabolism contribute to the ability of the bacteria to sense '882. This hypothesis is supported by the observations that '882 reduces fermentative processes and is bacteriostatic to fermenting staphylococci. Targeting staphylococcal fermentation has therapeutic potential as it augments innate immune function and prevents outgrowth of antibiotic resistant colonies in vitro, and reduces S. aureus liver colonization and associated inflammation in vivo.

Employing embodiments of the present invention as a probe has revealed that HssRS responds to both exogenous and endogenous heme accumulation. The discovery that S. aureus monitors intracellular heme status through HssRS suggests that other bacterial heme sensing systems may also sense intracellular heme. This is supported by the observation that C. diphtheriae and S. haemolyticus are also adapted for heme toxicity by '882. The fact that '882 is sensed by C. diphtheriae and S. haemolyticus indicates that the target of '882 is present in multiple pathogens, establishing this molecule as a powerful probe for studying intracellular heme metabolism. The utility of embodiments of the present invention as a probe is further supported by the observation that IsdG binds endogenously synthesized heme following stimulation with '882. This implicates bacterial heme oxygenases in intracellular heme turnover, a result that is likely generalizable to all bacterial heme oxygenases as P. aeruginosa hemO has also been shown to act on endogenous heme. Expanding the function of bacterial heme degrading enzymes beyond nutrient iron acquisition establishes a mechanism by which bacteria can adjust iron and heme levels to satisfy cellular needs.

Heme biosynthesis is typically regulated by cellular iron or heme levels, although there is some evidence that it is tied to central metabolism. The perturbation of heme homeostasis and central metabolism by '882 suggests that the two cellular processes are coordinated in S. aureus. Strengthening this hypothesis, both chemical and genetic inhibition of the upper steps in glycolysis result in suppressed basal and '882-induced heme levels. These data suggest that an intact glycolytic pathway is required for '882-dependent activation of heme biosynthesis, further supporting a functional interconnection between central metabolism and heme biosynthesis in S. aureus. An integration of heme homeostasis with central metabolism is consistent with the fact that heme and iron are critical co-factors for many enzymes involved in energy conversion. Further studies employing '882 could dissect the interplay between heme and central metabolism in both S. aureus and other pathogens.

The activity of embodiments of the present invention against fermenting bacteria has broad therapeutic potential.

For example, as shown herein embodiments are bacteriostatic to SCVs, which often emerge during recurrent and persistent S. aureus infections. This may be generalizable across other infectious diseases as N. gonorrhoeae, E. coli, P. aeruginosa, and S. Typhimurium can also spawn SCVs. In addition to being used as a treatment for persistent infections, derivatives of '882 could have utility in combinatorial-therapy with antibiotics that target respiring bacteria. As a proof of principle, co-treating S. aureus with gentamicin and '882 in vitro reduces bacterial viability and the outgrowth of antibiotic resistant populations. While gentamicin is typically used in combination with other primary antibiotic agents, it is often conjugated to beads and used as the primary antibiotic agent at the site of osteomyelitis infections. SCVs often arise during the prolonged antibiotic regimen required for treatment of osteomyelitis. Therefore, it is possible that an '882-gentamicin dual therapy could be used to improve therapy for osteomyelitis by preventing the generation of SCVs during infection. If '882 proves synergistic with other primary anti-staphylococcal agents such as β-lactams and vancomycin, it is possible that '882 could be used more broadly as an adjuvant to expand the antibiotic armamentarium that is effective against S. aureus infections.

The majority of bacterial pathogens use some combination of fermentation and respiration to produce ATP, suggesting that both are important for colonization and persistence. The importance of S. aureus fermentative pathways during infection is demonstrated by the fact that '373 reduces abscess formation and S. aureus growth in the livers of systemically infected mice. The observed effects of '373 on S. aureus pathogenesis support the notion that the abscess is an anaerobic environment and that bacterial fermentation is required for efficient colonization. Furthermore, the modest effect '373 has on S. aureus pathogenesis in vivo, despite its diminished bacteriostatic activity in vitro, highlights the promise of more potent, biologically compatible derivatives of '882 as novel therapeutics.

In summary, compounds of the present invention diminish fermentative processes in S. aureus, stimulate endogenous heme biosynthesis and activate the HssRS heme sensor. This compounds have two-fold utility as both a probe of bacterial physiology and an unconventional therapeutic.

Throughout this document, various references are mentioned. All such references are incorporated herein by reference, including the references set forth in the following list:

REFERENCES

1. Yarwood J M, McCormick J K, Schlievert P M. Identification of a novel two-component regulatory system that acts in global regulation of virulence factors of Staphylococcus aureus. J Bacteriol. 2001; 183(4):1113-23.
2. Novick R P, Ross H F, Projan S J, Kornblum J, Kreiswirth B, Moghazeh S. Synthesis of staphylococcal virulence factors is controlled by a regulatory RNA molecule. EMBO J. 1993; 12(10):3967-75.
3. Giraudo A T, Cheung A L, Nagel R. The sae locus of Staphylococcus aureus controls exoprotein synthesis at the transcriptional level. Arch Microbiol. 1997; 168(1): 53-8.
4. Fournier B, Klier A. Protein A gene expression is regulated by DNA supercoiling which is modified by the ArlS-ArlR two-component system of Staphylococcus aureus. Microbiology. 2004; 150(Pt 11):3807-19.

5. Recsei P, Kreiswirth B, O'Reilly M, Schlievert P, Gruss A, Novick R P. Regulation of exoprotein gene expression in *Staphylococcus aureus* by agr. Mol Gen Genet. 1986; 202(1):58-61.
6. Brunskill E W, Bayles K W. Identification and molecular characterization of a putative regulatory locus that affects autolysis in *Staphylococcus aureus*. J Bacteriol. 1996; 178(3):611-8.
7. Martin P K, Li T, Sun D, Biek D P, Schmid M B. Role in cell permeability of an essential two-component system in *Staphylococcus aureus*. J Bacteriol. 1999; 181(12):3666-73.
8. Klevens R M, Morrison M A, Nadle J, Petit S, Gershman K, Ray S, et al. Invasive methicillin-resistant *Staphylococcus aureus* infections in the United States. JAMA. 2007; 298(15): 1763-71.
9. Shi L, Sohaskey C D, Kana B D, Dawes S, North R J, Mizrahi V, et al. Changes in energy metabolism of *Mycobacterium tuberculosis* in mouse lung and under in vitro conditions affecting aerobic respiration. Proc Natl Acad Sci USA. 2005; 102(43):15629-34. PMCID: 1255738.
10. Endley S, McMurray D, Ficht T A. Interruption of the cydB locus in *Brucella abortus* attenuates intracellular survival and virulence in the mouse model of infection. J Bacteriol. 2001; 183(8):2454-62. PMCID: 95161.
11. Way S S, Sallustio S, Magliozzo R S, Goldberg M B. Impact of either elevated or decreased levels of cytochrome bd expression on *Shigella flexneri* virulence. J Bacteriol. 1999; 181(4):1229-37. PMCID: 93501.
12. Somerville G A, Chaussee M S, Morgan C I, Fitzgerald J R, Dorward D W, Reitzer L J, et al. *Staphylococcus aureus* aconitase inactivation unexpectedly inhibits post-exponential-phase growth and enhances stationary-phase survival. Infect Immun. 2002; 70(11):6373-82.
13. Andries K, Verhasselt P, Guillemont J, Gohlmann H W, Neefs J M, Winkler H, et al. A diarylquinoline drug active on the ATP synthase of *Mycobacterium tuberculosis*. Science. 2005; 307(5707):223-7.
14. Weinstein E A, Yano T, Li L S, Avarbock D, Avarbock A, Helm D, et al. Inhibitors of type II NADH:menaquinone oxidoreductase represent a class of antitubercular drugs. Proc Natl Acad Sci USA. 2005; 102(12):4548-53. PMCID: 555520.
15. Zoraghi R, See R H, Axerio-Cilies P, Kumar N S, Gong H, Moreau A, et al. Identification of Pyruvate Kinase in Methicillin-Resistant *Staphylococcus aureus* as a Novel Antimicrobial Drug Target. Antimicrob Agents Chemother. 2011; 55(5):2042-53.
16. Akerley B J, Rubin E J, Novick V L, Amaya K, Judson N, Mekalanos J J. A genome-scale analysis for identification of genes required for growth or survival of *Haemophilus influenzae*. Proc Natl Acad Sci USA. 2002; 99(2):966-71. PMCID: 117414.
17. Zoraghi R, See R H, Gong H, Lian T, Swayze R, Finlay B B, et al. Functional analysis, overexpression, and kinetic characterization of pyruvate kinase from methicillin-resistant *Staphylococcus aureus*. Biochemistry. 2010; 49(35):7733-47.
18. Cherkasov A, Hsing M, Zoraghi R, Foster L J, See R H, Stoynov N, et al. Mapping the protein interaction network in methicillin-resistant *Staphylococcus aureus*. J Proteome Res. 2011; 10(3):1139-50.
19. von Eiff C, Heilmann C, Proctor R A, Woltz C, Peters G, Gotz F. A site-directed *Staphylococcus aureus* hemB mutant is a small-colony variant which persists intracellularly. J Bacteriol. 1997; 179(15):4706-12.
20. Bullen J J. The significance of iron in infection. Rev Infect Dis. 1981; 3(6):1127-38.
21. Kumar S, Bandyopadhyay U. Free heme toxicity and its detoxification systems in human. Toxicol Lett. 2005; 157(3):175-88.
22. Torres V J, Stauff D L, Pishchany G, Bezbradica J S, Gordy L E, Iturregui J, et al. A *Staphylococcus aureus* regulatory system that responds to host heme and modulates virulence. Cell Host & Microbe. 2007; 1(2):109-19.
23. Yamamoto Y, Poyart C, Trieu-Cuot P, Lamberet G, Gruss A, Gaudu P. Roles of environmental heme, and menaquinone, in *Streptococcus agalactiae*. Biometals. 2006; 19(2):205-10.
24. Stauff D L, Bagaley D, Torres V J, Joyce R, Anderson K L, Kuechenmeister L, et al. *Staphylococcus aureus* HrtA is an ATPase required for protection against heme toxicity and prevention of a transcriptional heme stress response. J Bacteriol. 2008; 190(10):3588-96.
25. Schlag S, Fuchs S, Nerz C, Gaupp R, Engelmann S, Liebeke M, et al. Characterization of the oxygen-responsive NreABC regulon of *Staphylococcus aureus*. J Bacteriol. 2008; 190(23):7847-58. PMCID: 2583599.
26. Fernandez A, Lechardeur D, Derre-Bobillot A, Couve E, Gaudu P, Gruss A. Two coregulated efflux transporters modulate intracellular heme and protoporphyrin IX availability in *Streptococcus agalactiae*. PLoS Pathog. 2010; 6(4):e1000860.
27. Stauff D L, Skaar E P. *Bacillus anthracis* HssRS signalling to HrtAB regulates haem resistance during infection. Molecular Microbiology. 2009; 72(3):763-78.
28. Bibb L A, Schmitt M P. The ABC transporter HrtAB confers resistance to hemin toxicity and is regulated in a hemin-dependent manner by the ChrAS two-component system in *Corynebacterium diphtheriae*. J Bacteriol. 2010; 192(18):4606-17. PMCID: 2937406.
29. Yamamoto Y, Poyart C, Trieu-Cuot P, Lamberet G, Gruss A, Gaudu P. Respiration metabolism of Group B *Streptococcus* is activated by environmental haem and quinone and contributes to virulence. Mol Microbiol. 2005; 56(2): 525-34.
30. von Eiff C, Peters G, Becker K. The small colony variant (SCV) concept—the role of staphylococcal SCVs in persistent infections. Injury. 2006; 37 Suppl 2:S26-33.
31. Bullen J J, and Griffiths, E. Iron and Infection: Molecular, Physiological and Clinical Aspects. New York: John Wiley and Sons; 1999.
32. Ravichandran M, Ali S A, Rashid N H, Kurunathan S, Yean C Y, Ting L C, et al. Construction and evaluation of a O139 *Vibrio cholerae* vaccine candidate based on a hemA gene mutation. Vaccine. 2006; 24(18):3750-61.
33. Proctor R A, von Eiff C, Kahl B C, Becker K, McNamara P, Herrmann M, et al. Small colony variants: a pathogenic form of bacteria that facilitates persistent and recurrent infections. Nat Rev Microbiol. 2006; 4(4):295-305.
34. von Eiff C, Bettin D, Proctor R A, Rolauffs B, Lindner N, Winkelmann W, et al. Recovery of small colony variants of *Staphylococcus aureus* following gentamicin bead placement for osteomyelitis. Clin Infect Dis. 1997; 25(5):1250-1.
35. Salgado D R, Bozza F A, Pinto M, al. e, editors. Outbreak with small colony variants of methicillin-resistant *S. aureus* in an ICU. Interscience Conference on Antibmicrobial Agents and Chemotherapy; 2002 Dec. 19, 2001; Chicago, Ill.

36. Seifert H, von Eiff C, Fatkenheuer G. Fatal case due to methicillin-resistant *Staphylococcus aureus* small colony variants in an AIDS patient. Emerg Infect Dis. 1999; 5(3):450-3.
37. Ponce E, Flores N, Martinez A, Valle F, Bolivar F. Cloning of the two pyruvate kinase isoenzyme structural genes from *Escherichia coli*: the relative roles of these enzymes in pyruvate biosynthesis. J Bacteriol. 1995; 177(19):5719-22.
38. Stauff D L, Torres V J, Skaar E P. Signaling and DNA-binding Activities of the *Staphylococcus aureus* HssR-HssS Two-component System Required for Heme Sensing. J Biol Chem. 2007; 282(36):26111-21.
39. Stauff D L, Skaar E P. *Bacillus anthracis* HssRS signaling to HrtAB regulates heme resistance during infection. Mol Microbiol. 2009.
40. Stauff D L, Skaar E P. The heme sensor system (HssRS) of *Staphylococcus aureus*. Contributions to Microbiology. 2008; In Press.
41. Francis K P, Joh D, Bellinger-Kawahara C, Hawkinson M J, Purchio T F, Contag P R. Monitoring bioluminescent *Staphylococcus aureus* infections in living mice using a novel luxABCDE construct. Infect Immun. 2000; 68(6):3594-600.
42. Mazmanian S K, Liu G, Ton-That H, Schneewind O. *Staphylococcus aureus* sortase, an enzyme that anchors surface proteins to the cell wall. Science. 1999; 285(5428):760-3.
43. Reniere M L, Skaar E P. *Staphylococcus aureus* haem oxygenases are differentially regulated by iron and haem. Mol Microbiol. 2008; 69(5):1304-15.
44. Baell J B, Holloway G A. New Substructure Filters for Removal of Pan Assay Interference Compounds (PAINS) from Screening Libraries and for Their Exclusion in Bioassays. J Med Chem. 2010; 53(7):2719-40.
45. Workman P, Collins I. Probing the Probes: Fitness Factors For Small Molecule Tools. Chem Biol. 2010; 17(6):561-77.
46. Boxer M B, Jiang J K, Vander Heiden M G, Shen M, Skoumbourdis A P, Southall N, et al. Evaluation of substituted N,N'-diarylsulfonamides as activators of the tumor cell specific M2 isoform of pyruvate kinase. J Med Chem. 2010; 53(3):1048-55. PMCID: 2818804.
47. de Been M, Bart M J, Abee T, Siezen R J, Francke C. The identification of response regulator-specific binding sites reveals new roles of two-component systems in *Bacillus cereus* and closely related low-GC Gram-positives. Environ Microbiol. 2008; 10(10):2796-809.
48. Terstappen G C, Schlüpen C, Raggiaschi R, Gaviraghi G. Target deconvolution strategies in drug discovery. Nat Rev Drug Discov. 2007; 6(11):891-903.
49. Pucheault M. Natural products: chemical instruments to apprehend biological symphony. Org Biomol Chem. 2008; 6(3):424.
50. Piggott A M, Karuso P. Rapid Identification of a Protein Binding Partner for the Marine Natural Product Kahalalide F by Using Reverse Chemical Proteomics. Chem Eur J of Chem Bio. 2008; 9(4):524-30.
51. Dorman G, Prestwich G. Using photolabile ligands in drug discovery and development. Trends Biotechnol. 2000; 18(2):64-77.
52. FLEMING S. CHEMICAL REAGENTS IN PHOTOAFFINITY-LABELING. Tetrahedron. 1995; 51(46):12479-520.
53. Yamamoto S, Abe M, Nakanishi S, Murai M, Miyoshi H. Synthesis and characterization of photoaffinity probe of acetogenin, a strong inhibitor of mitochondrial complex I. Tetrahedron Letters. 2011; 52(24):3090-3.
54. Liu Q, Tor Y. Simple conversion of aromatic amines into azides. Org Lett. 2003; 5(14):2571-2.
55. Uddin M J, Crews B C, Ghebreselasie K, Tantawy M N, Marnett L J. [I-123]-Celecoxib Analogues as SPECT Tracers of Cyclooxygenase-2 in Inflammation. Acs Med Chem Lett. 2011; 2(2): 160-4.
56. Dorman G, OLSZEWSKI J, Prestwich G, HONG Y, AHERN D. SYNTHESIS OF HIGHLY TRITIATED 4-BENZOYL-L-PHENYLALANINE, A PHOTOACTIVATABLE AMINO-ACID. J Org Chem. 1995; 60(7): 2292-7.
57. Mesange F, Sebbar M, Capdevielle J, Guillemot J, Ferrara P, Bayard F, et al. Identification of two tamoxifen target proteins by photolabeling with 4-(2-morpholinoethoxy)benzophenone. Bioconjugate Chem. 2002; 13(4): 766-72.
58. Elizalde L, de los Santos G, Garcia A, Medellin D, Acosta R. Synthesis of novel photochromic 6-benzyloxospirobenzopyran compounds. Synthetic Commun. 2005; 35(24):3087-97.
59. Lamos S M, Krusemark C J, McGee C J, Scalf M, Smith L M, Belshaw P J. Mixed isotope photoaffinity reagents for identification of small-molecule targets by mass spectrometry. Angew Chem Int Edit. 2006; 45(26):4329-33.
60. Cheng K-W, Wong C-C, Wang M, He Q-Y, Chen F. Identification and characterization of molecular targets of natural products by mass spectrometry. Mass Spectrom Rev. 2009:n/a-n/a.
61. Bae T, Schneewind O. Allelic replacement in *Staphylococcus aureus* with inducible counter-selection. Plasmid. 2006; 55(1):58-63.
62. Pishchany G, McCoy A L, Torres V J, Krause J C, Crowe J E, Jr., Fabry M E, et al. Specificity for human hemoglobin enhances *Staphylococcus aureus* infection. Cell Host Microbe. 2010; 8(6):544-50.
63. Stary E, Gaupp R, Lechner S, Leibig M, Tichy E, Kolb M, et al. New Architectures for Tet-On and Tet-Off Regulation in *Staphylococcus aureus*. Appl Environ Microbiol. 76(3):680-7.
64. Crosa J. H. ARM, and S. M. Payne. Iron Transport in Bacteria. Jorge H. Crosa A R M, Shelley M. Payne, editor. Washington, D.C.: A.S.M. Press; 2004.
65. Hood M I, Jacobs A C, Sayood K, Dunman P M, Skaar E P. *Acinetobacter baumannii* Increases Tolerance to Antibiotics in Response to Monovalent Cations. Antimicrob Agents Chemother. 2010; 54(3):1029-41. PMCID: 2825970.
66. Torres V J, Attia A S, Mason W J, Hood M I, Corbin B D, Beasley F C, et al. *Staphylococcus aureus* fur regulates the expression of virulence factors that contribute to the pathogenesis of pneumonia. Infect Immun. 2010; 78(4): 1618-28. PMCID: 2849423.
67. Kim J S, Lim H K, Lee M H, Park J H, Hwang E C, Moon B J, et al. Production of porphyrin intermediates in *Escherichia coli* carrying soil metagenomic genes. FEMS Microbiol Lett. 2009; 295(1):42-9.
68. Friedman D B, Stauff D L, Pishchany G, Whitwell C W, Torres V J, Skaar E P. *Staphylococcus aureus* Redirects Central Metabolism to Increase Iron Availability. PLoS Pathog. 2006; 2(8).
69. Skaar E P, Gaspar A H, Schneewind O. IsdG and IsdI, heme-degrading enzymes in the cytoplasm of *Staphylococcus aureus*. J Biol Chem. 2004; 279(1):436-43.

70. Corbin B D, Seeley E H, Raab A, Feldmann J, Miller M R, Torres V J, et al. Metal chelation and inhibition of bacterial growth in tissue abscesses. Science. 2008; 319 (5865):962-5.
71. Attia A S, Benson M A, Stauff D L, Torres V J, Skaar E P. Membrane damage elicits an immunomodulatory program in *Staphylococcus aureus*. PLoS Pathog. 2010; 6(3):e1000802. PMCID: 2837406.
72. Skaar E, Humayun M, Bae T, DeBord K, Schneewind O. Iron-source preference of *Staphylococcus aureus* infections. Science. 2004; 305:1626-8.
73. Torres V, Pishchany G, Humayun M, Schneewind O, Skaar E. *Staphylococcus aureus* IsdB is a hemoglobin receptor required for heme iron utilization. J Bacteriol. 2006; 188:8421-9.
74. Jenkins A, Cote C, Twenhafel N, Merkel T, Bozue J, Welkos S. Role of purine biosynthesis in *Bacillus anthracis* pathogenesis and virulence. Infect Immun. 2011; 79(1):153-66. PMCID: 3019915.
75. Samant S, Hsu F F, Neyfakh A A, Lee H. The *Bacillus anthracis* protein MprF is required for synthesis of lysyl-phosphatidylglycerols and for resistance to cationic antimicrobial peptides. J Bacteriol. 2009; 191(4):1311-9. PMCID: 2631992.
76. Fry B, Zhu T, Domach M M, Koepsel R R, Phalakornkule C, Ataai M M. Characterization of growth and acid formation in a *Bacillus subtilis* pyruvate kinase mutant. Appl Environ Microbiol. 2000; 66(9):4045-9. PMCID: 92257.
77. Zhu T, Phalakornkule C, Koepsel R R, Domach M M, Ataai M M. Cell growth and by-product formation in a pyruvate kinase mutant of *E. coli*. Biotechnol Prog. 2001; 17(4):624-8.
78. Skaar E P, Gaspar A H, Schneewind O. *Bacillus anthracis* IsdG, a heme-degrading monooxygenase. J Bacteriol. 2006; 188(3):1071-80. PMCID: 1347327.
79. Mazmanian, S., E. Skaar, A. Gaspar, M. Humayun, P. Gornicki, J. Jelenska, A. Joachmiak, D. Missiakas, O. Schneewind. 2003. Passage of heme-iron across the envelope of *Staphylococcus aureus*. Science 299: 906-909.
80. Proctor, R., B. Kahl, C. von Eiff, P. Vaudaux, D. Lew, G. Peters. 1998. Staphylococcal small colony variants have novel mechanisms for antibiotic resistance. Clin. Infect. Dis. S68-74.
81. Skaar, E. P., D. Stauff, O. O. Aranmolate. U.S. Patent Application Publication No. 2010/0004324, published Jan. 7, 2010, filed Jun. 25, 2009, claiming priority to U.S. Provisional Patent Application No. 61/075,553, filed Jun. 25, 2008, which is also incorporated herein by this reference.
82. Pantosti A & Venditti M (2009) What is MRSA? *Eur Respir J* 34(5):1190-1196.
83. Somerville G A & Proctor R A (2009) At the crossroads of bacterial metabolism and virulence factor synthesis in staphylococci. *Microbiol Mol Biol Rev* 73(2):233-248.
84. Mazmanian S, et al. (2003) Passage of heme-iron across the envelope of *Staphylococcus aureus*. Science 299:906-909.
85. Johansson P & Hederstedt L (1999) Organization of genes for tetrapyrrole biosynthesis in Gram-positive bacteria. *Microbiology* 145(3):529-538.
86. Proctor R A, et al. (2006) Small colony variants: a pathogenic form of bacteria that facilitates persistent and recurrent infections. *Nat Rev Microbiol* 4(4):295-305.
87. Bryan L E & Kwan S (1981) Aminoglycoside-resistant mutants of *Pseudomonas aeruginosa* deficient in cytochrome d, nitrite reductase, and aerobic transport. *Antimicrob Agents Chemother* 19(6):958-964.
88. Torres V J, et al. (2007) A *Staphylococcus aureus* regulatory system that responds to host heme and modulates virulence. *Cell Host & Microbe* 1(2):109-119.
89. Fernandez A, et al. (2010) Two coregulated efflux transporters modulate intracellular heme and protoporphyrin IX availability in *Streptococcus agalactiae*. PLoS Pathog 6(4):e1000860.
90. Stauff D L & Skaar E P (2009) *Bacillus anthracis* HssRS signalling to HrtAB regulates haem resistance during infection. *Molecular Microbiology* 72(3):763-778.
91. von Eiff C, et al. (1997) A site-directed *Staphylococcus aureus* hemB mutant is a small-colony variant which persists intracellularly. *J Bacteriol* 179(15):4706-4712.
92. Reniere M L & Skaar E P (2008) *Staphylococcus aureus* haem oxygenases are differentially regulated by iron and haem. *Mol Microbiol* 69(5):1304-1315.
93. Schmitt M P (1999) Identification of a two-component signal transduction system from *Corynebacterium diphtheriae* that activates gene expression in response to the presence of heme and hemoglobin. *J Bacteriol* 181(17): 5330-5340.
94. Stauff D L, Torres V J, & Skaar E P (2007) Signaling and DNA-binding activities of the *Staphylococcus aureus* HssR-HssS two-component system required for heme sensing. *J Biol Chem* 282(36):26111-26121.
95. Youngman P J, Perkins J B, & Losick R (1983) Genetic transposition and insertional mutagenesis in *Bacillus subtilis* with *Streptococcus faecalis* transposon Tn917. *Proc Natl Acad Sci USA* 80(8):2305-2309.
96. McIllmurray M B & Lascelles J (1970) Anaerobiosis and the activity of enzymes of pyrimidine biosynthesis of *Staphylococcus aureus*. J Gen Microbiol 64(3).
97. Fitzpatrick T B, et al. (2007) Two independent routes of de novo vitamin B6 biosynthesis: not that different after all. *Biochem J* 407(1):1-13.
98. Wick A N, et al. (1957) Localization of the primary metabolic block produced by 2-deoxyglucose. *Journal of Biological Chemistry* 224(2):963-969.
99. DeLeo F R, Diep B A, & Otto M (2009) Host defense and pathogenesis in *Staphylococcus aureus* infections. *Infectious Disease Clinics of North America* 23(1):17-34.
100. Richardson A R, Libby S J, & Fang F C (2008) A nitric oxide-inducible lactate dehydrogenase enables *Staphylococcus aureus* to resist innate immunity. *Science* 319 (5870):1672-1676.
101. Cheng A G, DeDent A C, Schneewind O, & Missiakas D (2011) A play in four acts: *Staphylococcus aureus* abscess formation. *Trends Microbiol* 19(5):225-232.
102. Park M K, Myers R A M, & Marzella L (1992) Oxygen tensions and infections: Modulation of microbial growth, activity of antimicrobial agents, and immunologic responses. *Clinical Infectious Diseases* 14(3):720-740.
103. Burka L T, Washburn K D, & Irwin R D (1991) Disposition of [$^{14}$C]furan in the male F344 rat. *J Toxicol Environ Health* 34(2):245-257.
104. Manier M L, et al. (2011) Reagent precoated targets for rapid in-tissue derivatization of the anti-tuberculosis drug isoniazid followed by MALDI imaging mass spectrometry. *J Am Soc Mass Spectrom* 22(8):1409-1419.
105. Barker K D, Barkovits K, & Wilks A (2012) Metabolic flux of extracellular heme uptake in *Pseudomonas aeruginosa* is driven by the iron-regulated heme oxygenase (HemO). *Journal of Biological Chemistry* 287(22): 18342-18350.

106. Doss M & Philipp-Dormston W K (1973) Regulatory link between lactate dehydrogenase and biosynthesis of porphyrin and heme in microorganisms. *Enzyme* 16(1).
107. Frunzke J, Gatgens C, Brocker M, & Bott M (2011) Control of heme homeostasis in *Corynebacterium glutamicum* by the two-component system HrrSA. (Translated from eng) *J Bacteriol* 193(5):1212-1221 (in eng).
108. Jurtshuk P J (1996) Bacterial Metabolism. *Medical Microbiology*, ed Baron S (University of Texas Medical Branch at Galveston, Galveston), 4th Ed.

It will be understood that various details of the presently disclosed subject matter can be changed without departing from the scope of the subject matter disclosed herein. Furthermore, the foregoing description is for the purpose of illustration only, and not for the purpose of limitation.

SEQUENCE LISTING

```
<160> NUMBER OF SEQ ID NOS: 2

<210> SEQ ID NO 1
<211> LENGTH: 200
<212> TYPE: PRT
<213> ORGANISM: Artificial Sequence
<220> FEATURE:
<223> OTHER INFORMATION: Consensus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Met Lys Ser Leu Tyr Ser Arg Ile Val Val Thr Thr Val Gly Val
1               5                   10                  15

Ile Leu Leu Ser Ser Leu Ile Gly Phe Leu Leu Thr Asn Val Tyr Tyr
            20                  25                  30

Gln Ile Lys Leu Lys Pro Phe Asn Asp Glu Lys Ile Ala Lys Ile Ala
        35                  40                  45

Lys Glu Val Gln Gln Phe Tyr Glu Ser Gln Ser Glu Glu Ser Leu Glu
    50                  55                  60

Ala Tyr Leu Glu Ser Val Gly Glu Leu Gly Tyr Glu Ile Tyr Ile Val
65                  70                  75                  80

Asp Gly Gln Gly Asn Gly Thr Arg Tyr Gly Asn Ala Phe Arg Lys Lys
                85                  90                  95

Thr Leu Ser Asp Lys Thr Ile Lys Gln Val Leu Asn Gly Glu Thr Tyr
            100                 105                 110

His Gly Ile Ser Thr Tyr Pro Thr Gly Leu Phe Ile Thr Gly Phe Phe
        115                 120                 125

Asp Asn Glu Val Ile Asn Thr Val Gly Val Pro Val Lys His Asp Asp
    130                 135                 140

Lys Gln Leu Ala Leu Phe Ile Arg Pro Asp Ile Glu Gln Gln Phe Gly
145                 150                 155                 160

Glu Leu Arg Ile Phe Leu Ala Val Leu Leu Ile Phe Leu Val Leu Ile
                165                 170                 175

Ser Ile Leu Leu Val Ala Ile Ser Gly Arg Tyr Ile Val Arg Pro Val
            180                 185                 190

Val Lys Leu Thr Asn Ala Thr Gln
        195                 200

<210> SEQ ID NO 2
<211> LENGTH: 200
<212> TYPE: PRT
<213> ORGANISM: Staphylococcus aureus

<400> SEQUENCE: 2

Met Phe Lys Thr Leu Tyr Ala Arg Ile Ala Ile Tyr Ser Ile Thr Val
1               5                   10                  15
```

```
Ile Leu Phe Ser Ala Leu Ile Ser Phe Val Leu Thr Asn Val Tyr Tyr
            20                  25                  30

His Tyr Asn Leu Lys Ala Ser Asn Asp Ala Lys Ile Met Lys Thr Leu
            35                  40                  45

Lys Glu Ala Arg Gln Tyr Glu Gln Ser Ala Lys Pro Thr His Ile Gln
    50                  55                  60

Gln Tyr Phe Lys His Leu Gly Gln Met Asn Tyr Gln Ile Met Thr Ile
65                  70                  75                  80

Asp Gln Lys Gly His Lys Thr Phe Tyr Gly Glu Pro Phe Arg Glu Asp
                85                  90                  95

Thr Leu Ser Gln Asn Ala Ile Asn Asn Val Leu Asn Asn Gln Asp Tyr
            100                 105                 110

His Gly Ile Lys Asp Lys Pro Phe Ala Leu Phe Val Thr Gly Phe Phe
            115                 120                 125

Asp Asn Val Thr Asp Asn Thr Val Gly Ile Asn Phe Lys Thr Lys Asp
            130                 135                 140

Gly Ser Ile Ala Val Phe Met Arg Pro Asp Ile Gly Glu Thr Phe Ser
145                 150                 155                 160

Glu Phe Arg Thr Phe Leu Ala Val Leu Leu Met Leu Leu Leu Phe Ile
                165                 170                 175

Ser Ile Ser Leu Val Ile Ala Ser Thr Tyr Ser Ile Ile Arg Pro Val
            180                 185                 190

Lys Lys Leu Lys Leu Ala Thr Glu
            195                 200
```

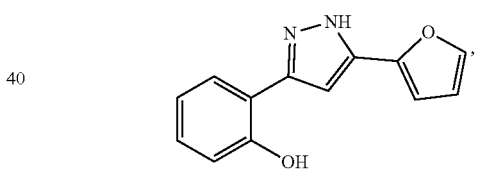

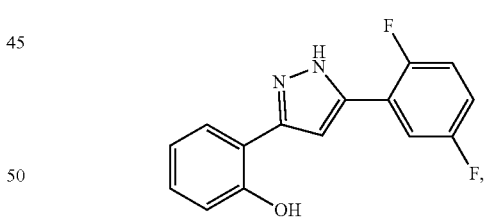

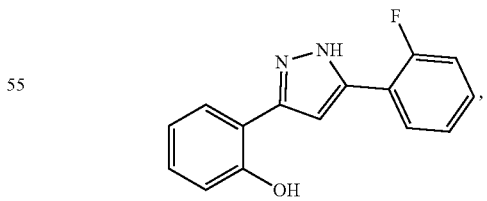

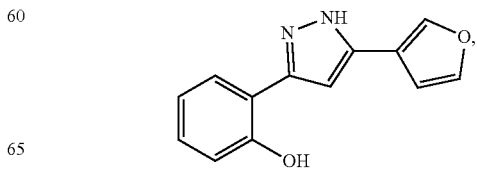

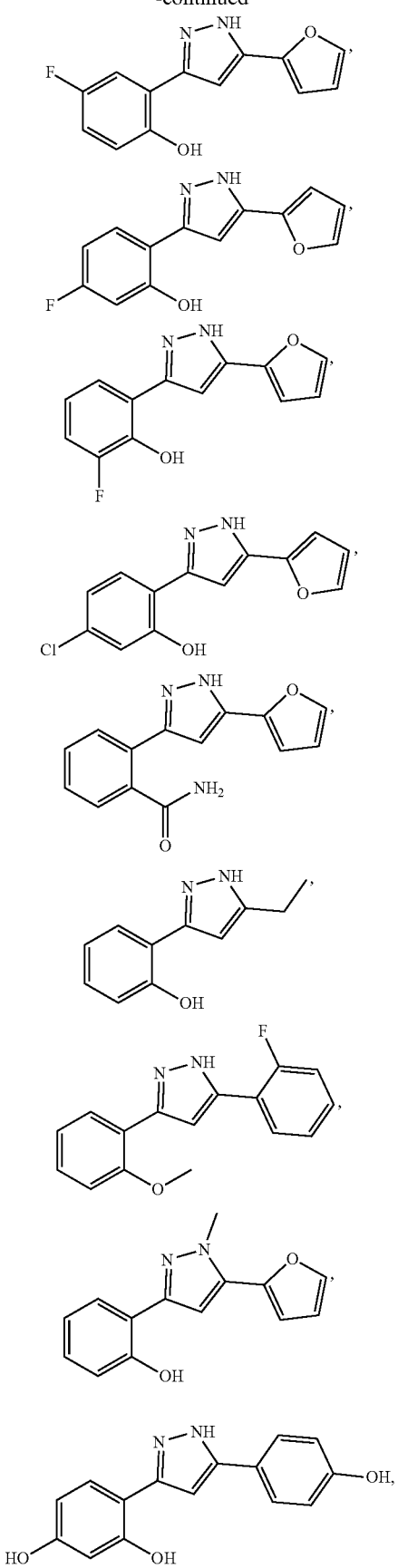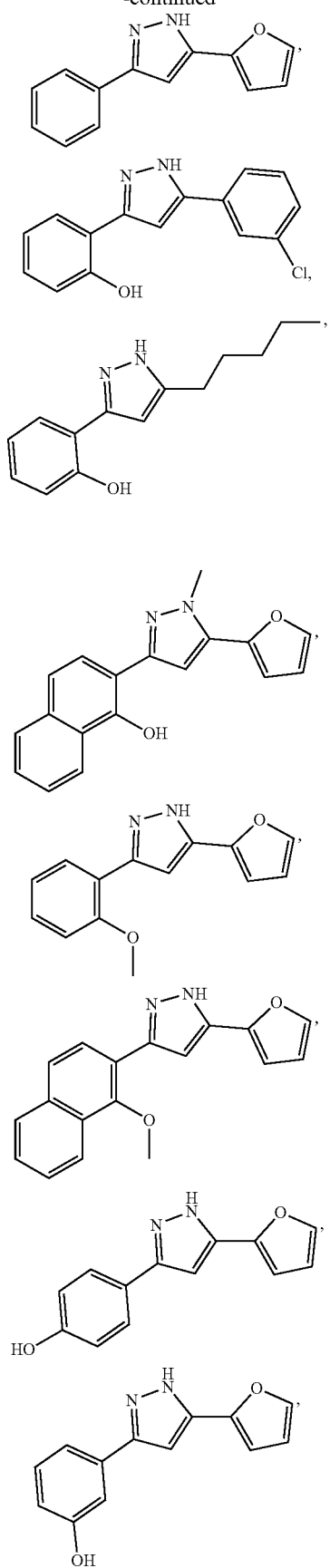

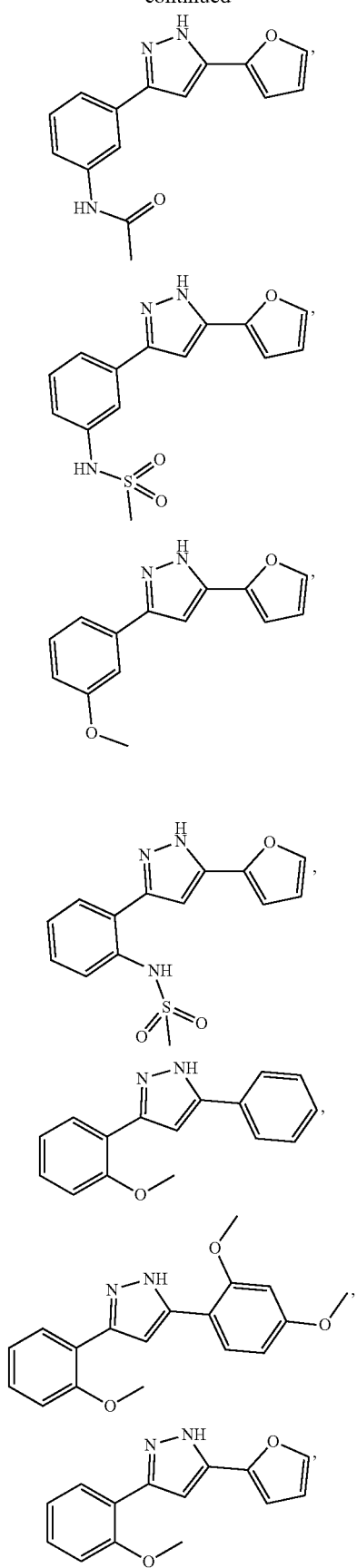
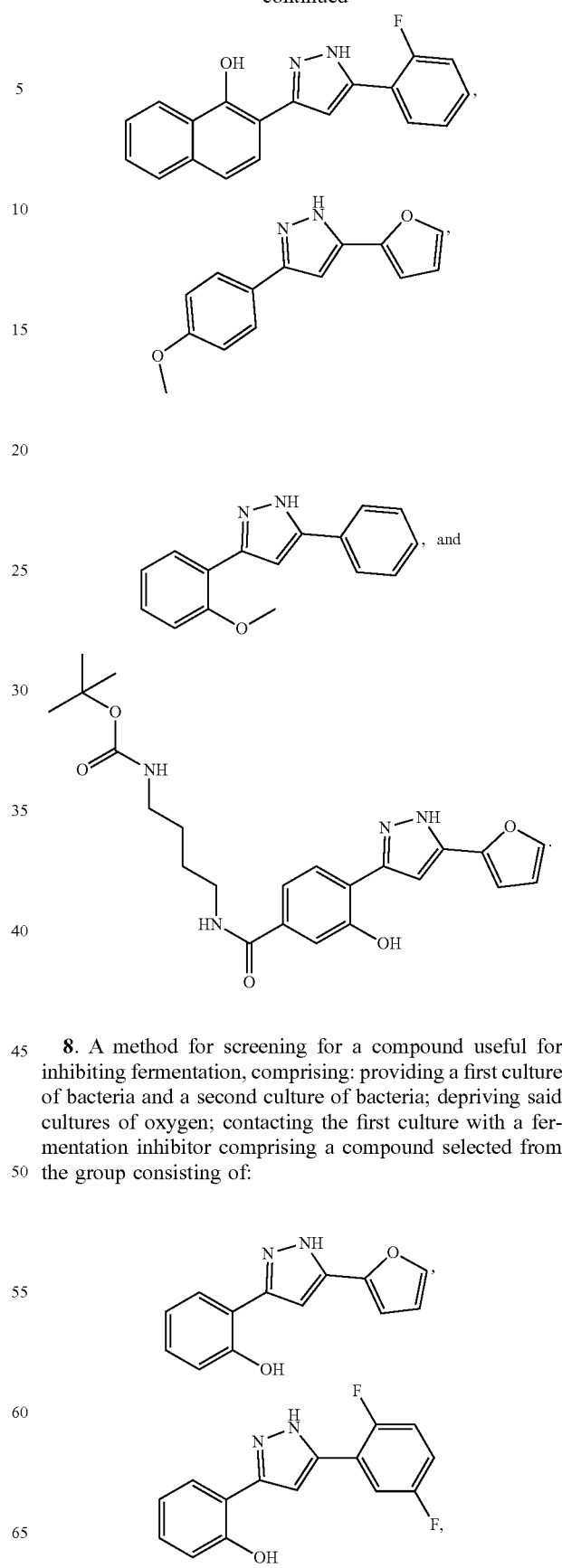
8. A method for screening for a compound useful for inhibiting fermentation, comprising: providing a first culture of bacteria and a second culture of bacteria; depriving said cultures of oxygen; contacting the first culture with a fermentation inhibitor comprising a compound selected from the group consisting of:
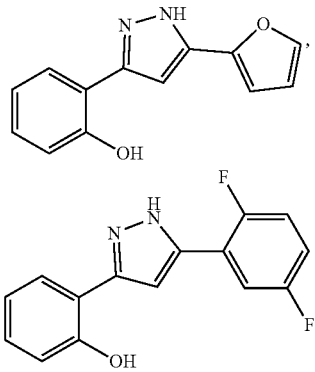

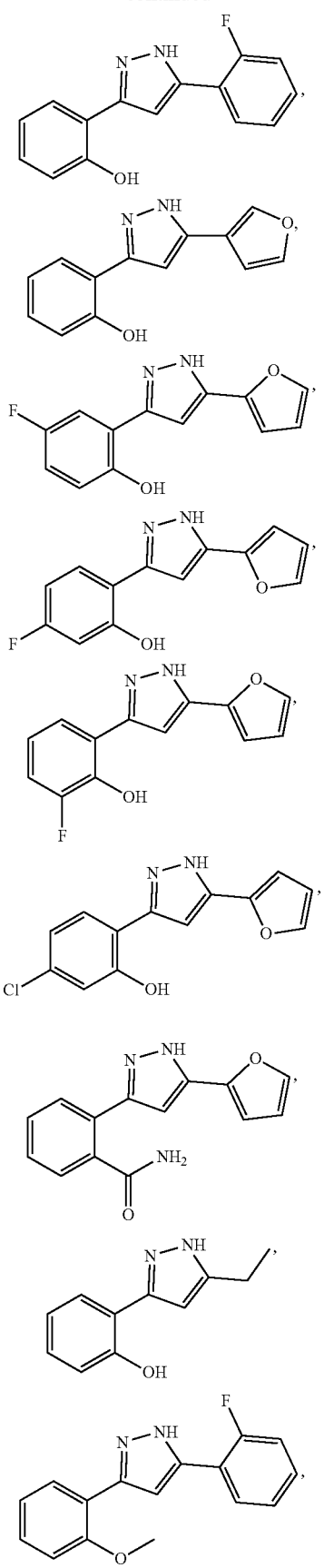
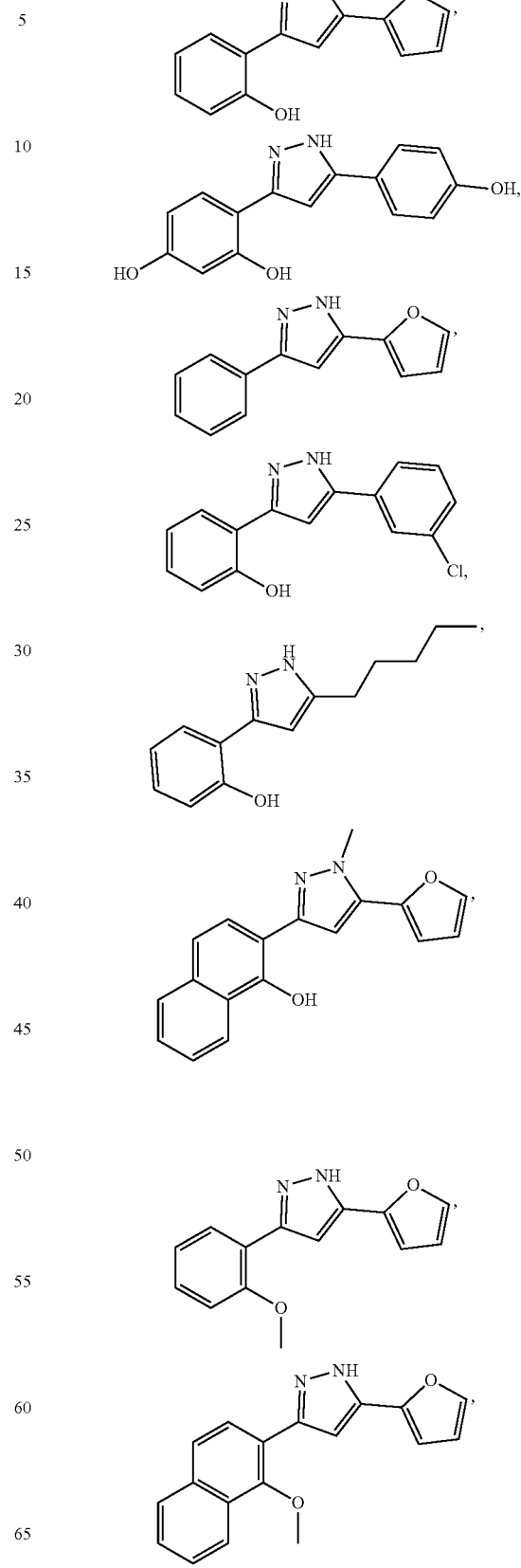

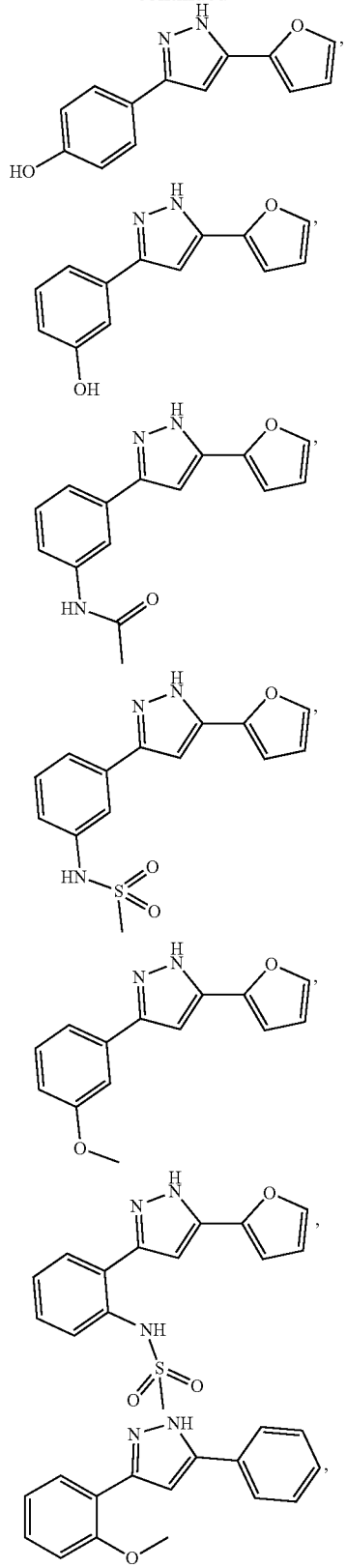
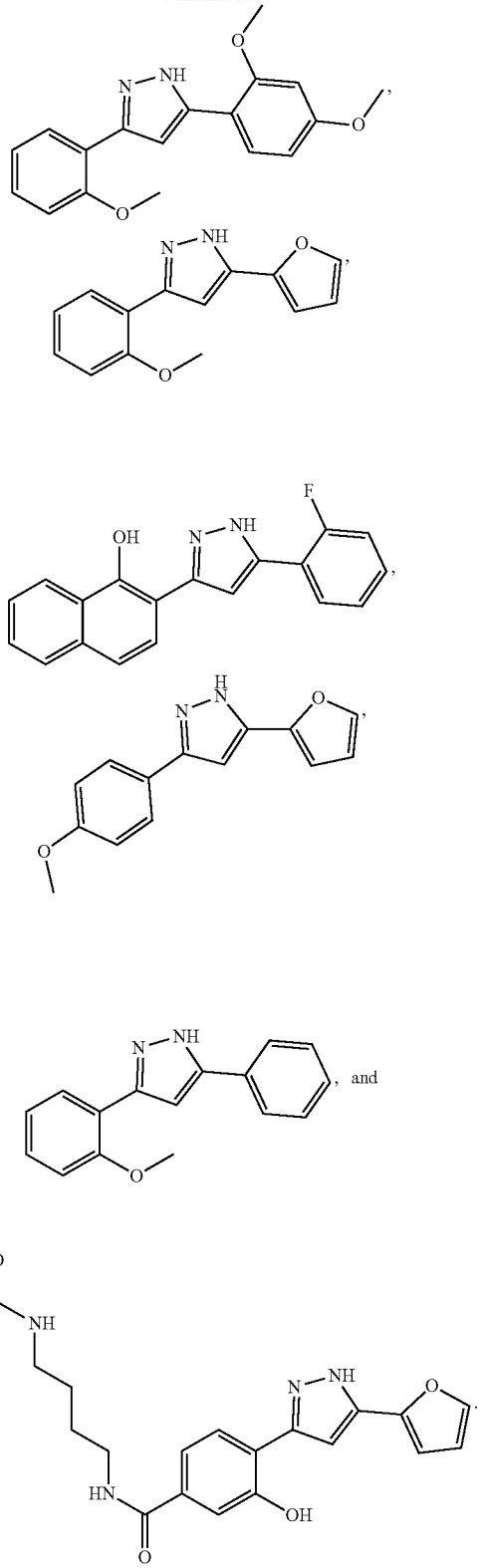

We claim:

1. A method for treating a microbial infection, comprising:

administering an effective amount of a fermentation inhibitor, comprising a compound selected from the group consisting of:

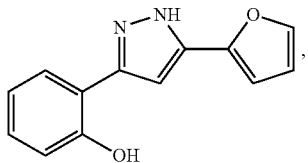

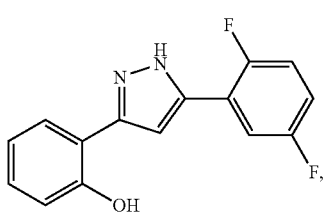

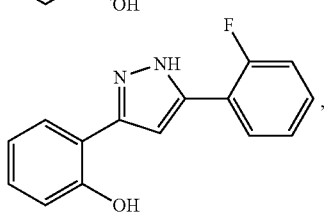

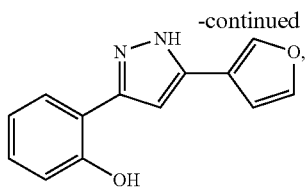

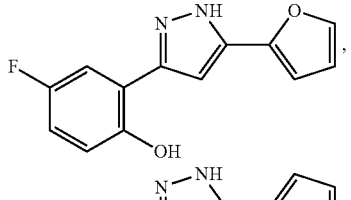

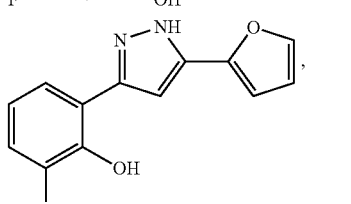

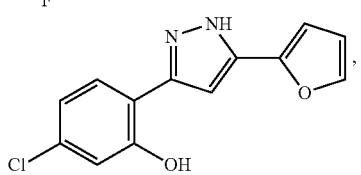

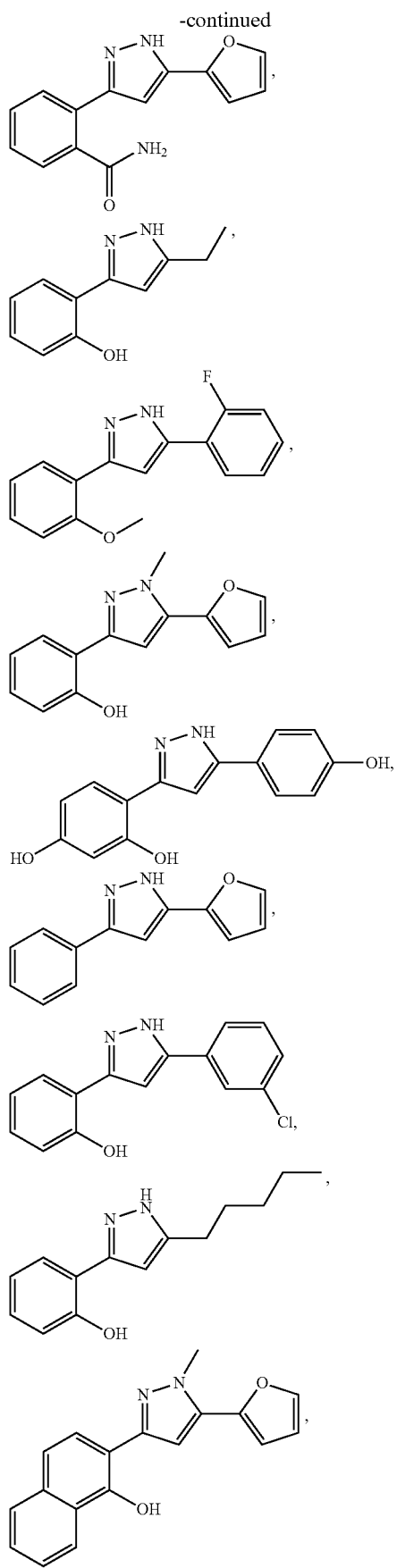
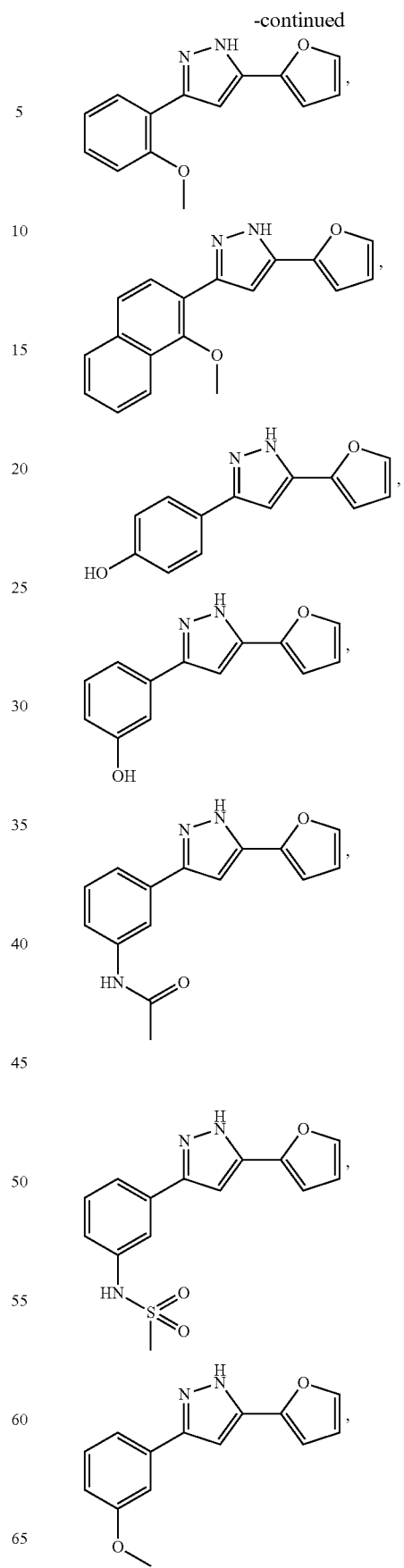

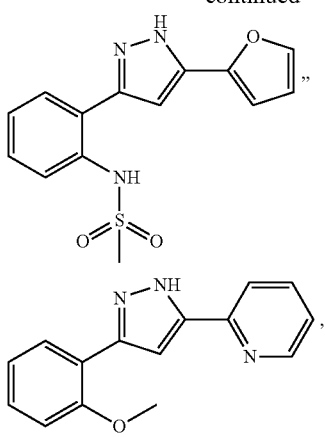

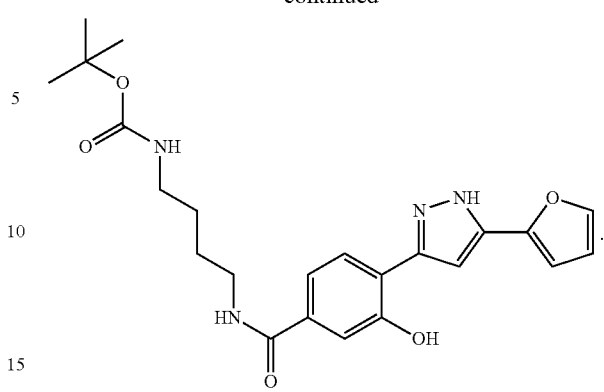

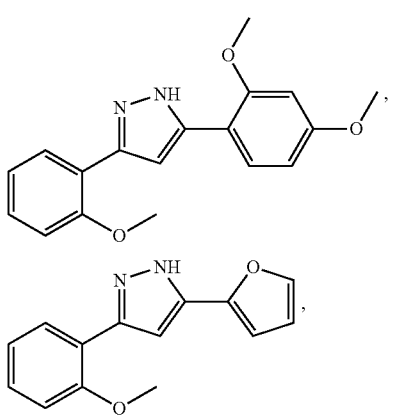

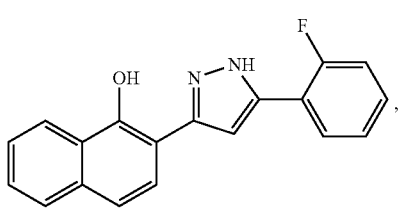

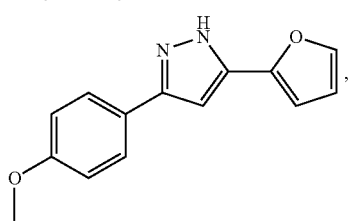

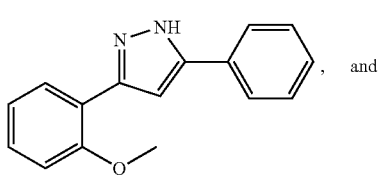, and

2. The method of claim 1, and further comprising administering an antimicrobial in addition to the fermentation inhibitor.

3. The method of claim 2, wherein the antimicrobial in an antibiotic.

4. The method of claim 3, wherein the antibiotic has an intracellular target.

5. The method of claim 4, wherein the antibiotic targets aerobically-growing bacteria.

6. The method of claim 5, wherein the antibiotic is an aminoglycoside.

7. A system, comprising: a device for creating an anaerobic environment adjacent a microbial infection; and a fermentation inhibitor comprising a compound selected from the group consisting of: